US012011619B2

(12) United States Patent
Guha et al.

(10) Patent No.: US 12,011,619 B2
(45) Date of Patent: Jun. 18, 2024

(54) LOW INTENSITY FOCUSED ULTRASOUND FOR TREATING CANCER AND METASTASIS

(71) Applicants: Montefiore Medical Center, Bronx, NY (US); Albert Einstein College of Medicine, Bronx, NY (US)

(72) Inventors: Chandan Guha, Scarsdale, NY (US); Stephen Barry, Haddonfield, NJ (US); Fernando Macian, Bronx, NY (US)

(73) Assignees: MONTEFIORE MEDICAL CENTER, Bronx, NY (US); ALBERT EINSTEIN COLLEGE OF MEDICINE, Bronx, NY (US)

( * ) Notice: Subject to any disclaimer, the term of this patent is extended or adjusted under 35 U.S.C. 154(b) by 77 days.

(21) Appl. No.: 17/191,497

(22) Filed: Mar. 3, 2021

(65) Prior Publication Data

US 2021/0268315 A1  Sep. 2, 2021

Related U.S. Application Data

(63) Continuation of application No. 15/578,892, filed as application No. PCT/US2016/035440 on Jun. 2, 2016, now Pat. No. 10,974,077.
(Continued)

(51) Int. Cl.
*A61N 7/00* (2006.01)
*A61B 5/00* (2006.01)
(Continued)

(52) U.S. Cl.
CPC ............... *A61N 7/00* (2013.01); *A61B 5/055* (2013.01); *A61B 5/4836* (2013.01);
(Continued)

(58) Field of Classification Search
CPC ... A61N 7/00; A61N 7/02; A61N 5/10; A61N 5/1077; A61N 2005/002; A61N 2005/1061; A61N 2005/1098; A61N 2007/0004; A61N 2007/0043; A61N 2007/0065; A61N 2007/0073; A61N 2007/0078; A61N 2007/0091; A61N 2007/0095;
(Continued)

(56) References Cited

U.S. PATENT DOCUMENTS

| 4,586,512 | A | 5/1986 | Do-Huu et al. |
| 7,194,063 | B2 | 3/2007 | Dilmanian et al. |

(Continued)

FOREIGN PATENT DOCUMENTS

| CN | 1947662 A | 4/2007 |
| CN | 104874114 A | 9/2015 |

(Continued)

OTHER PUBLICATIONS

U.S. Appl. No. 16/865,761 Office Action dated Jul. 25, 2022.
(Continued)

*Primary Examiner* — Peter Luong
(74) *Attorney, Agent, or Firm* — Wilson Sonsini Goodrich & Rosati

(57) ABSTRACT

Systems and methods for treating cancer and for preventing metastasis using low intensity focused ultrasound in combination with an anti-cancer therapy are disclosed.

20 Claims, 19 Drawing Sheets

Specification includes a Sequence Listing.

Related U.S. Application Data

(60) Provisional application No. 62/204,312, filed on Aug. 12, 2015, provisional application No. 62/170,378, filed on Jun. 3, 2015.

(51) Int. Cl.
| | |
|---|---|
| A61B 5/055 | (2006.01) |
| A61K 31/395 | (2006.01) |
| A61K 41/00 | (2020.01) |
| A61N 5/10 | (2006.01) |
| A61P 35/00 | (2006.01) |
| A61B 90/00 | (2016.01) |
| A61N 5/00 | (2006.01) |

(52) U.S. Cl.
CPC ........ *A61K 31/395* (2013.01); *A61K 41/0033* (2013.01); *A61N 5/10* (2013.01); *A61N 5/1077* (2013.01); *A61P 35/00* (2018.01); A61B 2090/374 (2016.02); A61B 2090/378 (2016.02); A61N 2005/002 (2013.01); A61N 2005/1061 (2013.01); A61N 2005/1098 (2013.01); A61N 2007/0004 (2013.01); A61N 2007/0043 (2013.01); A61N 2007/0065 (2013.01); A61N 2007/0073 (2013.01); A61N 2007/0078 (2013.01); A61N 2007/0091 (2013.01); A61N 2007/0095 (2013.01)

(58) Field of Classification Search
CPC ......... A61B 5/055; A61B 5/4836; A61B 5/06; A61B 2090/374; A61B 2090/378; A61B 2018/00005; A61B 2018/00023; A61B 8/08; A61K 31/395; A61P 35/00; A61P 35/04
See application file for complete search history.

(56) References Cited

U.S. PATENT DOCUMENTS

| | | | |
|---|---|---|---|
| 7,396,336 | B2 | 7/2008 | Orszulak et al. |
| 7,574,251 | B2 | 8/2009 | Lu et al. |
| 7,896,821 | B1 | 3/2011 | Magnin et al. |
| 10,974,077 | B2 | 4/2021 | Guha et al. |
| 2003/0055471 | A1 | 3/2003 | Fenn et al. |
| 2004/0034304 | A1 | 2/2004 | Sumi |
| 2005/0154431 | A1 | 7/2005 | Quistgaard et al. |
| 2007/0260144 | A1 | 11/2007 | Sela et al. |
| 2008/0260650 | A1 | 10/2008 | Tawakol et al. |
| 2009/0114846 | A1 | 5/2009 | Blankenbecler |
| 2009/0137996 | A1 | 5/2009 | DeBenedictis |
| 2010/0087728 | A1 | 4/2010 | Jarvik et al. |
| 2010/0092424 | A1 | 4/2010 | Sanghvi et al. |
| 2010/0106005 | A1 | 4/2010 | Karczmar et al. |
| 2010/0234728 | A1 | 9/2010 | Foley et al. |
| 2010/0286673 | A1 | 11/2010 | Altshuler et al. |
| 2011/0137158 | A1 | 6/2011 | Sumanaweera et al. |
| 2013/0022957 | A1 | 1/2013 | Chen et al. |
| 2013/0096595 | A1 | 4/2013 | Myhr et al. |
| 2014/0058293 | A1 | 2/2014 | Hynynen et al. |
| 2014/0257146 | A1 | 9/2014 | Kost et al. |
| 2014/0276069 | A1 | 9/2014 | Amble et al. |
| 2015/0141810 | A1 | 5/2015 | Weadock |
| 2015/0157383 | A1* | 6/2015 | Chao .................. A61N 7/02 606/27 |
| 2016/0345834 | A1 | 12/2016 | Hasan et al. |
| 2017/0271136 | A1 | 9/2017 | Roder et al. |
| 2017/0311804 | A1 | 11/2017 | Herring |
| 2018/0154183 | A1 | 6/2018 | Sahadevan |
| 2019/0111131 | A1 | 4/2019 | Nam et al. |
| 2020/0398084 | A1 | 12/2020 | Guha et al. |
| 2022/0288418 | A1 | 9/2022 | Guha et al. |

FOREIGN PATENT DOCUMENTS

| | | |
|---|---|---|
| CN | 106470735 A | 3/2017 |
| JP | 2005526579 A | 9/2005 |
| JP | 2007007279 A | 1/2007 |
| JP | 2011527931 A | 11/2011 |
| JP | 7105294 B2 | 7/2022 |
| WO | WO-0132258 A2 | 5/2001 |
| WO | WO-2009070245 A2 | 6/2009 |
| WO | WO-2011128693 A1 | 10/2011 |
| WO | WO-2015067786 A1 | 5/2015 |
| WO | WO-2015160708 A1 | 10/2015 |
| WO | WO-2016196741 A2 | 12/2016 |
| WO | WO-2017079431 A1 | 5/2017 |
| WO | WO-2018126277 A1 | 7/2018 |
| WO | WO-2018126280 A1 | 7/2018 |
| WO | WO-2019094802 A1 | 5/2019 |
| WO | WO-2020123388 A1 | 6/2020 |
| WO | WO-2021041557 A1 | 3/2021 |

OTHER PUBLICATIONS

Anelli et al. ERp44, a novel endoplasmic reticulum folding assistant of the thioredoxin family. EMBO J. 21(4):835-844 (2002).
Back et al. ER stress signaling by regulated splicing: IRE1/HAC1/XBP1. Methods 35(4):395-416 (2005).
Basu et al. Calreticulin, a peptide-binding chaperone of the endoplasmic reticulum, elicits tumor- and peptide-specific immunity. J Exp Med 189:797-802 (1999).
Basu et al. Necrotic but not apoptotic cell death releases heat shock proteins, which deliver a partial maturation signal to dendritic cells and activate the NF-kappa B pathway. Int immunol 12:1539-1546 (2000).
Bethune et al. Personalized T cell-mediated cancer immunotherapy: progress and challenges. Curr Opin Biotechnol 48:142-152 (2017).
Boussiotis et al. Prevention of T cell anergy by signaling through the gamma c chain of the IL-2 receptor. Science 266:1039-1042 (1994).
Cancer Research Institute. Focused Ultrasound and Immunotherapy Workshop. New York. Downloaded from https://d3nqfeqdtaoni.cloudfront.net/images/pdf/FUS_Immunotherapy_Workshop_Summary.pdf (pp. 1-13) (2015).
Castelli et al. Human heat shock protein 70 peptide complexes specifically activate antimelanoma T cells. Cancer Res 61:222-227 (2001).
Chen et al. Tumor cell membrane-bound heat shock protein 70 elicits antitumor immunity. Immunol Lett 84:81-87 (2002).
Cuenca et al. Extra-lymphatic solid tumor growth is not immunologically ignored and results in early induction of antigen-specific T-cell anergy: dominant role of cross-tolerance to tumor antigens. Cancer Res 63:9007-9015 (2003).
Curiel et al. Specific recruitment of regulatory T cells in ovarian carcinoma fosters immune privilege and predicts reduced survival. Nat Med 10:942-949 (2004).
Dong et al. Tumor-associated B7-H1 promotes T-cell apoptosis: a potential mechanism of immune evasion. Nat Med 8:793-800 (2002).
Dougan et al. Immune therapy for cancer. Annu Rev Immunol 27:83-117 (2009).
Driessens et al. Costimulatory and coinhibitory receptors in anti-tumor immunity. Immunol Rev 229:126-144 (2009).
Dure et al. IL-2 signaling prevents T cell anergy by inhibiting the expression of anergy-inducing genes. Mol Immunol 46:999-1006 (2009).
Enk et al. Dendritic cells as mediators of tumor-induced tolerance in metastatic melanoma. Int J Cancer 73:309-316 (1997).
Gajewski et al. Cancer immunotherapy strategies based on overcoming barriers within the tumor microenvironment. Curr Opin Immunol 25:268-276 (2013).
Gao et al. Analysis of sirtuin 1 expression reveals a molecular explanation of IL-2-mediated reversal of T-cell tolerance. PNAS USA 109:899-904 (2012).
Gerlini et al. Metastatic melanoma secreted IL-10 down-regulates CD1 molecules on dendritic cells in metastatic tumor lesions. Am J Pathol 165:1853-1863 (2004).

(56) References Cited

OTHER PUBLICATIONS

Gramaglia et al. Ox-40 ligand: a potent costimulatory molecule for sustaining primary CD4 T cell responses. J Immunol 161:6510-6517 (1998).
Green et al. Immunogenic and tolerogenic cell death. Nat Rev Immunol 9:353-363 (2009).
Haug et al. The heat shock protein Hsp70 enhances antigen-specific proliferation of human CD4+ memory T cells. Eur J Immunol 35:3163-3172 (2005).
Hetz et al. Targeting the unfolded protein response in disease. Nat Rev Drug Discov 12:703-719 (2013).
Hu et al. Investigation of HIFU-induced anti-tumor immunity in a murine tumor model. J Transl Med 5:34 (2007).
Hu et al. Release of endogenous danger signals from HIFU-treated tumor cells and their stimulatory effects on APCs. Biochem Biophys Res Comm 335:124-131 (2005).
Huang et al. Gr-1+CD115+ immature myeloid suppressor cells mediate the development of tumor-induced T regulatory cells and T-cell anergy in tumor-bearing host. Cancer Res 66:1123-1131 (2006).
Jeong et al. Ultrasound Transducer and System for Real-Time Simultaneous Therapy and Diagnosis for Noninvasive Surgery of Prostate Tissue. IEEE Transactions on Ultrasonics Ferroelectrics, and Frequency Control 56(9):1913-1922 (Sep. 2009).
Jessop et al. ERp57 is essential or efficient folding of glycoproteins sharing common structural domains. EMBO J. 26(1):28-40 (2007).
Kon et al. Chaperone-mediated autophagy is required for tumor growth. Sci Transl Med. 3(109):109ra117 (2011).
Lan et al. Ablative Hypofractionated Radiotherapy Normalizes Tumor Vasculature in Lewis Lung Carcinoma Mice Model. Radiation Research 179(4):458-464 (2013).
Lathrop et al. A signal through OX40 (CD134) allows anergic, autoreactive T cells to acquire effector cell functions. J Immunol 172:6735-6743 (2004).
Leach et al. Enhancement of antitumor immunity by CTLA-4 blockade. Science 271:1734-1736 (1996).
Lee et al. Characterization of circulating T cells specific for tumor-associated antigens in melanoma patients. Nat Med 5:677-685 (1999).
Lewis et al. Design and characterization of a high-power ultrasound driver with ultralow-output impedance. Review of Scientific Instruments 80:114704 (2009).
Liu et al. Overcoming Immune Tolerance to Cancer by Heat Shock Protein Vaccines. Mol Cancer Ther 1:1147-1151 (2002).
Macian et al. Transcriptional mechanisms underlying lymphocyte tolerance. Cell 109(6):719-731 (Jun. 14, 2002).
Marangoni et al. The transcription factor NFAT exhibits signal memory during serial T cell interactions with antigen-presenting cells. Immunity 38:237-249 (2013).
Munn et al. Indoleamine 2,3-dioxygenase and tumor-induced tolerance. J Clin Invest 117:1147-1154 (2007).
Murata et al. OX40 costimulation synergizes with GM-CSF whole-cell vaccination to overcome established CD8+ T cell tolerance to an endogenous tumor antigen. J Immunol 176:974-983 (2006).
Obeid et al. Leveraging the immune system during chemotherapy: moving calreticulin to the cell surface converts apoptotic death from "silent" to immunogenic. Cancer Res 67:7941-7944 (2007).
Overwijk et al. Tumor regression and autoimmunity after reversal of a functionally tolerant state of self-reactive CD8+ T cells. J Exp Med 198:569-580 (2003).
Partanen et al. Reduction of peak acoustic pressure and shaping of heated region by use of multifoci sonications in MR-guided high-intensity focused ultrasound mediated mild hyperthermia. Med Phys 40(1):013301 (2013).
Pawaria et al. CD91-dependent programming of T-helper cell responses following heat shock protein immunization. Nat Commun 2:521 (2011).
PCT/US2016/035440 International Preliminary Report on Patentability dated Dec. 14, 2017.
PCT/US2016/035440 International Search Report and Written Opinion dated Mar. 17, 2017.
PCT/US2018/060138 International Preliminary Report on Patentability dated May 12, 2020.
PCT/US2018/060138 International Search Report and Written Opinion dated Feb. 25, 2019.
PCT/US2018/060138 Invitation to pay fees dated Dec. 17, 2018.
Phan et al. Cancer regression and autoimmunity induced by cytotoxic T lymphocyte-associated antigen 4 blockade in patients with metastatic melanoma. PNAS USA 100:8372-8377 (2003).
Pouch et al. In vivo noninvasive temperature measurement by B-mode ultrasound imaging. J Ultrasound Med 29:1595-1606 (2010).
Rabinovich et al. Immunosuppressive strategies that are mediated by tumor cells. Annu Rev Immunol 25:267-296 (2007).
Ron et al. Signal integration in the endoplasmic reticulum unfolded protein response. Nat Rev Mol Cell Biol 8:519-529 (2007).
Rubinstein et al. Targeted inhibition of galectin-1 gene expression in tumor cells results in heightened T cell-mediated rejection; A potential mechanism of tumor-immune privilege. Cancer Cell 5:241-251 (2004).
Safford et al. Egr-2 and Egr-3 are negative regulators of T cell activation. Nat Immunol 6:472-480 (2005).
Saha et al. Low Intensity Focused Ultrasound (LOFU) Modulates Unfolded Protein Response and Sensitizes Prostate Cancer to 17AAG. Oncoscience 1(6):434-445 (2014).
Sahu et al. Live visualizations of single isolated tubulin protein self-assembly via tunneling current: effect of electromagnetic pumping during spontaneous growth of microtubule. Sci Rep 4:7303 (2014).
Sica et al. Altered macrophage differentiation and immune dysfunction in tumor development. J Clin Invest 117:1155-1166 (2007).
Somersan et al. Primary tumor tissue lysates are enriched in heat shock proteins and induce the maturation of human dendritic cells. J Immunol 167:4844-4852 (2001).
Soto-Nieves et al. Transcriptional complexes formed by NFAT dimers regulate the induction of T cell tolerance. J Exp Med 206:867-876 (2009).
Srivastava. Interaction of heat shock proteins with peptides and antigen presenting cells: chaperoning of the innate and adaptive immune responses. Annu Rev Immunol 20:395-425 (2002).
Staveley-O'Carroll et al. Induction of antigen-specific T cell anergy: An early event in the course of tumor progression. PNAS USA 95:1178-1183 (1998).
Ter Haar et al. Guidance on reporting ultrasound exposure conditions for bio-effects studies. Ultrasound Med Biol. 37(2):177-183 (2011).
Thomas et al. TGF-β Directly Targets Cytotoxic T Cell Functions During Tumor Evasion of Immune Surveillance. Cancer Cell 8:369-380 (2005).
Troy et al. Minimal recruitment and activation of dendritic cells within renal cell carcinoma. Clin Cancer Res 4:585-593 (1998).
Tsushima et al. Interaction between B7-H1 and PD-1 determines initiation and reversal of T-cell anergy. Blood 110:180-185 (2007).
Turk et al. Concomitant tumor immunity to a poorly immunogenic melanoma is prevented by regulatory T cells. J Exp Med 200:771-782 (2004).
Tutkun et al. A Cooperatively Controlled Robot for Ultrasound Monitoring of Radiation Therapy. Proceedings of the IEEE/RSJ International Conference on Intelligent Robots and Systems 2013:3071-3076 (Nov. 2013).
Udono et al. Comparison of tumor-specific immunogenicities of stress-induced proteins gp96, hsp90, and hsp70. J Imunol 152:5398-5403 (1994).
Udono et al. Heat shock protein 70-associated peptides elicit specific cancer immunity. J Exp Med 178:1391-1396 (1993).
Ullrich et al. A mouse tumor-specific transplantation antigen is a heat shock-related protein. PNAS USA 83:3121-3125 (1986).
U.S. Appl. No. 15/578,892 Office Action dated Aug. 19, 2020.
U.S. Appl. No. 15/578,892 Office Action dated Mar. 27, 2020.
Uyttenhove et al. Evidence for a tumoral immune resistance mechanism based on tryptophan degradation by indoleamine 2,3-dioxygenase. Nat Med 9:1269-1274 (2003).

(56) References Cited

OTHER PUBLICATIONS

Valdor et al. Induction and stability of the anergic phenotype in T cells. Semin Immunol 25:313-320 (2013).
Van Elsas et al. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med 190:355-366 (1999).
Vega et al. Hsp70 translocates into the plasma membrane after stress and is released into the extracellular environment in a membrane-associated form that activates macrophages. J Immunol 180:4299-4307 (2008).
White. Deconvoluting the context-dependent role for autophagy in cancer. Nat Rev Cancer 12(6):401-410 (2012).
Wilcox et al. Ligation of CD137 receptor prevents and reverses established energy of CD8+ cytolytic T lymphocytes in vivo. Blood 103:177-184 (2004).
Willimsky et al. Sporadic immunogenic tumours avoid destruction by inducing T-cell tolerance. Nature 437:141-146 (2005).
Yu et al. Identification of Prognosis-Relevant Subgroups in Patients with Chemoresistant Triple Negative Breast Cancer. Clin Cancer Res 19(10):1-18 (2013).
Zhang et al. CD40 ligation reverses T cell tolerance in acute myeloid leukemia. J Clin Invest 123:1999-2010 (2013).
Zhang et al. Hyperthermia on immune regulation: a temperature's story. Cancer Lett 271:191-204 (2008).
Zheng et al. Transcriptional regulator early growth response gene 2 (Egr2) is required for T cell anergy in vitro and in vivo. J Exp Med 209:2157-2163 (2012).
U.S. Appl. No. 16/865,761 Final Office Action dated Mar. 30, 2023.
Agoni et al. Variant splicing and influence of ionizing radiation on human endogenous retrovirus K (HERV-K) transcripts in cancer cell lines. PLOS One 8(10):e76472 (2013).
Apetoh et al. Toll-like receptor 4-dependent contribution of the immune system to anticancer chemotherapy and radiotherapy. Nat Med 13(9):1050-1059 (2007).
Benci et al. Tumor Interferon Signaling Regulates a Multigenic Resistance Program to Immune Checkpoint Blockade. Cell 167(6):1540-1554 (2016).
Billiard et al. Abdominal γ-radiation induces an accumulation of function-impaired regulatory T cells in the small intestine. International Journal of Radiation Oncology Biology Physics 80(3):869-76 (2011).
Chakraborty et al. Irradiation of tumor cells up-regulates Fas and enhances CTL lytic activity and CTL adoptive immunotherapy. J Immunol 170(12):6338-47 (2003).
Chakravarty et al. Flt3L therapy following localized tumor irradiation generates long-term protective immune response in metastatic lung cancer: its implication in designing a vaccination strategy. Oncology 70(4):245-254 (2006).
Chakravarty et al. Flt3-Ligand Administration after Radiation Therapy Prolongs Survival in a Murine Model of Metastatic Lung Cancer. Cancer Res 59(24):6028-6032 (1999).
Crittenden et al. Current clinical trials testing combinations of immunotherapy and radiation. Semin Radiat Oncol 25(1):54-64 (2015).
Crittenden et al. Expression of arginase I in myeloid cells limits control of residual disease after radiation therapy of tumors in mice. Radiat Res 182(2):182-90 (2014).
Demaria et al. Immune-mediated inhibition of metastases after treatment with local radiation and CTLA-4 blockade in a mouse model of breast cancer. Clin Cancer Res 11(2 Pt 1):728-34 (2005).
Demaria et al. Ionizing Radiation Inhibition Of Distant Untreated Tumors (Abscopal Effect) Is Immune Mediated. Int J radiat Oncol Biol Phys 58(3):862-870 (2004).
Dewan et al. Fractionated but not single-dose radiotherapy induces an immune-mediated abscopal effect when combined with anti-CTLA-4 antibody. Clin Cancer Res 15(17):5379-5388 (2009).
Filatenkov et al. Ablative Tumor Radiation Can Change the Tumor Immune Cell Microenvironment to Induce Durable Complete Remissions. Clin Cancer Res 21(16):3727-39 (2015).
Formenti et al. Systemic effects of local radiotherapy. Lancet Oncol 10(7):718-26 (2009).
Gameiro et al. Radiation-induced immunogenic modulation of tumor enhances antigen processing and calreticulin exposure, resulting in enhanced T-cell killing. Oncotarget 5(2):403-16 (2014).
Garcia-Barros et al. Tumor response to radiotherapy regulated by endothelial cell apoptosis. Science 300(5622):1155-9 (2003).
Golden et al. Radiation fosters dose-dependent and chemotherapy-induced immunogenic cell death. Oncoimmunology 3:e28518 (2014).
Gorchs et al. Cancer-associated fibroblasts from lung tumors maintain their immunosuppressive abilities after high-dose irradiation. Front Oncol 5:87 (2015).
Gough et al. The impact of the myeloid response to radiation therapy. Clin Dev Immunol 2013:281958 (2013).
Greco et al. Predictors of local control after single-dose stereotactic image-guided intensity-modulated radiotherapy for extracranial metastases. Int J Radiat Oncol Biol Phys 79(4):1151-7 (2011).
Hallahan et al. Targeting drug delivery to radiation-induced neoantigens in tumor microvasculature. J Control Release 74(1-3):183-91 (2001).
Hoyer et al., Radiotherapy for liver metastases: a review of evidence. Int J Radiat Oncol Biol Phys. 82(3):1047-1057 (2012).
Janiak et al. Cancer immunotherapy: how low-level ionizing radiation can play a key role. Cancer Immunology, Immunotherapy 66(7):819-32 (2017).
Kachikwu et al. Radiation enhances regulatory T cell representation. Int J Radiat Oncol Biol Phys 81(4):1128-35 (2011).
Kawashita et al. An autologous in situ tumor vaccination approach for hepatocellular carcinoma. 1. Flt3 ligand gene transfer increases antitumor effects of a radio-inducible suicide gene therapy in an ectopic tumor model. Radiat Res 182(2):191-200 (2014).
Kawashita et al. An autologous in situ tumor vaccination approach for hepatocellular carcinoma. 2. Tumor-specific immunity and cure after radio-inducible suicide gene therapy and systemic CD40-ligand and Flt3-ligand gene therapy in an orthotopic tumor model. Radiat Res 182(2):201-210 (2014).
Kioi et al. Inhibition of vasculogenesis, but not angiogenesis, prevents the recurrence of glioblastoma after irradiation in mice. J Clin Invest 120(3):694-705 (2010).
Klug et al. Low-dose irradiation programs macrophage differentiation to an iNOS+/M1 phenotype that orchestrates effective T cell immunotherapy. Cancer cell 24(5):589-602 (2013).
Kozin et al. Recruitment of myeloid but not endothelial precursor cells facilitates tumor regrowth after local irradiation. Cancer Res 70(14):5679-85 (2010).
Lee et al. Therapeutic effects of ablative radiation on local tumor require CD8+ T cells: changing strategies for cancer treatment. Blood 114(3):589-95 (2009).
Liu. Cancer control related to stimulation of immunity by low-dose radiation. Dose-response 5(1):39-47 (2007).
Liu et al. Enhancement of antitumor immunity by low-dose total body irradiation is associated with selectively decreasing the proportion and number of T regulatory cells. Cellular & Molecular immunology 7(2):157 (2010).
Liu et al. Low-Dose Total Body Irradiation Can Enhance Systemic Immune Related Response Induced by Hypo-Fractionated Radiation. Front Immunol 10:317 (2019).
Marconi et al. A meta-analysis of the abscopal effect in preclinical models: Is the biologically effective dose a relevant physical trigger? PLoS One 12(2):e0171559 (2017).
Martinez-Zubiaurre et al. Radiation-Induced Transformation of Immunoregulatory Networks in the Tumor Stroma. Front Immunol 9:1679 (2018).
Menon et al. Influence of low-dose radiation on abscopal responses in patients receiving high-dose radiation and immunotherapy. J Immunother Cancer 7:237 (2019).
Miller et al. Changes in the activation and reconstitution of lymphocytes resulting from total-body irradiation correlate with slowed tumor growth. Oncology 65(3):229-41 (2003).

(56) References Cited

OTHER PUBLICATIONS

Minn et al. Combination Cancer Therapies with Immune Checkpoint Blockade: Convergence on Interferon Signaling. Cell 165(2):272-275 (2016).

Morris et al. Tumor-Specific Inhibition of In Situ Vaccination by Distant Untreated Tumor Sites. Cancer Immunol Res 6(7):825-34 (2018).

North. Gamma-Irradiation facilitates the expression of adoptive immunity against established tumors by eliminating suppressor T cells. Cancer Immunology, Immunotherapy 16(3):175-81 (1984).

North. Radiation-induced, immunologically mediated regression of an established tumor as an example of successful therapeutic immunomanipulation. Preferential elimination of suppressor T cells allows sustained production of effector T cells. Journal of Experimental Medicine 164(5):1652-66 (1986).

Obeid et al. Calreticulin exposure dictates the immunogenicity of cancer cell death. Nat Med 13(1):54-61 (2007).

PCT/US2020/048020 International Search Report and Written Opinion dated Feb. 12, 2021.

Reits et al. Radiation modulates the peptide repertoire, enhances MHC class I expression, and induces successful antitumor immunotherapy. J Exp Med 203(5):1259-71 (2006).

Savage et al., Postablation modulation after single high-dose radiation therapy improves tumor control via enhanced immunomodulation. Clin Cancer Res. 26(4):910-921 (2020).

Schaue et al. Regulatory T cells in radiotherapeutic responses. Front Oncol 2:90 (2012).

Seetharam et al. Enhanced eradication of local and distant tumors by genetically produced interleukin-12 and radiation. Int J Oncol 15(4):769-73 (1999).

Seung et al. Phase 1 study of stereotactic body radiotherapy and interleukin-2—tumor and immunological responses. Sci Transl Med 4(137):137ra74 (2012).

Shimura et al. Effects of low-dose-gamma rays on the immune system of different animal models of disease. Does Response 12(3):429-465 (2014).

Stone et al. Effect of host immune capability on radiocurability and subsequent transplantability of a murine fibrosarcoma. J Natl Cancer Inst 63(5):1229-35 (1979).

Timmerman et al. Stereotactic body radiation therapy for inoperable early stage lung cancer. JAMA 303(11):1070-1076 (2010).

Vanpouille-Box et al. DNA exonuclease Trex1 regulates radiotherapy-induced tumour immunogenicity. Nat Commun 8:15618 (2017).

Vanpouille-Box et al. TGFbeta Is a Master Regulator of Radiation Therapy-Induced Antitumor Immunity. Cancer Res 75(11):2232-42 (2015).

Wennerberg et al. Barriers to Radiation-Induced In Situ Tumor Vaccination. Front Immunol 8:229 (2017).

Yamada et al. High-dose, single-fraction image-guided intensity-modulated radiotherapy for metastatic spinal lesions. Int J Radiat Oncol Biol Phys 71(2):484-90 (2008).

Zhang et al. An in situ autologous tumor vaccination with combined radiation therapy and TLR9 agonist therapy. PLoS One 7(5):e3811 (2012).

Zhang et al. Induced sensitization of tumor stroma leads to eradication of established cancer by T cells. J Exp Med 204(1):49-55 (2007).

Znati et al. Irradiation reduces interstitial fluid transport and increases the collagen content in tumors. Clin Cancer Res 9(15):5508-13 (2003).

EP20857760.1 Extended European Search Report dated Oct. 5, 2023.

EP16804398.2 Extended European Search Report dated Jan. 19, 2022.

EP18876112.6 Extended European Search Report dated Jul. 28, 2021.

U.S. Appl. No. 15/578,892 Notice of Allowance dated Dec. 9, 2020.

U.S. Appl. No. 16/865,761 Office Action dated Oct. 24, 2023.

\* cited by examiner

LOW INTENSITY FOCUSED ULTRASOUND FOR TREATING CANCER AND METASTASIS

CROSS-REFERENCE TO RELATED APPLICATIONS

This application is a continuation of U.S. application Ser. No. 15/578,892, filed Dec. 1, 2017, which is the National Phase entry of International Application No. PCT/US2016/035440, filed Jun. 2, 2016, which claims the benefit of U.S. Provisional Application No. 62/170,378, filed Jun. 3, 2015, and of U.S. Provisional Application No. 62/204,312, filed Aug. 12, 2015, the contents of each are incorporated herein by reference in their entireties.

STATEMENT OF GOVERNMENT SUPPORT

This invention was made with government support under grant numbers EB009040 and A1059738 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 2, 2021, is named 52650-704_301_SL.txt and is 5,076 bytes in size.

BACKGROUND OF THE INVENTION

Throughout this application various publications are referred to in brackets. Full citations for these references may be found at the end of the specification. The disclosures of these publications, and of all patents, patent application publications and books referred to herein, are hereby incorporated by reference in their entirety into the subject application to more fully describe the art to which the subject invention pertains.

Immune responses against cancer cells are frequently hampered by the immunosuppressive nature of the tumor microenvironment, which is also responsible for hindering the efficacy of cancer immunotherapy (1, 2). Several mechanisms have been identified underlying the ability of tumors to generate an immunosuppressive environment, including secretion of cytokines or other factors with inhibitory activity (3-5), recruitment of regulatory T cells and myeloid-derived suppressor cells (6-9), increased expression of ligands for co-inhibitory receptors (10-13) or inhibition of dendritic cell maturation (14, 15). As a consequence of those mechanisms T cells are often rendered unresponsive to tumor antigens (15). Induction of a hyporesponsive state to tumor antigens occurs both in CD4+ and CD8+ T cell populations and is often responsible for the inability of the adaptive immune system to mount an efficient anti-tumor response (16-18). Decreased T cell responses to tumor antigens occur in both solid and hematological tumors and appear to be caused by inefficient presentation of antigens by dendritic cells, which results in the preferential activation of tolerogenic programs of gene expression that are dependent on the transcription factors NFAT and Egr2 (18-21). The important role of this process of tumor-induced T cell hyporesponsiveness is underscored by the fact that genetic mouse models where the induction of this tolerogenic gene expression program is prevented result in enhanced anti-tumor T cell responses and control of tumor growth (19, 21).

Treatment of localized tumors by focused ultrasound (FUS) is an image guided minimally invasive therapy that uses a range of input energy for in situ tumor ablation (22, 23). The application of FUS to biological tissues is associated with the generation of thermal and cavitation effects, causing changes in target cell physiology, depending on the energy delivered. High intensity focused ultrasound (HIFU) has been used clinically to thermally ablate localized tumors (23-26). The substantial thermal energy generated by that modality of FUS treatment causes rapid coagulative necrosis of the tissue at the targeted focal spots. Though several studies have reported some immunomodulatory effects, including increased lymphocyte infiltration, generation of IFNγ producing tumor-specific T cells in lymphoid organs and dendritic cell maturation and migration into tumors (26, 27), the thermally induced coagulative necrosis resulting from HIFU treatment can also attenuate the release of immunostimulatory molecules within the tumor microenvironment. Thus, although able to halt the progression of established primary tumors, HIFU might fail to protect against local and distant metastases arising from the surviving tumor cells.

The present invention provides improved tumor and cancer treatments employing low intensity focused ultrasound, and methods of inducing chemosensitization and increasing the efficacy of cancer otherapy treatments.

SUMMARY OF THE INVENTION

A method is provided for increasing the efficacy of a chemotherapy in a subject comprising administering to the subject (i) an amount of low intensity focused ultrasound (LOFU) and (ii) an amount of a chemotherapeutic drug, wherein the chemotherapeutic drug effects endoplasmic reticulum (ER) stress and/or unfolded protein response (UPR) in a tumor cell, wherein the amounts (i) and (ii) together are sufficient to increase the efficacy of the chemotherapy.

Also provided is a method of increasing the efficacy of a chemotherapy in a predetermined volume of tissue in a subject which volume is less than the whole subject, comprising (i) administering to the subject an amount of a chemotherapeutic drug, wherein the chemotherapeutic drug effects endoplasmic reticulum (ER) stress and/or unfolded protein response (UPR) in a tumor cell and (ii) administering to the predetermined volume of tissue in a subject an amount of low intensity focused ultrasound (LOFU), wherein the amounts of (i) and (ii) together are sufficient to increase efficacy of the chemotherapy within the predetermined volume of tissue.

A method of treating a tumor in a subject is provided, wherein the tumor is resistant to a chemotherapeutic drug, comprising:
  receiving identification of the subject as having a tumor resistant to a specified chemotherapeutic drug;
  administering (i) an amount of low intensity focused ultrasound (LOFU) and (ii) an amount of the specified chemotherapeutic drug,
  wherein the amounts (i) and (ii) together are sufficient to treat the tumor.

Also provided is a method of treating a chemoresistant tumor in a subject, wherein the tumor has become chemoresistant to a previously administered chemotherapeutic drug, comprising:

administering to the subject (i) an amount of low intensity focused ultrasound (LOFU) and (ii) an amount of the chemotherapeutic drug, wherein the amounts (i) and (ii) together are sufficient to treat the chemoresistant tumor.

Acoustic priming therapy (APT) systems according to various exemplary embodiments of the present invention comprise transducers configured to produce acoustic power between 10 and 1000 W/cm² spatial peak temporal average intensity (Ispta) in a treatment zone, wherein the frequency of the ultrasound is in the range of 0.01 to 10 MHz, the mechanical index is less than 4 and the ultrasound is applied continuously from a time in the range of 0.5 to 5 seconds for any particular volume in the treatment zone. Such treatments are identified herein as acoustic priming therapy (APT) treatments.

An acoustic priming therapy device according to an exemplary embodiment of the present invention comprises: a control system that generates a frequency waveform; and one or more transducers each configured to produce ultrasonic beams based on the frequency waveform with a peak frequency in the range of 0.5 to 5 MHz and an acoustic output intensity of between 20 and 1000 W/cm².

In an exemplary embodiment, each transducer is configured to produce columnated ultrasound such that the beam profile waist at −3 dB is not less than 5 mm in a treatment zone.

In an exemplary embodiment, two or more transducers can be operated sequentially or simultaneously and produce ultrasound of average spatial peak 250 J/cm² in a treatment zone during a treatment period.

In an exemplary embodiment, the transducers are operated in continuous mode wherein ultrasound is produced in a treatment zone for a treatment period in the range of 0.1 to 10 seconds.

A system according to an exemplary embodiment of the present invention comprises: an acoustic priming therapy device comprising: a control system that generates a frequency waveform; and one or more transducers configured to produce ultrasound based on a frequency waveform between 1 and 1000 W/cm² spatial peak temporal average acoustic output intensity ($I_{spta}$) in a treatment zone, wherein the ultrasound is applied continuously for a time in the range of 0.5 to 5 seconds, and wherein ultrasound frequency is in the range of 0.01 to 10 MHz; a radiotherapy treatment machine; and a control system operatively configured to control the acoustic priming therapy device and the radiotherapy treatment machine so that a first amount of the ultrasound and a second amount of radiotherapy are administered to a subject, wherein the first and second amounts together are sufficient to treat a tumor in the subject.

A system according to an exemplary embodiment of the present invention comprises: an acoustic priming therapy device comprising: a control system that generates a frequency waveform; and one or more transducers configured to produce ultrasound based on a frequency waveform between 1 and 1000 W/cm² spatial peak temporal average acoustic output intensity (Ispta) in a treatment zone, wherein the ultrasound is applied continuously for a time in the range of 0.5 to 5 seconds, and wherein ultrasound frequency is in the range of 0.01 to 10 MHz; the acoustic priming therapy device for use in combination with chemotherapy so that a first amount of the ultrasound and a second amount of chemotherapy are administered to a subject, wherein the first and second amounts together are sufficient to treat a tumor in the subject.

A system according to an exemplary embodiment of the present invention comprises: an acoustic priming therapy device comprising: a control system that generates a frequency waveform; and one or more transducers configured to produce ultrasound based on a frequency waveform between 1 and 1000 W/cm² spatial peak temporal average acoustic output intensity (Ispta) in a treatment zone, wherein the ultrasound is applied continuously for a time in the range of 0.5 to 5 seconds, and wherein ultrasound frequency is in the range of 0.01 to 10 MHz; the acoustic priming therapy device for use in combination with immunotherapy so that a first amount of the ultrasound and a second amount of the immunotherapy are administered to a subject, wherein the first and second amounts together are sufficient to treat a tumor in the subject.

A method of treating a tumor in a subject is provided comprising administering to the subject (i) an amount of low intensity focused ultrasound (LOFU) and (ii) an amount of chemotherapy or an amount of radiotherapy or an amount of immunotherapy, wherein the amounts of (i) and (ii) together are sufficient to treat a tumor.

Also provided is a method of inhibiting metastasis of a tumor in a subject, comprising administering to a subject having a tumor an amount of low intensity focused ultrasound (LOFU) and an amount of a radiotherapy, wherein the amounts together are sufficient to treat a tumor.

Also provided is a method of reducing the effective dose of an anti-cancer chemotherapy required to treat a tumor in a subject comprising administering to the subject undergoing the anti-cancer chemotherapy an amount of low intensity focused ultrasound (LOFU) sufficient to reduce the effective dose of the anti-cancer chemotherapy required to treat a tumor.

Also provided is a method of sensitizing a tumor in a subject to an amount of an anti-cancer therapy the method comprising administering to the subject, prior to or during the course of the anti-cancer therapy, an amount of an acoustic priming therapy effective to sensitize a tumor in a subject to an amount of an additional anti-cancer therapy modality.

A method of treating a tumor in a subject is provided comprising administering to the subject (i) an amount of low intensity focused ultrasound (LOFU) with LOFU herein indicating an exemplary embodiment of an ultrasound configuration used in an APT system, and (ii) an amount of chemotherapy or an amount of radiotherapy or an amount of immunotherapy, wherein the amounts of (i) and (ii) together are sufficient to treat a tumor.

Also provided is a method of inhibiting metastasis of a tumor in a subject, comprising administering to a subject having a tumor an amount of low intensity focused ultrasound (LOFU) and an amount of a radiotherapy, wherein the amounts together are sufficient to inhibit metastasis of a tumor in a subject.

Also provided is a method of reducing the effective dose of an anti-cancer chemotherapy required to treat a tumor in a subject comprising administering to the subject undergoing the anti-cancer chemotherapy an amount of low intensity focused ultrasound (LOFU) sufficient to reduce the effective dose of the anti-cancer chemotherapy required to treat a tumor.

Also provided is a method of sensitizing a tumor in a subject to an amount of an anti-cancer therapy the method comprising administering to the subject, prior to or during the course of the anti-cancer therapy, an amount of low intensity focused ultrasound (LOFU) effective to sensitize a tumor in a subject to an amount of an anti-cancer therapy.

DETAILED DESCRIPTION OF THE INVENTION

Figures 1A, 1B, 1C, 1D, 1E, 1F:
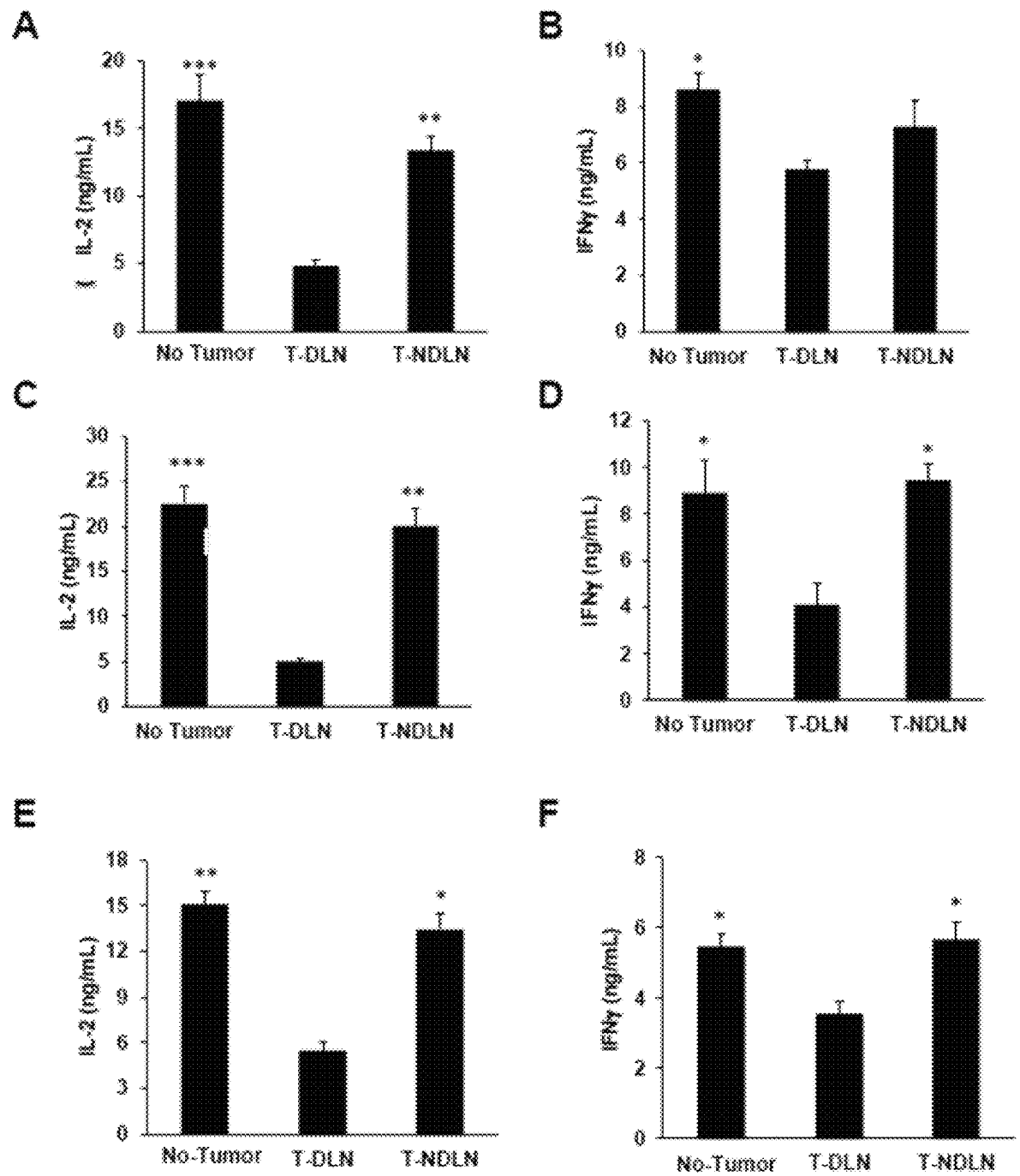
FIG. 1A-1F. Melanoma tumors suppress cytokine output of CD4+ T cells: 1A-B: C57Bl/6 mice were challenged in the lumbar flanks with $3\times10^5$ B16-F1 melanoma cells. Tumors were allowed to grow to 7-8 mm$^3$ in size. CD4+ T cells were isolated from the tumor DLN and distal contralateral NDLN, and stimulated with anti-CD3 and anti-CD28 antibodies. IL-2 and IFNγ were measured by ELISA. CD4+ T cells from tumor-free mice were used as controls. 1C-D: OTII mice were challenged with $3\times10^5$ B16-F1-OVA melanoma cells as described. T cells were stimulated with OVA323-339 peptide-loaded splenocytes and IL-2 and IFNγ production measured by ELISA. 1E-F. B16-F1 cells were used to induce tumors in Tyrp1 mice as described above. Isolated CD4+ T cells were stimulated with anti-CD3 and anti-CD28 antibodies and IL-2 and IFNγ production determined by ELISA. Graphs show mean+SEM from 4 (1A-B) or 3 (1C-F) independent experiments. Results are shown as mean+SEM from 3-5 mice for each experiment. Data were analyzed using ANOVA with a Tukey post-test (*$P<0.01$; $P<0.01$; *$P<0.05$).

Disclosed herein is an ultrasound (US) therapy that delivers a reduced level of energy to a treatment zone compared to HIFU configurations. In an exemplary embodiment, the treatment of a particular lesion volume is for a short time (e.g. ~1.5 sec) at 1 MHz continuous power, with tumor tissue temperature elevated to less than about 45° C. This ultrasound treatment, generated using a concave transducer to focus the ultrasound in a treatment zone and herein termed "low energy non-ablative focused ultrasound" (LOFU), produces mild mechanical and thermal stress in tumor cells, while avoiding cavitation and coagulative necrosis both of which result in tissue damage. A non-ablative "sonic" stress response is induced in the tumor that increases the expression of heat shock proteins without actually killing them directly. LOFU has the potential to release immunomodulatory factors, including heat shock proteins (28, 29), and can be effective in inducing tumor-specific immune activation (30, 31). Using a murine B16 melanoma tumor model, it is disclosed that LOFU treatment reverses tumor-induced tolerance, resulting in increased effector cytokine production in tumor-antigen specific CD4+ T cells, which appears to be caused by the release of immunogenic molecules by the tumor cells. Also, the combination of LOFU with an ablative hypofractionated Cone Beam computed tomography (CT) image-guided radiation therapy (IGRT) results in synergistic control of primary tumors and also causes reduction in spontaneous pulmonary metastases and prolongs recurrence free survival in immunocompetent mice (see Example 1). In addition, LOFU was found to sensitize cancer cells (prostate cancer in the example) to a chemotherapeutic (see Example 2).

In an exemplary embodiment, the LOFU (also termed "acoustic priming therapy" herein) involves the application of ultrasound at an acoustic power between 10 and 1000 W/cm$^2$ spatial peak temporal average intensity (Ispta) in a treatment zone, with the ultrasound applied continuously for a time in the range of 0.5 to 5 seconds, wherein the frequency is in the range of 0.01 to 10 MHz and the mechanical index is less than 4. Mechanical Index (MI) is the rarefaction pressure in units of MPa over the square root of the central frequency in units of MHz. The energy and intensity of ultrasound applied is intended to fall between energies and intensities of ultrasound that either induce primarily ablative effects or primarily diagnostic effects.

As explained in more detail below, the various treatment methods discussed herein may be administered using a LOFU or acoustic priming therapy device that includes a transducer that generates acoustic power between 10 and 1000 W/cm$^2$ spatial peak temporal average intensity ($I_{spta}$) in a treatment zone. The ultrasound is applied continuously for a time in the range of 0.5 to 5 seconds or pulsed with pulse durations of 1 to 100 ms, wherein the frequency is in the range of 0.01 to 10 MHz. In some embodiments the frequency is in the range of 0.05 to 5 MHz. In some embodiments the frequency range is from 0.1 to 2 MHz. In some embodiments the minimum diameter of any ultrasound beam in the treatment zone is about 1 cm. In an embodiment, the LOFU is administered at 10 to 100 W/cm$^2$ $I_{spta}$ in the area of treatment. In an embodiment, the LOFU is administered at 100 to 200 W/cm$^2$ $I_{spta}$ in the area of treatment. In an embodiment, the LOFU is administered at 300 to 400 W/cm$^2$ $I_{spta}$ in the area of treatment. In an embodiment, the LOFU is administered at 400 to 500 W/cm$^2$ $I_{spta}$ in the area of treatment. In an embodiment, the LOFU is administered at 500 to 600 W/cm$^2$ $I_{spta}$ in the area of treatment. In an embodiment, the LOFU is administered at 600 to 700 W/cm$^2$ $I_{spta}$ in the area of treatment. In an embodiment, the LOFU is administered at 700 to 800 W/cm$^2$ $I_{spta}$ in the area of treatment. In an embodiment, the LOFU is administered at 800 to 900 W/cm$^2$ $I_{spta}$ in the area of treatment. In an embodiment, the LOFU is administered at 900 to 1000 W/cm$^2$ $I_{spta}$ in the area of treatment. In an embodiment, the ultrasound is applied for a time in the range of 0.5 to 1 second. In an embodiment, the ultrasound is applied for a time in the range of 1 to 2 seconds. In an embodiment, the ultrasound is applied for a time in the range of 2 to 3 seconds. In an embodiment, the ultrasound is applied for a time in the range of 4 to 5 seconds. In embodiment, the ultrasound is applied at a frequency of 0.01 to 1 MHz. In embodiment, the ultrasound is applied at a frequency of 1 to 2 MHz. In embodiment, the ultrasound is applied at a frequency of 2 to 3 MHz. In embodiment, the ultrasound is applied at a frequency of 3 to 4 MHz. In embodiment, the ultrasound is applied at a frequency of 4 to 5 MHz. In embodiment, the ultrasound is applied at a frequency of 5 to 6 MHz. In embodiment, the ultrasound is applied at a frequency of 6 to 7 MHz. In embodiment, the ultrasound is applied at a frequency of 7 to 8 MHz. In embodiment, the ultrasound is applied at a frequency of 8 to 9 MHz. In embodiment, the ultrasound is applied at a frequency of 9 to 10 MHz.

A method is provided for increasing the efficacy of a chemotherapy in a subject comprising administering to the subject (i) an amount of low intensity focused ultrasound (LOFU) and (ii) an amount of a chemotherapeutic drug, wherein the chemotherapeutic drug effects endoplasmic reticulum (ER) stress and/or unfolded protein response (UPR) in a tumor cell, wherein the amounts (i) and (ii) together are sufficient to increase the efficacy of the chemotherapy.

Also provided is a method of increasing the efficacy of a chemotherapy in a predetermined volume of tissue in a subject which volume is less than the whole subject, comprising (i) administering to the subject an amount of a chemotherapeutic drug, wherein the chemotherapeutic drug effects endoplasmic reticulum (ER) stress and/or unfolded protein response (UPR) in a tumor cell and (ii) administering to the predetermined volume of tissue in a subject an amount of low intensity focused ultrasound (LOFU), wherein the amounts of (i) and (ii) together are sufficient to increase efficacy of the chemotherapy within the predetermined volume of tissue.

Also provided is a method of treating a tumor in a subject, wherein the tumor is resistant to a chemotherapeutic drug, comprising:
  receiving identification of the subject as having a tumor resistant to a specified chemotherapeutic drug;
  administering (i) an amount of low intensity focused ultrasound (LOFU) and (ii) an amount of the specified chemotherapeutic drug,
  wherein the amounts (i) and (ii) together are sufficient to treat the tumor.

Also provided is a method of treating a chemoresistant tumor in a subject, wherein the tumor has become chemoresistant to a previously administered chemotherapeutic drug, comprising:
  administering to the subject (i) an amount of low intensity focused ultrasound (LOFU) and (ii) an amount of the chemotherapeutic drug,
  wherein the amounts (i) and (ii) together are sufficient to treat the chemoresistant tumor.

In an embodiment of the methods, the chemotherapeutic drug effects endoplasmic reticulum (ER) stress and/or unfolded protein response (UPR) in a tumor cell.

In an embodiment of the methods, the chemotherapeutic drug has previously been administered to the subject a plurality of times and wherein the tumor has been diagnosed as resistant to the chemotherapeutic drug subsequent to an initial administration of the chemotherapeutic drug.

In an embodiment of the methods involving chemoresistance, the methods can further comprising receiving identification of the subject as having the tumor chemoresistant to a previously administered chemotherapeutic drug.

In an embodiment of the methods, the chemotherapeutic drug effects UPR in a tumor cell.

In an embodiment of the methods, the chemotherapeutic drug effects effects ER stress in a tumor cell.

In an embodiment of the methods, the amounts of (i) and (ii) together are sufficient to induce apoptosis of tumor cells or increase apoptosis of tumor cells.

In an embodiment of the methods, the amount of administered chemotherapeutic drug alone, in the absence of increasing the efficacy, is a sub-therapeutic dose with regard to treating a tumor.

In an embodiment of the methods, the LOFU administered is directed at a location of the tumor in the subject.

In an embodiment of the methods, the low intensity focused ultrasound (LOFU) is administered to the subject prior to, or concurrent with, the chemotherapy or the radiotherapy or the immunotherapy. In an embodiment of the methods, the LOFU is administered to the subject prior to the radiotherapy being administered. In an embodiment of the methods, the LOFU is administered to the subject prior to the chemotherapy being administered. In an embodiment of the methods, the LOFU is administered to the subject prior to the immunotherapy being administered. In an embodiment of the methods, the LOFU is administered to the subject concurrent with the radiotherapy being administered. In an embodiment of the methods, the LOFU is administered to the subject concurrent with the chemotherapy being administered. In an embodiment of the methods, the LOFU is administered to the subject concurrent with the immunotherapy being administered.

In an embodiment of the methods, the chemotherapeutic drug is an HSP90 inhibitor. In an embodiment the HSP90 inhibitor is 17AAG (tanespimycin or 17-N-allylamino-17-demethoxygeldanamycinan). In an embodiment, the chemotherapy drug is an HSP90 inhibitor. An example of an HSP90 inhibitor is 17AAG (tanespimycin or 17-N-allylamino-17-demethoxygeldanamycinan). In an embodiment, the chemotherapy drug is an alkylating agent. In an embodiment, the chemotherapy drug is trabectidin. In an embodiment, the chemotherapy drug is a mustard gas derivative. In an embodiment, the chemotherapy drug is a metal salt. In an embodiment, the chemotherapy drug is a plant alkaloid. In an embodiment, the chemotherapy drug is a antitumor antibiotic. In an embodiment, the chemotherapy drug is an antimetabolite. In an embodiment, the chemotherapy drug is a topoisomerase inhibitor. In an embodiment, the chemotherapy drug is a protesomal inhibitor. In an embodiment, the chemotherapy drug is a chemotherapeutic NSAID. In an embodiment, the chemotherapy drug is one of the miscellaneous antineoplastics listed hereinbelow.

In an embodiment of the methods, the LOFU is delivered via an ultrasound beam from an ultrasound machine comprising a transducer and the machine and subject are positioned such that at least a portion of the tumor is positioned at the focus of the transducer. In an embodiment of the methods, the LOFU is delivered to at least a portion of the tumor and the position of the tumor in the subject is monitored via an imaging technique. In an embodiment of the methods, the imaging technique is magnetic resonance imaging. In an embodiment of the methods, the imaging technique is computed tomography. In an embodiment of the methods, the imaging technique is ultrasound imaging.

In an embodiment of the methods, the LOFU is administered to multiple volumes within the tumor at least once over a period of time of less than one hour.

In an embodiment of the methods, the LOFU is non-ablative. In an embodiment of the methods, the LOFU does not cause cavitation in the tissue it is administered to.

In an embodiment of the methods, an ultrasound component of the LOFU is administered at a frequency of from 0.5 MHz to 1.5 MHz. In an embodiment of the methods, the LOFU is administered for 1 to 3 seconds. In an embodiment of the methods, the LOFU is administered by an ultrasound beam such that in the treatment zone in situ intensity is from 250 W/cm$^2$ to 750 W/cm$^2$ at 1 mm to 75 mm tissue depth in the subject.

In an embodiment of the methods, the LOFU is administered over the entire tumor volume. In an embodiment of the methods, the method delivers energy in the range of 300 to 3000 joules per cc of tumor to the tumor. In an embodiment of the methods, high intensity focused ultrasound (HIFU) is not administered to the subject. In an embodiment, HIFU is focused ultrasound that effects a tissue temperatures in the focal zone of about 80° C. or above. HIFU causes increase temperature up to 60 to 85° C. for few seconds of exposure time to solid tissue and/or causes thermal ablation in the tissue. Thermal ablation is usually achieved with power intensity of greater than 1 kW/cm$^2$ with reported frequency of 0.8 to 7 MHz. On the other hand, LOFU can be achieved with power intensity of, for example, 1 to 3 W/cm$^2$ and frequency of 0.5 to 3 MHz (see other LOFU ranges herein, however). LOFU can be continuous (100% DC) or pulsed (<100% DC, some literatures referred to as low intensity pulsed ultrasound or LIPUS) focused ultrasound by adjusting the duty cycle. Continuous LOFU at 1 MHz and 1 W/cm$^2$ for 10 minutes can produce a 0.1° C. elevation in tissue. In-vivo experiments on muscle tissue show that sonication at 1 MHz frequency increases temperature at a rate of 0.04° C./min at 0.5 W/cm$^2$; 0.16° C./min at 1.0 W/cm$^2$; 0.33° C./min at 1.5 W/cm$^2$; 0.38° C./min at 2.0 W/cm$^2$.

In an embodiment of the methods, the effect of the amount of radiotherapy and the amount of LOFU is synergistic in treating the tumor.

In an embodiment of the methods, the subject is human.

In an embodiment of the methods, the tumor is a tumor of the prostate, breast, nasopharynx, pharynx, lung, bone, brain, sialaden, stomach, esophagus, testes, ovary, uterus, endometrium, liver, small intestine, appendix, colon, rectum, bladder, gall bladder, pancreas, kidney, urinary bladder, cervix, vagina, vulva, prostate, thyroid or skin, head or neck, glioma or soft tissue sarcoma. In an embodiment of the methods, the tumor is a prostate cancer.

In an embodiment of the methods, the metastasis is a lung metastasis.

In an embodiment of the methods, the LOFU is administered with a device comprising:

a control system that generates a frequency waveform; and one or more transducers configured to produce ultrasound based on a frequency waveform between 1 and 1000 W/cm$^2$ spatial peak temporal average acoustic output intensity ($I_{spta}$) in a treatment zone, wherein ultrasound is applied continuously to the treatment zone for a time in the range of from 0.5 to 5 seconds, wherein ultrasound frequency is in the range of 0.01 to 10 MHz and wherein mechanical index of any beam is less than 4.

In an embodiment of the methods, each of the one or more transducers are configured to produce ultrasonic beams based on the frequency waveform with central frequencies in the range of 0.05 to 5 MHz and an acoustic output intensity of between 20 and 1000 W/cm$^2$. In an embodiment of the methods, each of the one or more transducers are configured to produce ultrasonic beams based on the frequency waveform with central frequencies in the range of 0.5 to 1.5 MHz and an acoustic output intensity of between 20 and 1000 W/cm$^2$. In an embodiment of the methods, each transducer is configured to produce columnated ultrasound such that the beam profile waist at −3 dB is not less than 5 mm in a treatment zone. In an embodiment of the methods, one or more beams are mechanically moved during treatment. In an embodiment of the methods, the one or more transducers comprise two or more transducers configured to operate sequentially or simultaneously and produce ultrasound of average spatial peak 250 W/cm² in a treatment zone during a treatment period. In an embodiment of the methods, the one or more transducers are configured produce ultrasound having a frequency within the range of 10 kHz to 300 kHz. In an embodiment of the methods, the one or more transducers are configured produce ultrasound having a frequency within the range of 300 kHz to 3 MHz. In an embodiment of the methods, one or more transducers operate at a frequency of 300 kHz to 3 MHz and one or more transducers operates at a frequency of between 30 and 300 kHz. In an embodiment of the methods, two or more ultrasound transducers generate ultrasound beams that pass through a treatment zone, with each beam having an $I_{spta}$ in the intersection zone in the range of 10 to 500 W/cm². In an embodiment of the methods, the treatment time is less than 5 seconds per cubic centimeter of tumor. In an embodiment of the methods, two transducers generate ultrasound beams that intersect within a treatment zone, with each beam having an $I_{spta}$ in the intersection zone in the range of 50 to 500 W/cm². In an embodiment of the methods, three transducers generate ultrasound beams that pass through a treatment zone, with each beam having an $I_{spta}$ in the intersection zone in the range of 50 to 500 W/cm². In an embodiment of the methods, the one or more transducers produce ultrasonic beams that are substantially in phase with one another within the treatment zone. In an embodiment of the methods, two ultrasound beams emanating from separate ultrasound transducers are substantially in phase and intersect within a treatment zone, and each beam has an acoustic power spatial peak intensity in the intersection zone in the range of 70 to 100 W/cm² and the ultrasound is applied continuously from 1 to 5 seconds.

In an embodiment of the methods, three ultrasound beams emanating from separate ultrasound transducers are substantially in phase and intersect within a treatment zone, and each beam has an acoustic power spatial peak intensity in the intersection zone in the range of 50 to 70 W/cm² and the ultrasound is applied continuously for 1 to 5 seconds. In an embodiment of the methods, ultrasonic beams originating from separate transducers each produce an $I_{spta}$ in the range of approximately 100 to 1000 W/cm² in the treatment zone. In an embodiment of the methods, at least one transducer generates an ultrasonic beam with a high intensity diameter that is substantially larger in size than the treatment zone and is directed such that the treatment zone is entirely within the beam. In an embodiment of the methods, an intense treatment zone is formed where two or more ultrasound beams cross paths, the intense treatment zone being equal to or greater than about 1 cm perpendicular to the transmitted energy direction and also equal to or greater than about 1 cm parallel to the transmitted direction. In an embodiment of the methods, acoustic pressure applied to a treatment zone from each transducer is 0.1 to 10 MPa. In an embodiment of the methods, the number of transducers that provide the intense ultrasound treatment zone is between 1 and 1000. In an embodiment of the methods, the ultrasound from the one or more transducers is applied continuously during the treatment time. In an embodiment of the methods, the ultrasound is produced with a duty cycle in the range of 1 on time units to 9 off time units. In an embodiment of the methods, the transducers are configured to produce ultrasound in single frequency tones or multi-frequency chirps. In an embodiment of the methods, the one or more transducers are operated sequentially in time. In an embodiment of the methods, the total energy delivered to the target tissue and desired margin around the target tissue for the entire course of the application is greater than that to surrounding tissues. In an embodiment of the methods, the one or more transducers are configured so that the frequency of ultrasound is swept during application. In an embodiment of the methods, the one or more transducers comprise two-dimensional phased arrays, In an embodiment of the methods, the one or more transducers comprise annular arrays. In an embodiment of the methods, the one or more transducers comprise three-dimensional phased arrays. In an embodiment of the methods, the one or more transducers are incorporated into one or more endoscopic devices. In an embodiment of the methods, the one or more transducers are incorporated into a magnetic resonance imaging machine.

In an embodiment of the methods, the one or more transducers are incorporated into a radiotherapy treatment machine.

In an embodiment of the methods, the one or more transducers are configured to produce ultrasound so that the maximum temperature reached in the treatment zone is less than 45° C. during a treatment where ultrasound is applied to the treatment zone for about 2 seconds or less.

In an embodiment of the methods, the one or more transducers are configured to produce ultrasound so that the maximum temperature reached in the treatment zone is less than 50° C. during a treatment where ultrasound is applied to the treatment zone for about 2 seconds or less.

In an embodiment of the methods, the one or more transducers are configured to produce ultrasound so that the maximum temperature reached in the treatment zone is less than 55° C. during a treatment where ultrasound is applied to the treatment zone for about 2 seconds or less.

In an embodiment of the methods, the LOFU and radiotherapy are administered by a system comprising:
    a LOFU device comprising:
    a control system that generates a frequency waveform; and
    one or more transducers configured to produce ultrasound based on a frequency waveform between 1 and 1000 W/cm² spatial peak temporal average acoustic output intensity ($I_{spta}$) in a treatment zone, wherein the ultrasound is applied continuously for a time in the range of from 0.5 to 5 seconds, and wherein ultrasound frequency is in the range of 0.01 to 10 MHz;
    a radiotherapy treatment machine; and
    a control system operatively configured to control the LOFU device and the radiotherapy treatment machine so that a first amount of the ultrasound and a second amount of radiotherapy are administered to a subject, wherein the first and second amounts together are sufficient to treat a tumor in the subject.

A method of treating a tumor in a subject is provided comprising administering to the subject (i) an amount of low intensity focused ultrasound (LOFU) and (ii) an amount of chemotherapy or an amount of radiotherapy or an amount of immunotherapy, wherein the amounts of (i) and (ii) together are sufficient to treat a tumor.

In an embodiment of the method, the amount of LOFU and the amount of radiotherapy are administered to the subject. In another embodiment of the method, the amount of LOFU and the amount of radiotherapy are administered to the subject. In another embodiment of the method, the amount of LOFU and the amount of immunotherapy are administered to the subject.

A method of treating a tumor in a subject is provided comprising administering to the subject (i) an amount of low intensity focused ultrasound (LOFU) and (ii) an amount of a targeted anti-cancer therapy wherein the amounts of (i) and (ii) together are sufficient to treat a tumor. In an embodiment, the targeted therapy comprises a mAb directed to Her2 or VEGFR. In an embodiment, the targeted therapy comprises a tyrosine kinase inhibitor.

Also provided is a method of inhibiting metastasis of a tumor in a subject, comprising administering to a subject having a tumor an amount of low intensity focused ultrasound (LOFU) and an amount of a radiotherapy, wherein the amounts together are sufficient to inhibit metastasis of a tumor in a subject.

In the methods, the radiotherapy can be ablative hypofractionated radiation therapy.

Preferably, in the methods the LOFU is directed at a location of the tumor in the subject.

Also provided is a method of reducing the effective dose of an anti-cancer chemotherapy required to treat a tumor in a subject comprising administering to the subject undergoing the anti-cancer chemotherapy an amount of low intensity focused ultrasound (LOFU) sufficient to reduce the effective dose of the anti-cancer chemotherapy required to treat a tumor.

In an embodiment of each of the methods, the LOFU is administered to the subject prior to, or concurrent with, the chemotherapy or the radiotherapy or the immunotherapy.

In an embodiment the LOFU is administered to the subject prior to the radiotherapy being administered.

In the methods wherein an anti-cancer chemotherapy is administered, in an embodiment the anti-cancer chemotherapy comprises administration of an HSP90 inhibitor to the subject. The HSP90 inhibitor can be 17AAG (tanespimycin or 17-N-allylamino-17-demethoxygeldanamycinan). In an embodiment, the chemotherapy drug is an alkylating agent. In an embodiment, the chemotherapy drug is trabectidin. In an embodiment, the chemotherapy drug is a mustard gas derivative. In an embodiment, the chemotherapy drug is a metal salt. In an embodiment, the chemotherapy drug is a plant alkaloid. In an embodiment, the chemotherapy drug is a antitumor antibiotic. In an embodiment, the chemotherapy drug is an antimetabolite. In an embodiment, the chemotherapy drug is a topoisomerase inhibitor. In an embodiment, the chemotherapy drug is a protesomal inhibitor. In an embodiment, the chemotherapy drug is a chemotherapeutic NSAID. In an embodiment, the chemotherapy drug is one of the miscellaneous antineoplastics listed hereinbelow.

In an embodiment of the methods, the LOFU is delivered via an ultrasound beam from an ultrasound machine comprising a transducer and the machine and subject are positioned such that the at least a portion of the tumor is positioned at the focal length of the transducer.

In an embodiment of the methods, the LOFU is delivered to at least a portion of the tumor and the position of the tumor is monitored via an imaging technique. Magnetic resonance imaging can be such an imaging technique.

In the methods, the LOFU can be administered to multiple points within the tumor at least once over a period of time of less than one hour.

In an embodiment of the methods, the LOFU is non-ablative.

In an embodiment of the methods, the LOFU is administered at a frequency of from 0.5 MHz to 1.5 MHz.

In an embodiment of the methods, the LOFU is administered for 1.5-3 seconds

In an embodiment of the methods, the LOFU is administered by an ultrasound beam such that at the focus of the ultrasound beam the in situ intensity is from 250 W/cm² to 750 W/cm². In an embodiment of the methods, the LOFU is administered by an ultrasound beam such that at the focus of the ultrasound beam the in situ intensity is from 250 W/cm² to 750 W/cm² at 1 mm to 75 mm tissue depth in the subject. In an embodiment of the methods, the LOFU is administered by an ultrasound beam such that at the focus of the ultrasound beam the in situ intensity is from 350 W/cm² to 650 W/cm² at 1 mm to 75 mm tissue depth in the subject. In an embodiment of the methods, the LOFU is administered by an ultrasound beam such that at the focus of the ultrasound beam the in situ intensity is from 450 W/cm² to 550 W/cm² at 1 mm to 75 mm tissue depth in the subject.

The LOFU can be administered over the entire tumor volume, or can be administered over a portion of the tumor volume. In a preferred embodiment the LOFU is administered over the entire tumor volume.

In an embodiment, of the method the LOFU delivers at least 500 to 5000 joules of energy per cc of tumor tissue through the tumor. In an embodiment, of the method the LOFU delivers at least 1000 to 4000 joules of energy per cc of tumor tissue. In an embodiment, of the method the LOFU delivers at least 2000 to 3000 joules of energy per cc of tumor tissue through the tumor.

In an embodiment, high intensity focused ultrasound (HIFU) is not administered to the subject. In an embodiment, high intensity focused ultrasound has not been administered to the subject. In an embodiment, high intensity focused ultrasound has not been administered to the tumor. In an embodiment where LOFU is administered to the subject before the anti-cancer therapy, high intensity focused ultrasound is not administered to the subject after the LOFU is administered and before the anti-cancer therapy is administered.

In an embodiment, the anti-cancer therapeutic effect of the amount of radiotherapy and the amount of LOFU is synergistic.

In an embodiment, the LOFU adminstered raises the tissue/tumor temperature to between 40° C.-45° C. In an embodiment, the LOFU adminstered raises the tissue/tumor temperature to no more than 40° C. In an embodiment, the LOFU adminstered raises the tissue/tumor temperature to no more than 45° C. In an embodiment, the LOFU adminstered raises the tissue/tumor temperature to no more than 50° C. HIFU will generally raise tissue temperatures more than this.

In an embodiment, the LOFU is administered for 0.5 to 3 seconds. In an embodiment, the LOFU is administered for 1.5 to 3 seconds. In an embodiment, the LOFU is administered with a 100% duty cycle. In an embodiment, the LOFU is administered with one of the separate embodiments of a 10, 20, 30, 40, 50, 60, 70, 80 or 90% duty cycle.

Also provided is a method of sensitizing a tumor in a subject to an amount of an anti-cancer therapy the method comprising administering to the subject, prior to, during or after the anti-cancer therapy, an amount of low intensity focused ultrasound (LOFU) effective to sensitize a tumor in a subject to an amount of an anti-cancer therapy. In an embodiment, the anti-cancer therapy comprises a chemotherapy, or a radiotherapy, or an immunotherapy, or a targeted therapy, or a surgery. In an embodiment, the anti-cancer therapy comprises a chemotherapy. In an embodiment, the anti-cancer therapy comprises an immunotherapy. In an embodiment, the anti-cancer therapy comprises a radiotherapy. In an embodiment, the anti-cancer therapy comprises surgery, for example, to excise the tumor. The method can further comprise administering the anti-cancer therapy to the subject. Sensitizing a tumor to an amount of an anti-cancer therapy makes the tumor more susceptible to the treatment. For example, a parameter by which tumor treatment may be measured, such as tumor volume reduction, is greater for a given amount of an anti-cancer therapy applied to the sensitized tumor as compared to the same amount of an anti-cancer therapy applied to a non-sensitized tumor of equivalent mass, vascularity, position and type in the same or an equivalent subject. In an embodiment, the amount of LOFU effective to sensitize a tumor in a subject to an amount of an anti-cancer therapy and the anti-cancer therapy are synergistic in effect.

In any of the methods described herein, the subject is a mammal. In an embodiment, the subject is a human.

The tumor referred to in the methods can be a tumor of the prostate, breast, nasopharynx, pharynx, lung, bone, brain, sialaden, stomach, esophagus, testes, ovary, uterus, endometrium, liver, small intestine, appendix, colon, rectum, bladder, gall bladder, pancreas, kidney, urinary bladder, cervix, vagina, vulva, prostate, thyroid or skin, head or neck, or is a glioma or a soft tissue sarcoma. In one embodiment, the tumor is a prostate cancer. In one embodiment, the tumor is a soft tissue sarcoma. In an embodiment the primary tumor is treated. In an embodiment the secondary tumor is treated. In an embodiment, treatment of the tumor reduces the likelihood of a secondary tumor. In one embodiment, the metastasis comprises one or more lung metastases.

The term "tumor," as used herein, and unless otherwise specified, refers to a neoplastic cell growth, and includes pre-cancerous and cancerous cells and tissues. Tumors usually present as a lesion or lump. In an embodiment, the tumor is a malignant neoplasm.

As used herein "metastasize" (or grammatical equivalent) means, in regard to a cancer or tumor, the spread of the cancer or tumor from one organ or tissue of a subject to another organ or tissue of the subject spatially apart from the first organ or tissue.

As used herein, "treating" a tumor means that one or more symptoms of the disease, such as the tumor itself, vascularization of the tumor, or other parameters by which the disease is characterized, are reduced, ameliorated, inhibited, placed in a state of remission, or maintained in a state of remission. "Treating" a tumor also means that one or more hallmarks of the tumor may be eliminated, reduced or prevented by the treatment. Non-limiting examples of such hallmarks include uncontrolled degradation of the basement membrane and proximal extracellular matrix, migration, division, and organization of the endothelial cells into new functioning capillaries, and the persistence of such functioning capillaries. In an embodiment, treating the tumor means reducing the size or volume of the tumor.

As used herein, "inhibiting metastasis" of a tumor in a subject means that one or more symptoms or one or more other parameters by which the disease is characterized, are reduced, ameliorated, or inhibited. Non-limiting examples of such parameters include uncontrolled degradation of the basement membrane and proximal extracellular matrix, and travel of tumor cells through the bloodstream or lymphatics, invasion, dysregulated adhesion, and proliferation at secondary site, either distal or local. In an embodiment, treating the metastasis means reducing the development or inhibiting the development of metastases.

Radiotherapy is well-known in the art. Radiotherapy as encompassed herein includes medically therapeutic radiation delivered by a machine outside the body (external-beam radiation therapy), or from radioactive material placed in the body near cancer cells (internal radiation therapy, also called brachytherapy) or systemic radiation therapy. Radiotherapy as encompassed herein includes 3-dimensional conformal radiation therapy (3D-CRT), intensity-modulated radiation therapy (IMRT), image-guided radiation therapy (IGRT), and tomotherapy. The radiotherapy may also be part of a stereotactic radiosurgery or stereotactic body radiation therapy (SBRT). Delivery by any particle beam known in the art is encompassed also, for example proton therapy, carbon ion therapy, or other charged particle beams depending on tumor type and location.

In an embodiment, the radiotherapy is CT image guided. In an embodiment, the radiotherapy is hypofractionated cone beam radiotherapy. In an embodiment, the radiotherapy is hypofractionated cone beam CT image guided radiotherapy. All combinations of the various elements described herein are within the scope of the invention unless otherwise indicated herein or otherwise clearly contradicted by context.

Chemotherapeutic drugs which may be used in the invention are various. Examples of chemotherapeutic drugs include:

alkylating agents (e.g. trabectidin ((1'R,6R,6aR,7R,13S,14S,16R)-6',8,14-trihydroxy-7',9-dimethoxy-4,10,23-trimethyl-19-oxo-3',4',6,7,12,13,14,16-octahydrospiro [6,16-(epithiopropano-oxymethano)-7,13-imino-6aH-1,3-dioxolo[7,8]isoquino[3,2-b][3]benzazocine-20,1' (2'H)-isoquinolin]-5-yl acetate));

mustard gas derivatives (e.g. mechlorethamine, cyclophosphamide, chlorambucil, melphalan, and ifosfamide);

ethylenimines (e.g. thiotepa and hexamethylmelamine);

alkylsulfonates (e.g. busulfan);

hydrazines and triazines (e.g. altretamine, procarbazine, dacarbazine and temozolomide); nitrosureas (e.g. carmustine, lomustine and streptozocin);

metal salts (e.g. carboplatin, cisplatin, and oxaliplatin);

plant alkaloids (e.g. vinca alkaloids such as vincristine, vinblastine and vinorelbine, taxanes such as paclitaxel and docetaxel, podophyllotoxins such as etoposide and tenisopide, camptothecan analogs (topoisomerase inhibitors) such as irinotecan and topotecan);

antitumor antibiotics (e.g. anthracyclines: doxorubicin, daunorubicin, epirubicin, mitoxantrone, and idarubicin; chromomycins: dactinomycin and plicamycin; miscellaneous ones such as mitomycin and bleomycin);

antimetabolites (e.g. folic acid antagonists: methotrexate; pyrimidine antagonists: 5-fluorouracil, foxuridine, cytarabine, capecitabine, and gemcitabine; purine antagonist: 6-mercaptopurine and 6-thioguanine; adenosine deaminase inhibitors: cladribine, fludarabine, nelarabine and pentostatin);

topoisomerase inhibitors (e.g. ironotecan, topotecan; amsacrine, etoposide, etoposide phosphate, teniposide);

protesomal inhibitors;

Chemotherapeutic NSAIDS; and miscellaneous antineoplastics (e.g. ribonucleotide reductase inhibitor: hydroxyurea; adrenocortical steroid inhibitor: mitotane; enzymes: asparaginase and pegaspargase;

antimicrotubule agent: estramustine; retinoids: bexarotene, isotretinoin, tretinoin (ATRA).

Chemotherapeutic drugs which effect endoplasmic reticulum (ER) stress and/or effect unfolded protein response (UPR) in cells are known in the art. For example, protesomal inhibitors such as e.g. Bortezomib (Velcade; previously known as PS-341), elicit an ER stress response. Also, protesomal inhibitors such as e.g. Bortezomib elicit the UPR. Histone deacetylase (HDAC) inhibitors elicit an ER stress response. Chemotherapeutic NSAIDS (e.g. indomethacin, diclofenac, and celecoxib) can elicit an ER stress response and can elicit the UPR. Estrogen receptor a inhibitors such BHPI (1, 3-dihydro-3,3-bis(4-hydroxyphenyl)-7-methyl-2H-indol-2-one) can activate the UPR. Platinum-containing anti-cancer drugs: cisplatin is known to elicit an ER stress response. The taxane family of drugs: paclitaxel is known to elicit an ER stress response. Anthracycines such as doxorubicin are known to elicit ER stress. Cyclophosphamide is known to elicit ER stress. See also Table 2 of Hetz et al., Nature Reviews, Drug Discovery, 12:703-719 (September, 2013), hereby incorporated by reference.

The endoplasmic reticulum (ER) is the site of synthesis and folding of secreted, membrane-bound and some organelle-targeted proteins. The ER is highly sensitive to stresses that perturb cellular energy levels, the redox state or $Ca^{2+}$ concentration. Such stresses reduce the protein-folding capacity of the ER, which can result in the accumulation and aggregation of unfolded proteins and/or an imbalance between the load of resident and transit proteins in the ER and the organelle's ability to process that load. This condition is referred to herein, and in the art, as "ER stress". The ER stress response can promote cellular repair and sustained survival by reducing the load of unfolded proteins through global attenuation of protein synthesis and/or upregulation of chaperones, enzymes and structural components of the ER, which enhance protein folding. This response is collectively termed as the unfolded protein response (UPR). Accumulation of unfolded proteins causes dissociation of GRP78 from PERK, ATF6 and IRE1, thereby initiating the UPR.

TABLE 1

Non-limiting examples of chemotherapies that can be used with LOFU

| Types of action | Drug name | Mechaniism of Action | Selected interactions with LOFU |
|---|---|---|---|
| Block proteosome/ degradation of misfolded protein | | | Decrease the degradation of misfolded protein that LOFU induces thereby increasing the amount of unfolded protein response to tip towards apoptosis. |
| | Bortezomib | proteosome inhibitor | ATF-4 induction by UPR can confer resistance to Bortezomib |
| | 3-methyladenine | an inhibitor of phosphatidyl inositol 3-kinase (PI3-kinase) prevented induction of ATG5 and activation of LC3-II and blocked autophagosome formation | |
| | polyphenol (green tea) epigallocatechin gallate | proteosome inhibitor | |
| | genistein | Proteosome inhibitor | |
| | curcumin | Proteosome inhibitor | |
| | resveratrol | Proteosome inhibitor/ represses XBP-1 prosurvival signaling | |
| Inhibitor of autophagy | | | During times of stress, the cells will induce autophagy to immediately replenish depleting building blocks. Inhibiting the process of autophagy in cells treated with LOFU is expected to result in cells that are not able to immediately respond to the stress and thereby inducing apoptosis. |
| | 15,16-Dihydrotanshinone I (Tanshen root) | induce UPR via proteosome inhibition | |
| | Chloroquine | inhibitor of autophagy | |
| Inducer of autophagy | | | Decreasing the unfolded protein response sparked by LOFU and marking cells less sensitive. If autophagy is activated for long enough then can push cells into pro-apoptotic state. A combination of increase |

TABLE 1-continued

Non-limiting examples of chemotherapies that can be used with LOFU

| Types of action | Drug name | Mechaniism of Action | Selected interactions with LOFU |
|---|---|---|---|
| | | | macroautophagy plus increased UPR can provide an immunological response. |
| | repamycin | mTOR inhibitor | |
| | temsirolimus | mTOR inhibitor | |
| | 4-O-carboxymethyl asochlorin | agonist of the nuclear hormone receptor PPARγ; ER stress-induced autophagy and apoptosis | |
| ER stress inducer | | | Combining two different sources of UPR inducing agents can provide an addictive effect to cancer killing. |
| | Celecoxib | Cox-2 inhibitor - by causing leakage of calcium from ER into cytosol | |
| | Verapamil | Ca channel inhibitor | Enhancing ER stress signaling |
| | Ritonavir | inhibits protein degradation that's synergistic with proteosome inhibitor | |
| | 3-thia fatty acid tetradecylthioacetic acid | Inducer of ER stress | |
| | Nelfinavir | modulates CHOP expression | |
| Damage DNA structure/prevents DNA synthesis | | | Inhibiting the repair mechanism to prevent cellular repair after LOFU damage. |
| | cisplatin | induce ER stress and dmg DNA | |
| | gemcitabine | Nucleoside analog | |
| Block protein synthesis | | | |
| | salubrinal | inhibitor of eIF2a phosphotase | |
| | Cycloheximide | | |
| Increase death signaling | | | |
| | TRAIL | | |
| chemical chaperones | | | |
| | 4-phenylbutyric acid | chemical chaperone which rescue the mutant alpha1-antitrypsin phenotype | |
| chaperones inhibitor | | | |
| | geldanamycin | HSP90 inhibitor | |
| | 17-allyamino-17-demethoxy-geldanamycin (17AAG) | HSP90 inhibitor | |
| | 17-dimethylamino-ethylamino-17-demethoxygelana-mycin (17DMAG) | HSP90 inhibitor | |
| blocking sonoporation repair | | | |
| | vacuolin | a newly discovered small organic molecule that blocks the wounding- and Ca2+- | |

TABLE 1-continued

Non-limiting examples of chemotherapies that can be used with LOFU

| Types of action | Drug name | Mechaniism of Action | Selected interactions with LOFU |
|---|---|---|---|
| | | triggered fusion of lysosomes with the plasma membrane | |

In an embodiment of the methods, the chemotherapy drug is an HSP90 inhibitor. An example of an HSP90 inhibitor is 17AAG (tanespimycin or 17-N-allylamino-17-demethoxygeldanamycinan). In an embodiment, the chemotherapy drug is an alkylating agent. In an embodiment, the chemotherapy drug is trabectidin. In an embodiment, the chemotherapy drug is a mustard gas derivative. In an embodiment, the chemotherapy drug is a metal salt. In an embodiment, the chemotherapy drug is a plant alkaloid. In an embodiment, the chemotherapy drug is an antitumor antibiotic. In an embodiment, the chemotherapy drug is an antimetabolite. In an embodiment, the chemotherapy drug is a topoisomerase inhibitor. In an embodiment, the chemotherapy drug is a protesomal inhibitor. In an embodiment, the chemotherapy drug is a chemotherapeutic NSAID. In an embodiment, the chemotherapy drug is one of the miscellaneous antineoplastics listed hereinabove.

Other non-limiting examples of chemotherapy drugs or agents encompassed by the invention, unless otherwise stated, include anthracyclines, maytansinoids, alkylating agents, anti-metabolites, plant alkaloids or terpenoids, and cytotoxic antibiotics. In embodiments, the chemotherapy agent is cyclophosphamide, bleomycin, etoposide, platinum agent (cisplatin), fluorouracil, vincristine, methotrexate, taxol, epirubicin, leucovorin (folinic acid), or irinotecan.

Anti-tumor immunotherapies encompassed herein (i) include monoclonal antibodies (including naked, chemo-, radio- or toxin-conjugated antibodies and also bispecific antibodies), relevant antigen-binding fragments thereof such as fragments comprised of Fab or scFv fragments, that that bind with high affinity to cancer-associated biomolecular targets; (ii) those that are non-specific with respect to tumor cells and tumor cell antigens; anti-tumor immunotherapies e.g. cytokines, interleukins, interferons, GM-CSF, small organic molecules (e.g. 1,500 daltons or less) or other drugs that bind to cytokines or cytokine receptors; and materials that target checkpoints including but not limited to one of CTLA-4, PD-1, PDL-1, and other small organic molecules, peptides and aptamers that target immune responses. In an embodiment, immunotherapy as used herein excludes bacteria-based anticancer or anti-tumor immunotherapies. In one embodiment, immunotherapy as used herein excludes Listeria-based immunotherapies.

In an embodiment, increasing efficacy of a treatment means an increase in the extent of therapeutic effect achieved versus the extent achieved for the same amount of treatment (e.g. a given treatment dose) in the absence of the efficacy-increasing method being applied.

Also provided is an acoustic priming therapy device comprising:
 a control system that generates a frequency waveform; and
 one or more transducers configured to produce ultrasound based on a frequency waveform between 1 and 1000 W/cm$^2$ spatial peak temporal average acoustic output intensity ($I_{spta}$) in a treatment zone, wherein ultrasound is applied continuously to the treatment zone for a time in the range of from 0.5 to 5 seconds, wherein ultrasound frequency is in the range of 0.01 to 10 MHz and wherein mechanical index of any beam is less than 4.

In an embodiment of the device, each of the one or more transducers are configured to produce ultrasonic beams based on the frequency waveform with central frequencies in the range of 0.05 to 5 MHz and an acoustic output intensity of between 20 and 1000 W/cm$^2$.

In an embodiment of the device, each of the one or more transducers are configured to produce ultrasonic beams based on the frequency waveform with central frequencies in the range of 0.5 to 1.5 MHz and an acoustic output intensity of between 20 and 1000 W/cm$^2$.

In an embodiment of the device, each transducer is configured to produce columnated ultrasound such that the beam profile waist at −3 dB is not less than 5 mm in a treatment zone.

In an embodiment of the device, one or more beams are mechanically moved during treatment.

In an embodiment of the device, the one or more transducers comprise two or more transducers configured to operate sequentially or simultaneously and produce ultrasound of average spatial peak 250 W/cm$^2$ in a treatment zone during a treatment period.

In an embodiment of the device, the one or more transducers are configured produce ultrasound having a frequency within the range of 10 kHz to 300 kHz.

In an embodiment of the device, the one or more transducers are configured produce ultrasound having a frequency within the range of 300 kHz to 3 MHz.

In an embodiment of the device, one or more transducers operate at a frequency of 300 kHz to 3 MHz and one or more transducers operates at a frequency of between 30 and 300 kHz In an embodiment of the device, two or more ultrasound transducers generate ultrasound beams that pass through a treatment zone, with each beam having an $I_{spta}$ in the intersection zone in the range of 10 to 500 W/cm$^2$ In an embodiment of the device, the treatment time is less than 5 seconds per cubic centimeter of tumor.

In an embodiment of the device, two transducers generate ultrasound beams that intersect within a treatment zone, with each beam having an $I_{spta}$ in the intersection zone in the range of 50 to 500 W/cm$^2$.

In an embodiment of the device, three transducers generate ultrasound beams that pass through a treatment zone, with each beam having an $I_{spta}$ in the intersection zone in the range of 50 to 500 W/cm$^2$.

In an embodiment of the device, the one or more transducers produce ultrasonic beams that are substantially in phase with one another within the treatment zone.

In an embodiment of the device, two ultrasound beams emanating from separate ultrasound transducers are substantially in phase and intersect within a treatment zone, and each beam has an acoustic power spatial peak intensity in the intersection zone in the range of 70 to 100 W/cm² and the ultrasound is applied continuously from 1 to 5 seconds.

In an embodiment of the device, three ultrasound beams emanating from separate ultrasound transducers are substantially in phase and intersect within a treatment zone, and each beam has an acoustic power spatial peak intensity in the intersection zone in the range of 50 to 70 W/cm² and the ultrasound is applied continuously for 1 to 5 seconds.

In an embodiment of the device, ultrasonic beams originating from separate transducers each produce an $I_{spta}$ in the range of approximately 100 to 1000 W/cm² in the treatment zone.

In an embodiment of the device, at least one transducer generates an ultrasonic beam with a high intensity diameter that is substantially larger in size than the treatment zone and is directed such that the treatment zone is entirely within the beam.

In an embodiment of the device, an intense treatment zone is formed where two or more ultrasound beams cross paths, the intense treatment zone being equal to or greater than about 1 cm perpendicular to the transmitted energy direction and also equal to or greater than about 1 cm parallel to the transmitted direction.

In an embodiment of the device, acoustic pressure applied to a treatment zone from each transducer is 0.1 to 10 MPa.

In an embodiment of the device, the number of transducers that provide the intense ultrasound treatment zone is between 1 and 1000.

In an embodiment of the device, the ultrasound from the one or more transducers is applied continuously during the treatment time.

In an embodiment of the device, the ultrasound is produced with a duty cycle in the range of 1 on time units to 0 to 9 off time units.

In an embodiment of the device, the transducers are configured to produce ultrasound in single frequency tones or multi-frequency chirps.

In an embodiment of the device, the one or more transducers are operated sequentially in time.

In an embodiment of the device, the total energy delivered to the target tissue and desired margin around the target tissue for the entire course of the application is greater than that to surrounding tissues. In an embodiment of the device, the one or more transducers are configured so that the frequency of ultrasound is swept during application. In an embodiment of the device, the one or more transducers comprise two-dimensional phased arrays. In an embodiment of the device, the one or more transducers comprise annular arrays. In an embodiment of the device, the one or more transducers comprise three-dimensional phased arrays. In an embodiment of the device, the one or more transducers are incorporated into one or more endoscopic devices. In an embodiment of the device, the one or more transducers are incorporated into a magnetic resonance imaging machine. In an embodiment of the device, the one or more transducers are incorporated into a radiotherapy treatment machine.

In an embodiment of the device, the one or more transducers are configured to produce ultrasound so that the maximum temperature reached in the treatment zone is less than 45° C. during a treatment where ultrasound is applied to the treatment zone for about 2 seconds or less. In an embodiment of the device, the one or more transducers are configured to produce ultrasound so that the maximum temperature reached in the treatment zone is less than 50° C. during a treatment where ultrasound is applied to the treatment zone for about 2 seconds or less.

In an embodiment of the device, the one or more transducers are configured to produce ultrasound so that the maximum temperature reached in the treatment zone is less than 55° C. during a treatment where ultrasound is applied to the treatment zone for about 2 seconds or less.

Also provided is a system comprising:
an acoustic priming therapy device comprising:
a control system that generates a frequency waveform; and
one or more transducers configured to produce ultrasound based on a frequency waveform between 1 and 1000 W/cm² spatial peak temporal average acoustic output intensity ($I_{spta}$) in a treatment zone, wherein the ultrasound is applied continuously for a time in the range of from 0.5 to 5 seconds, and wherein ultrasound frequency is in the range of 0.01 to 10 MHz;
a radiotherapy treatment machine; and
a control system operatively configured to control the acoustic priming therapy device and the radiotherapy treatment machine so that a first amount of the ultrasound and a second amount of radiotherapy are administered to a subject, wherein the first and second amounts together are sufficient to treat a tumor in the subject.

Also provided is a system comprising:
an acoustic priming therapy device comprising:
a control system that generates a frequency waveform; and
one or more transducers configured to produce ultrasound based on a frequency waveform between 1 and 1000 W/cm² spatial peak temporal average acoustic output intensity ($I_{spta}$) in a treatment zone, wherein the ultrasound is applied continuously for a time in the range of from 0.5 to 5 seconds, and wherein ultrasound frequency is in the range of 0.01 to 10 MHz;
the acoustic priming therapy device for use in combination with chemotherapy so that a first amount of the ultrasound and a second amount of the chemotherapy are administered to a subject, wherein the first and second amounts together are sufficient to treat a tumor in the subject.

Also provided is a system comprising:
an acoustic priming therapy device comprising:
a control system that generates a frequency waveform; and
one or more transducers configured to produce ultrasound based on a frequency waveform between 1 and 1000 W/cm² spatial peak temporal average acoustic output intensity (Ispta) in a treatment zone, wherein the ultrasound is applied continuously for a time in the range of from 0.5 to 5 seconds, and wherein ultrasound frequency is in the range of 0.01 to 10 MHz;
the acoustic priming therapy device for use in combination with immunotherapy so that a first amount of the ultrasound and a second amount of the immunotherapy are administered to a subject, wherein the first and second amounts together are sufficient to treat a tumor in the subject.

This invention will be better understood from the examples follow. However, one skilled in the art will readily appreciate that the specific methods and results discussed are merely illustrative of the invention as described more fully in the claims that follow thereafter.

Example 1

B16 melanoma tumors suppress IL-2 and IFNγ production by tumor-specific CD4+ T cells: To determine how melanoma cells may modulate tumor induced effector CD4+ T cell responses, three different mouse models were used. First, B16-F1 melanoma tumors were induced in C57Bl/6 J mice by subcutaneous injection of B16 cells in the lumbar flanks. Tumors were allowed to grow to a size of 7-8 mm and CD4+ T cells were then isolated from both the ipsilateral inguinal draining lymph nodes (DLN) and distal-contralateral non-draining cervical lymph nodes (NDLN). T cells were also obtained from control mice that did not harbor any tumors. Supporting previous reports of tumor-antigen specific T cell tolerance in murine melanoma (18, 21), CD4+ T cells isolated from the tumor DLN produced significantly less IL-2 than cells isolated from the distal contralateral NDLN of the same mice, or from lymph nodes of control tumor-free mice, when stimulated ex vivo with anti-CD3 and anti-CD28 antibodies. A similar but less pronounced effect was also observed for IFNγ (FIGS. 1A and B).

To confirm these data, a B16-F1 melanoma cell line that had been stably transfected to express OVA as a surrogate tumor antigen was used. These cells were subcutaneously injected into OT-II mice, a mouse strain with T cells expressing a transgenic MHC class II-restricted TCR that recognizes the OVA323-339 peptide. T cells were collected from these mice as described, and stimulated ex vivo using splenocytes loaded with OVA323-339 peptide. CD4+ T cells from the ipsilateral DLN again produced significantly reduced amounts of IL-2 and IFNγ compared to cells from the contralateral NDLN or from tumor free mice (FIGS. 1C and 1D).

These results were further corroborated in a third model using Tyrp1 mice, which are deficient in tyrosinase-related protein 1 and bear T cells expressing a MHC class II-restricted TCR specific for the TRP-1113-127 peptide of this endogenous melanocyte differentiation antigen. Those mice were injected with B16-F1 cells. As in the previous two models, IL-2 and IFNγ production by CD4+ T cells harvested from the ipsilateral DLN was significantly reduced compared to cells harvested from contralateral NDLN or from tumor-free mice. (FIGS. 1E and 1F). Altogether, these results support that melanoma tumors induce hyporesponsiveness in tumor antigen-specific CD4+ T cells, which translates in a reduced capacity to produce effector cytokines upon re-stimulation.

Figures 2A, 2B, 2C, 2D:
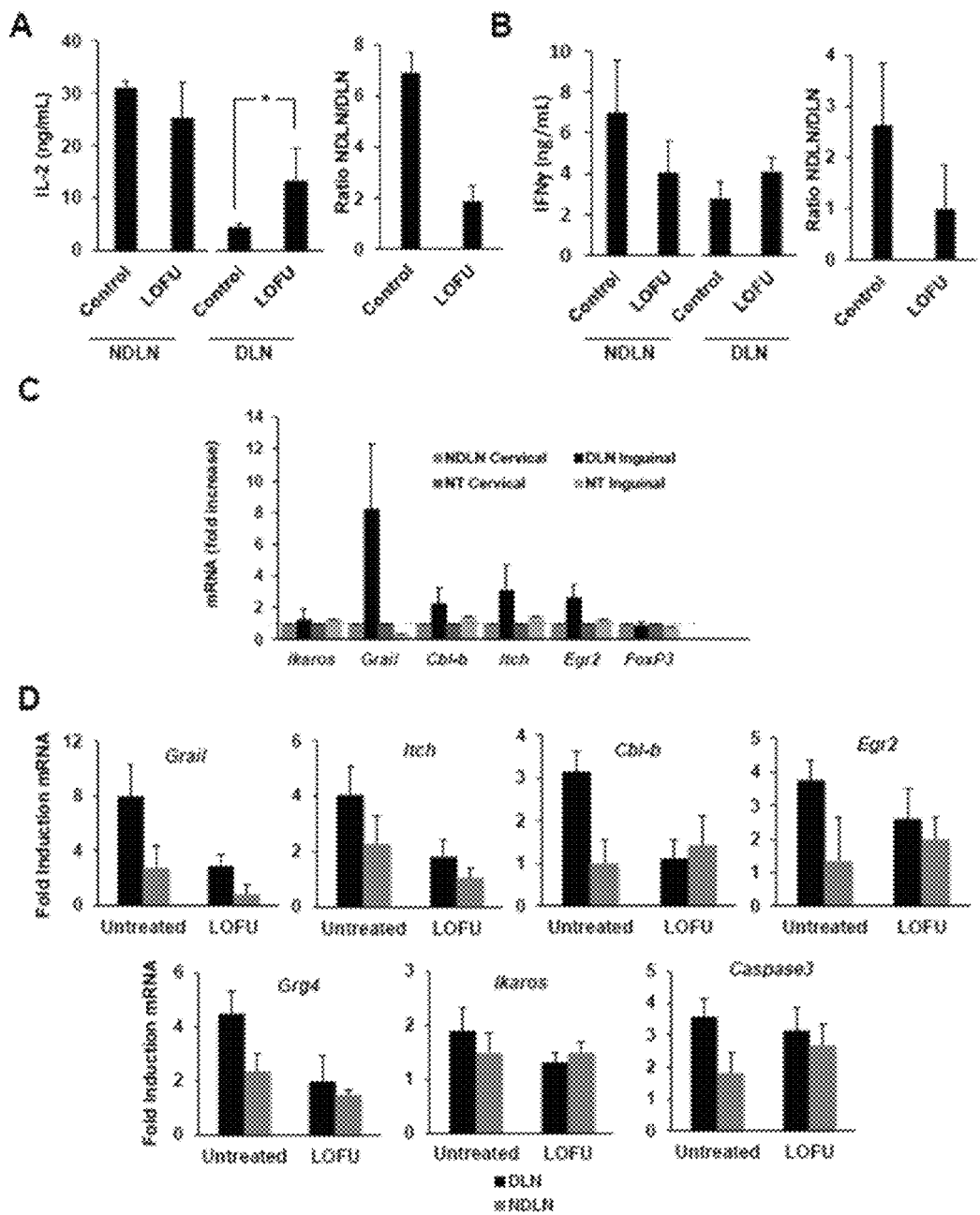
FIG. 2A-2D. Treatment of melanoma tumors with LOFU overcomes tumor induced CD4+ T cell tolerance: 2A-B. Tumors were induced in C57Bl/6 mice by s.c. injection of $3\times10^5$ B16-F1 melanoma cells in the lumbar flank. Tumors were left untreated or treated with LOFU. Thirty-six hours after FUS treatment, CD4+ T cells were isolated from tumor DLN or NDLNs and stimulated with anti-CD3 and anti-CD28 antibodies. IL-2 and IFNγ production was assessed by ELISA. The results (total cytokine production and ratio of the levels of cytokines produced by T cells from NDLN and DLN in each group) are presented as mean+SEM from 3 different mice per condition. Differences between cytokine production of DLN T cells in untreated or treated mice were analyzed using a 2-tailed t test (*$P<0.05$). 2C. Mice were challenged with $3\times10^5$ B16 melanoma cells to induce tumors. Following tumor development total RNA samples were extracted from CD4+ T cells isolated from the DLN and NDLN of tumor-bearing mice, and tumor-free control mice. Expression of anergy-associated genes was measured by quantitative RT-PCR. The results are shown as fold induction of gene expression in the DLN or NDLN resident T cells in tumor bearing mice compared to T cells isolated from tumor-free mice. The data represent mean+SEM from 3 independent experiments. 2D. B16-F1 melanoma tumors were induced in Tyrp1 mice that were then left untreated or treated with LOFU. The expression of different anergy-associated genes was measured by RT-PCR in CD4+ T cells isolated from the DLNs and NDLNs. Expression of the anergy-associated genes is presented as fold induction (mean+SEM from 5 independent experiments) over the values obtained in T cells from Tyrp1 mice bearing no tumor.

Treatment of primary B16 melanoma with LOFU overcomes tumor-induced tolerance in CD4+ T cells: HIFU is currently being used to predominantly cause tumor ablation through the generation of high amounts of heat inside the tumor tissue leading to coagulative necrosis. Although HIFU is a very effective, noninvasive ablative procedure to achieve local tumor control, it destroys the vasculature and tissue infrastructure almost instantaneously, thereby limiting the infiltration of dendritic cells and immune cells for antigen presentation and recognition. It was explored whether administering LOFU would induce a non-lethal thermal/mechanical stress in the tumor tissue that could generate novel tumor antigens and/or induce the expression of stress-induced proteins, which could increase the immunogenicity of the tumor and overcome tumor-induced tolerance of CD4+ T cells. In order to examine this possibility, primary B16-F1 melanoma tumors grown on separate groups of C57Bl/6 J mice were either left untreated or treated with LOFU. Thirty six hours after LOFU treatment, DLN and NDLN resident CD4+ T cells were isolated from both groups of mice, and re-stimulated ex-vivo with antiCD3 and antiCD28 antibodies. CD4+ T cells from the DLN of the LOFU-treated mice produced significantly more IL-2 compared to the cells obtained from the group of mice bearing untreated tumors. In contrast, T cells from the corresponding NDLN produced comparable amounts of IL-2 in treated and untreated mice (FIG. 2A). A similar, but less pronounced effect, was observed on IFNγ production in these same experimental groups of mice (FIG. 2B). Overall, these results indicated that LOFU treatments of B16 melanoma tumors appear to bolster CD4+ T cells to overcome the hyporesponsive state induced by the melanoma tumor microenvironment, suggesting improved activation and reduced tumor-induced T cell tolerance.

It has previously been shown that melanoma tumors can induce an NFAT1-dependent program of gene expression that produces a set of proteins which interfere with TCR signaling and directly inhibit expression of cytokines, resulting in the establishment of functional anergy in CD4+ T cells (21). To determine the possibility that LOFU treatment could inhibit tumor-induced T cell tolerance by preventing anergy induction and be responsible for the increased cytokine expression observed in the DLN resident CD4+ T cells following treatment with LOFU, the expression of those anergy-associated genes in CD4+ T cells isolated from the DLN of mice bearing B16 tumors was first monitored and compared with the expression of those genes in T cells harvested from NDLN of the same mice. T cells from the DLN of tumor-bearing mice expressed higher levels of anergy-associated genes, including the E3 ubiquitin ligases Grail, Cbl-b and Itch and the transcription factor Egr2 (FIG. 2C). However, no difference in the expression of Foxp3 was observed between the DLN and NDLN T cells in tumor bearing mice, suggesting that an increased presence of regulatory T cells was not likely contributing to the decreased CD4+ T cell responses under the conditions used in this study (FIG. 2C).

It was then determined if treatment of B16 melanomas with LOFU would have an effect on the expression of those anergy-associated genes in T cells. To assess responses induced by endogenous tumor antigens, B16 tumors growing on Tyrp1 mice were either left untreated or treated with LOFU. CD4+ T cells were isolated from the DLN and NDLN and the expression of several anergy-associated genes was assessed. T cells derived from the DLN showed varying degrees of upregulation of 6 of the 7 anergy genes analyzed, including Grail, Itch, and Cblb, as well as the transcription factors Egr2 and Grg4, and the protease Caspase3 (FIG. 2D). Another transcription factor, Ikaros, which is also upregulated in several in vitro and in vivo T cell anergy models, was not significantly upregulated in this melanoma model of tumor-induced anergy, and its levels remained largely similar in both the DLN and NDLN derived T cells (FIG. 2D). Interestingly, when the tumors were treated with LOFU, the expression of 5 of those genes, Grail, Itch, Cblb, Egr2 and Grg4 in the T cells isolated from the DLN was not upregulated and showed levels comparable to the expression of these genes in the NDLN (FIG. 2D), supporting that LOFU treatment inhibited the induction of the expression of anergy-inducing genes in tumor antigen-specific CD4+ T cells.

LOFU treated melanoma tumors are able to reactivate anergic tumor antigen-specific T cells: The results supported that tumor-induced T cell tolerance could be overcome following LOFU treatment. This observation was substantiated by the fact that the expression of several anergy-associated genes was decreased in T cells from tumor DLN following LOFU treatment of the tumor site, while activation-induced cytokine expression was restored to levels close to those detected in T cells isolated from distal NDLN or in T cells isolated from control non-tumor bearing mice.

Figure 3A:
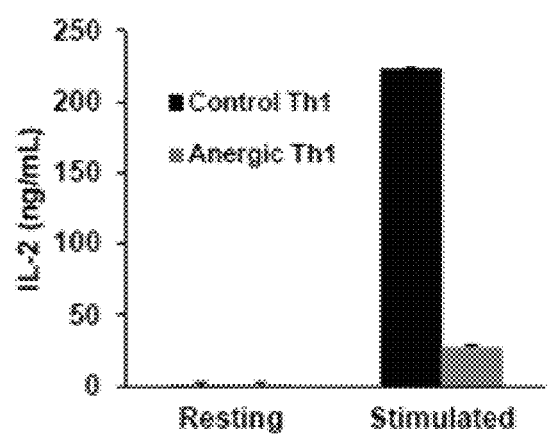
FIG. 3A-3B. Lysates from LOFU-treated B16-F1 melanoma tumors can reverse the hyporesponsive state of anergic T cells 3A. Naïve CD4+ T cells were isolated from spleens and lymph nodes of Tyrp1 mice, and differentiated into TH1 cells. Cells were then either left untreated or treated with anti-CD3 alone for 16 hours to induce anergy. Cells were then rested for 72 hours in strict absence of IL-2 and re-stimulated with anti-CD3 and anti-CD28 antibodies. IL-2 levels were measured by ELISA. The results are shown as mean+SEM from 2 independent experiments. 3B. CD11c+ dendritic cells were isolated from spleens of tumor-free Tyrp1 mice. Anergic TH1 cells generated from Tyrp1 mouse-derived CD4+ T cells as described in (3A) were co-cultured with the dendritic cells and tumor lysates derived from untreated or LOFU-treated B16-F1 melanoma tumors. Supernatants were collected after 24 hours and assayed for IL-2 by ELISA. Results are shown as mean+SEM from 2 independent experiments with 3 independent sets of tumor lysates used in each experiment. Data were analyzed using ANOVA with a Tukey post-test (**$P<0.01$).
Figure 3B:
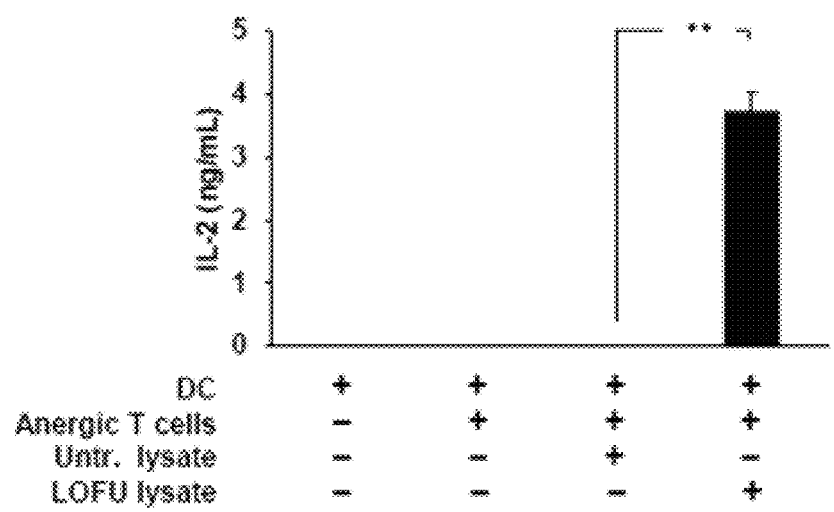

Whether LOFU might not only prevent the induction of tumor-antigen specific T cell anergy but also reverse established anergy and generate a productive effector response in previously tolerized T cells was investigated. Naïve CD4+ T cells were isolated from spleen and lymph nodes of Tyrp1 mice, in vitro differentiated into TH1 cells and anergized by activating them through partial stimulation using with anti-CD3 antibodies in the absence of co-stimulation. As expected, T cells became hyporesponsive and showed a profound decrease in IL-2 production upon re-stimulation with anti-CD3 and anti-CD28 antibodies (FIG. 3A). These anergic cells were then re-activated with CD11c+dendritic cells loaded with lysates derived from either untreated or LOFU treated melanoma tumors. As expected, anergic Tyrp1 T cells stimulated with dendritic cells loaded with tumor lysates from untreated B16-F1 melanoma produced negligible amounts of IL-2. However, when dendritic cells were loaded with tumor lysates prepared from LOFU-treated tumors, previously anergized T cells produced significantly more IL-2 than those activated with untreated lysates (FIG. 3B). These results indicate that LOFU treatment of melanoma tumors might result in the generation of immunogenic molecules that can enable dendritic cells to deliver activating signals that can breach tolerance, enabling otherwise anergic T cells to respond to antigen re-encounter and generate a productive response.

Figures 4A, 4B, 4C, 4D:
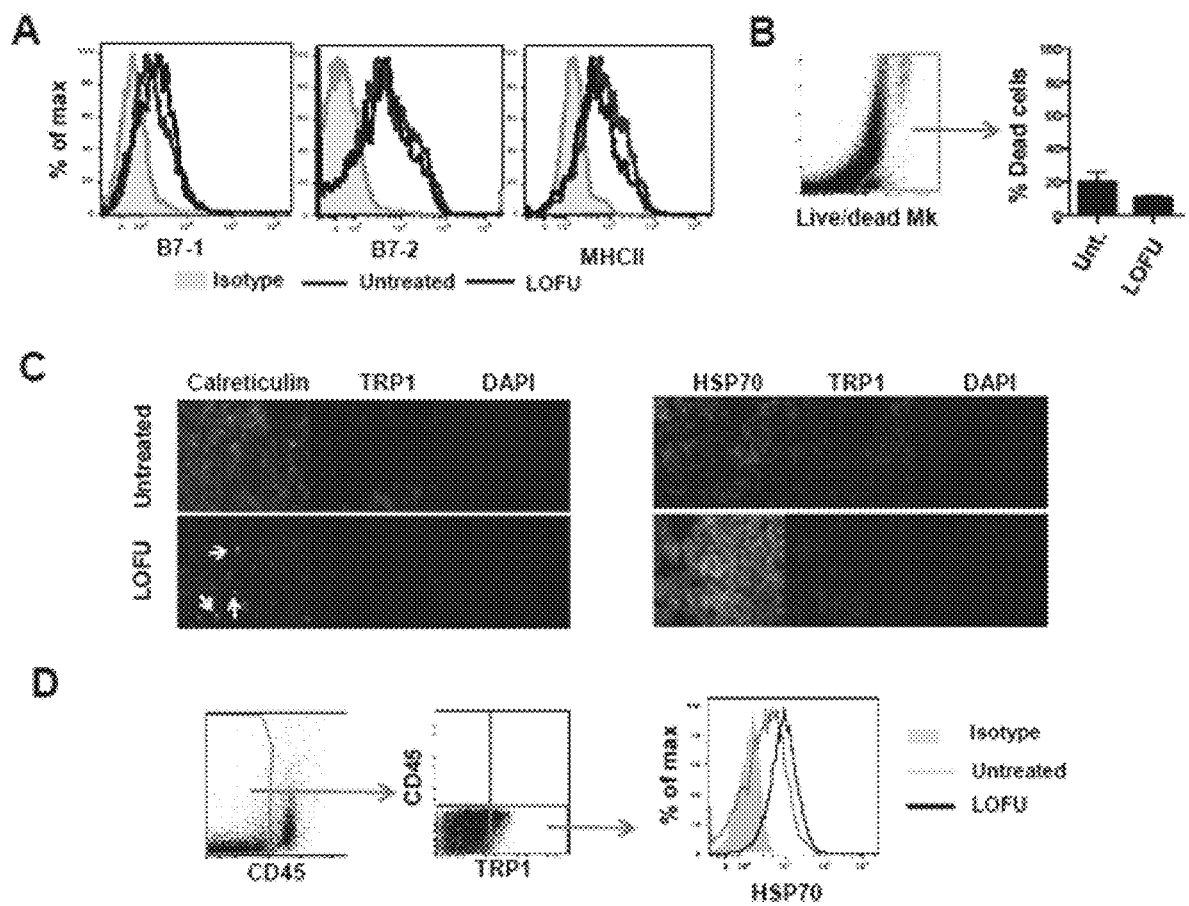
FIG. 4A-4D. FUS treatment causes changes in expression and cellular distribution of Hsp70 and calreticulin in B16-F1 melanoma cells. 4A. Total DLNs resident cells from untreated and LOFU-treated B16-F1 melanoma-bearing mice were isolated and immunostained for CD11c to gate dendritic cells. Surface expression of B7.1, B7.2 and MHCII was then assessed by flow cytometry. Appropriate isotype controls were used for each primary antibody. Representative histograms are shown. 4B. Representative FACS dot plot of B16 tumor cell suspension obtained from untreated or LOFU treated mice were stained with a viability marker (Live/dead Mk). Relative quantification of dead cells is reported. Box and arrow indicate dead cells (Live/dead MK+). 4C. Immunofluorescence staining of B16-F1 tumor tissues isolated from untreated mice or from mice treated with LOFU. Tissue sections were stained with antibodies to detect calreticulin or Hsp70 and TRP1. Nuclei were stained with DAPI. Magnification 60×. 4D. Cells from tumors of LOFU treated mice and untreated mice were stained for CD45 and for the expression of TRP1. CD45-TRP1+B16 cells were then analyzed for the expression of Hsp70. A representative histogram is shown. Gates and arrows indicate the selected population for the analysis.

Treatment of melanoma with LOFU induces changes in the expression and subcellular distribution of the molecular chaperones calreticulin and Hsp70 in melanoma tumor cells: Activation of melanoma-specific T cells by dendritic cells is a crucial event in determining their fate. A successful antigen presentation event that is able to elicit an effector T cell response is critically dependent on the activation state of dendritic cells that would otherwise deliver tolerogenic stimuli. The results indicate that treatment of melanoma tumors with LOFU resulted in increased CD4+ T cell activation as consequence of hindering tumor-induced T cell tolerance. This could potentially result from the generation of more immunogenic dendritic cell populations. To test the effect of LOFU on the ability of dendritic cells of efficiently present antigens to T cells, total cells from the DLNs of tumor-bearing mice were first isolated, untreated or treated with LOFU, and immunostained to measure the expressions of B7.1, B7.2, and MHCII on CD11c+ dendritic cell populations by flow cytometry. No significant enhancement of the expression of these proteins in the LOFU-treated mice was detected (FIG. 4A).

Trafficking of tumor antigens by molecular chaperones, including calreticulin and Hsp70, is also crucial for the subsequent productive presentation of antigens to T cells (32-35). Both in vivo and in vitro approaches were employed to detect membrane calreticulin and Hsp70 in untreated and LOFU treated B16 melanoma tumors. Tumors, either left untreated or treated with LOFU, were harvested from tumor bearing mice, made into single cell suspensions and stained with a live/dead marker to assess cell viability. No differences in cell viability were observed in response to LOFU treatment, supporting the notion that the low energy form of FUS was not directly inducing tumor cell death (FIG. 4B). B16 melanoma tumors were left untreated or exposed to LOFU treatment and tumor tissue sections were put on slides. Slides were subjected to staining with anti-Hsp70 or anti-calreticulin antibodies for a subsequent detection by immunofluorescence. Immunofluorescence analyses of LOFU treated melanomas confirmed that LOFU induced increased expression of Hsp70 (FIG. 4C). Interestingly, compared to untreated cells, LOFU treated cells also showed a change in the distribution of calreticulin, which appeared to accumulate in discrete regions of the plasma membrane on B16 cells (FIG. 4C). To determine if the increased Hsp70 expression also correlated with increased presence in the membrane of this protein, non-permeabilized CD45-TRP-1+B16 melanoma cells were stained for Hsp70 and cell surface expression following LOFU treatment assessed by FACS. This analysis confirmed that LOFU treatment of B16 melanomas caused increased membrane presence of Hsp-70 in tumor cells (FIG. 4D).

LOFU treatment of melanoma tumors potentiates dendritic cell-mediated tumor antigen presentation to elicit a stronger CD4+ T cell response: To determine the possibility that LOFU treatment of tumors could result in enhanced stimulatory capacity of resident dendritic cells, it was directly tested if lysates prepared from LOFU treated tumors could elicit enhanced priming of antigen specific T cells leading to a more robust effector response. For this experiment, B16-F1-OVA melanoma cells were used to induce tumors in C57BL/6 mice. Lysates were prepared from untreated and LOFU treated tumors. Splenic dendritic cells and responder naïve CD4+ T cells were isolated from C57BL/6 and OT-II tumor-free mice, respectively, and were co-cultured in the presence or absence of the different tumor lysates described above. Though the OVA containing tumor lysates could act as a source of tumor antigen to prime responder T cells, exogenous OVA323-339 peptide was also added to ensure uniform loading of dendritic cells with this peptide in all conditions and more accurately determine the tolerogenic or activating nature of the different tumor lysates.

Figure 5A:
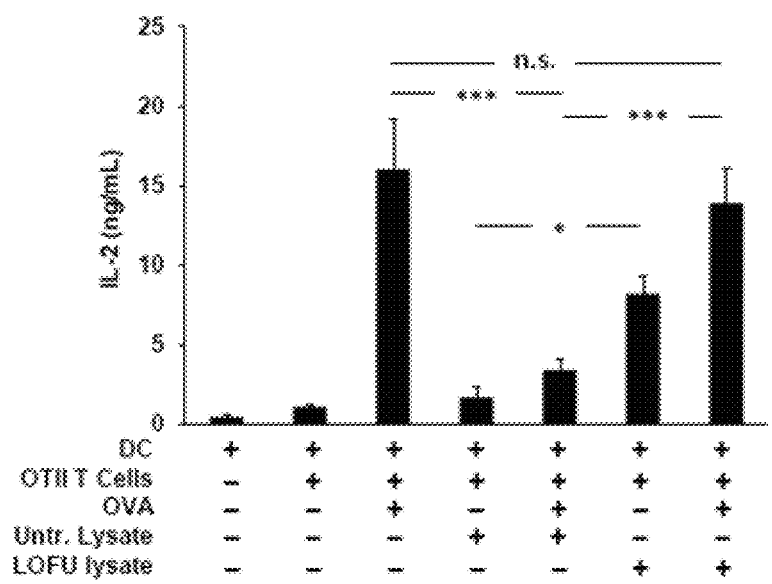
FIG. 5A-5B. FUS treatment of melanoma tumors potentiate dendritic cell-mediated priming of CD4+ T cells: 5A. CD11c+ splenic dendritic cells were purified from C57Bl/6 mice and co-cultured with responder naïve CD4+ T cells isolated from OT-II mice. B16-F1-OVA melanoma tumor lysates were prepared from untreated or LOFU treated tumor-bearing mice and added to the respective cultures to drive dendritic cell mediated T cell stimulation. In separate samples exogenous OVA323-339 peptide was also added along with tumor lysates. Supernatants were collected after 24 hours, and IL-2 production was assessed by ELISA. The results are shown as mean+SEM from 4 independent experiments and analyzed with one-way ANOVA followed by a Tukey posttest (*$P<0.05$; *$P<0.001$; n.s., not significant). 5B**. B16-F1 melanoma tumors were left untreated or treated with LOFU. Tumor DLN were isolated and depleted of T cells. DLN cells were then co-cultured with naïve Tyrp1 CD4+ T cells and stimulated with B16 melanoma tumor lysates obtained from in vitro cultures. Supernatants were collected 24 hours later and analyzed for IL-2 levels by ELISA. The data is shown as mean+SEM from 3 independent experiments. Differences between cytokine production in cultures using DLN cells from untreated or LOFU-treated mice were analyzed using a 2-tailed t test (*$P<0.05$).

As expected, control responder OT-II T cells, upon activation with dendritic cells loaded with OVA323-339 peptide, showed a strong response with elevated levels of IL-2 production. However, lysates obtained from untreated tumors markedly inhibited OT-II responses and resulted in a profound decrease in IL-2 production, even though exogenous OVA323-339 peptide was added to the culture (FIG. 5A). Interestingly, as opposed to untreated lysates, lysates derived from LOFU treated tumors did not only have no negative effect on the responses of OT-II cells to OVA323-339 but were also able to elicit a strong activation of OT-II responder T cells even in the absence of exogenous peptide (FIG. 5A). These results extended further support the observation that LOFU treatment of B16 melanoma tumors prevents the negative effect on the T cell priming capacity of dendritic cells that normally occurs in the tumor microenvironment.

Figure 5B:
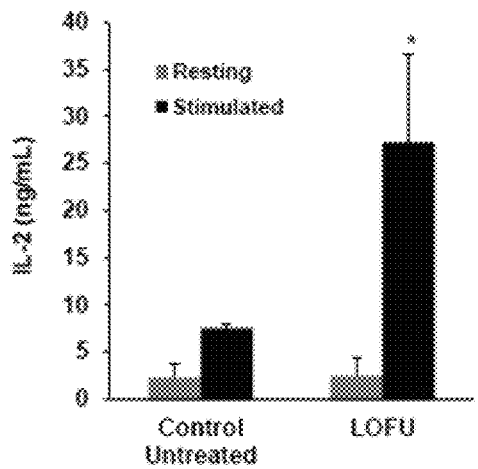

Next it was determined whether tumor DLN resident antigen presenting cells would be functionally more efficient at activating target T cells following LOFU treatment of melanoma tumors. To that effect, B16-F1 melanomas were induced on C57BL/6 mice and were either left untreated or treated with LOFU. DLN cell suspensions were depleted of T cells and used to test the capacity and DLN antigen presenting cells to activate tumor antigen specific T cells. T-cell depleted DLN cells were thus co-cultured for 24 hours with naïve Tyrp1 CD4+ T cells and lysates prepared from B16 in vitro cultures. IL-2 production was measured by ELISA to monitor responder T cell priming. Cells isolated from the DLN of LOFU treated tumor-bearing mice showed a significantly increased ability to activate Tyrp1 CD4+ T cells compared with cells isolated from untreated mice. (FIG. 5B). These data support that LOFU treatment of B16 melanoma results in the generation of antigen presenting cells that are functionally more efficient at activating tumor-antigen responder T cells.

Figures 6A, 6B, 6C, 6D:
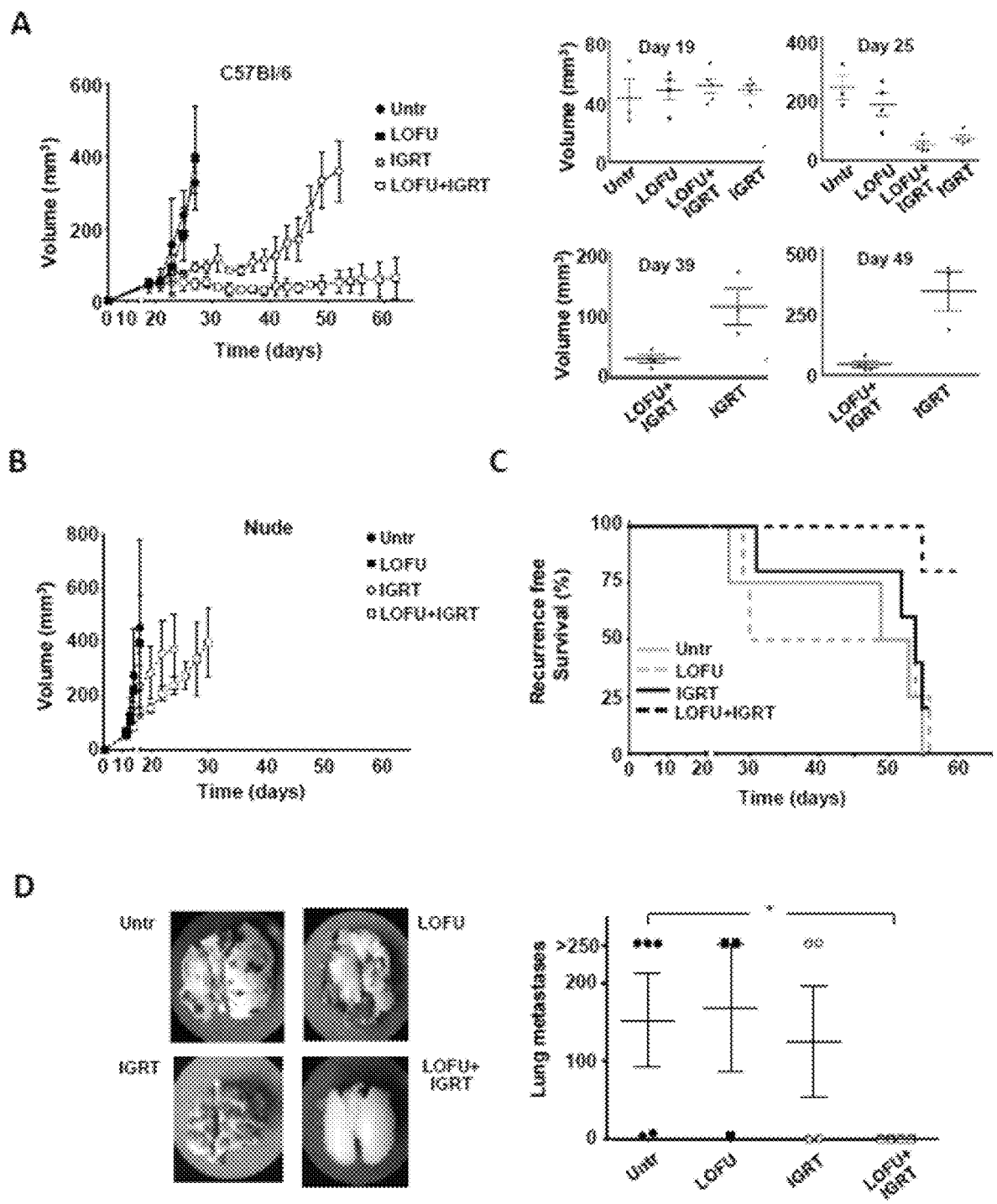
FIG. 6A-6D. FUS followed by hypofractionated IGRT results in T-cell mediated long term primary tumor control and reduced distal metastases: 6A C57Bl/6 mice with 50 mm$^3$ subcutaneous dorsal right hind limb tumors were separated into one of four treatment groups: untreated, LOFU, hypofractionated IGRT, or LOGU+IGRT and tumor growth monitored for 62 days or until primary tumor grew beyond 300 mm$^3$. Graph shows mean±SEM of tumor volume from one of two representative experiments (3-5 mice per group). Data were analyzed with either one-way ANOVA followed by a Bonferroni correction post test (before day 29) or by 2-tailed student t test (after day 29). Significant differences (defined as $P<0.05$) between untreated or LOFU-treated mice and IGRT or LOFU+IGRT treated mice occurred after day 25, and between IGRT treated and LOFU+IGRT treated mice after day 35. Individual graphs showing the distribution of tumor size at specific days are also shown. 6B. Similar experiments as the ones described in 6A were performed in BALB/c nude mice. No significant differences were observed among the different groups at any time point. 6C. C57Bl/6 mice were monitored for primary tumor progression/recurrence, defined as either recurrence reaching a volume of 150 mm$^3$ or the development of local metastasis to the popliteal or inguinal lymph nodes. In addition, animals that died spontaneously were scored as having recurrence or progression of disease. Recurrence free survival data was analyzed using the Mantel-Cox test. 6D. Lungs were harvested from animals that either died spontaneously, required euthanasia due to overwhelming tumor burden, or were sacrificed at the end of a two month long experiment. Lung metastasis were then measured. Lungs with nodules that fuse into plaques, or exceed 250 were deemed too numerous to count and assigned a maximal value of 250. A representative specimen is shown for each treatment group. The results are shown as mean±SEM, with n=3-5 mice per group, analyzed with a Kruskal-Wallis test, followed by Dunn's posttest. *$P<0.05$.

LOFU followed by ablation of tumor by hypofractionated IGRT results in enhanced T-cell mediated control of primary melanoma lesions: In order to further determine the consequences of our observation that LOFU therapy can modulate tumor immunogenicity and enhance anti-tumor immune responses, a series of in vivo treatment strategies evaluating primary tumor control were performed using a combination of LOFU with or without tumor ablation using daily 10 Gy hypofractionated IGRT to a total dose of 30 Gy per mouse with established B16-M1 tumors located subcutaneously in the right dorsal hindlimb. Treatment was initiated for all mice when tumor volume reached ~50 mm$^3$. Tumor volumes in each group were then measured three times a week for up to 62 days (FIG. 6A). Untreated C57BL/6 or mice treated with LOFU alone continued to experience rapid primary tumor growth, reaching a volume of ≥300 mm$^3$ within 10 days of treatment, at which point a below-the-knee amputation (BKA) was performed (FIG. 6A). In contrast, mice within the hypofractionated IGRT or LOFU+IGRT groups experienced significant growth delay for up to 3-weeks following treatment after which mice treated with IGRT alone began to exhibit primary tumor regrowth, reaching a volume ≥300 mm$^3$ at approximately 5-weeks. Remarkably, the mice in the LOFU+IGRT group had a sustained response, with limited tumor growth for more than 6-weeks following treatment. The reduction in tumor volume in the group receiving LOFU+IGRT or IGRT when compared with the untreated or LOFU alone groups was statistically significant by day 25 (P<0.05). Moreover, the reduction in tumor volume in the LOFU+IGRT group compared with IGRT alone was statistically significant by day 35 and remained statistically significant (P<0.05) for the duration of the experiment. (FIG. 6A). In addition, mice in the LOFU+IGRT group demonstrated regression of tumors from their baseline measurements and a complete tumor-free response was seen in 4 out of 5 mice.

To corroborate the immunomodulatory effect of LOFU, similar experiments were performed using the immunocompromised BALB/c nude model. In these mice B16-M1 tumors grew much more rapidly, reaching ≥300 mm$^3$ approximately 1-week earlier than C57BL/6 mice. The overall treatment response was similar, with untreated and LOFU alone resulting in no significant primary tumor control, while IGRT and LOFU+IGRT delayed primary tumor growth (FIG. 6B). However, in both the IGRT and LOFU+IGRT treatments, primary control was short lived. In fact, BKA was required in the IGRT group less than 2-weeks after starting treatment and in less than 3-weeks in the LOFU+IGRT group. Additionally, LOFU+IGRT in immunocompromised mice failed to result in statistically significant primary tumor control when compared to IGRT alone (FIG. 6B).

LOFU followed by hypofractionated IGRT results in prolonged recurrence free survival and reduced pulmonary metastasis: Based on the data, it was hypothesized that LOFU-induced enhanced anti-tumor T cell responses might augment therapeutic IGRT not only achieving better control of local disease, but also of microscopic disease and distant metastases. As B16-F10 is an aggressive cell line that rapidly grows to an unacceptable size if not treated, mice with primary tumors >300 mm$^3$ required BKA. Of note, by the time a BKA was performed, cells from the primary tumor had already spread to the draining popliteal LN (data not shown). Within the subsequent weeks, the draining popliteal LN grew rapidly and became visibly enlarged, while the more distal inguinal LN became clearly palpable. When the tumors reached this point, there are no procedures that can be performed to alleviate discomfort and these mice were euthanized. Consequently, overall survival cannot be adequately assessed in mice with massive tumor burden. Therefore, it was decided to assess two other parameters: recurrence free survival, where spontaneous death or euthanized animals with excessive local recurrence tumor burden were scored as positive events; and the development of lung metastases.

The combination of LOFU+IGRT provided a statistically significant (P=0.04) recurrence free survival advantage over either treatment alone in C57BL/6 mice (FIG. 6C). Notably, in all groups except C57BL/6 LOFU+IGRT, local metastasis to the draining popliteal or inguinal LN frequently necessitated the use of euthanasia. Furthermore, while mice that were treated with LOFU+IGRT showed a strict control of lung metastases, in the other three groups, even animals with relatively little local recurrence ultimately died due to overwhelming lung metastasis (FIG. 6D).

Discussion

The adaptive immune system constantly surveys for malignantly transformed cells. This is largely achieved by recognition of tumor-associated antigens that prime the appropriate T cell repertoire to mount antitumor immune responses. However, tumors also employ diverse mechanisms to evade the adaptive immune system and thwart antitumor T cell responses (1). As a result, successful therapy against cancer has to overcome the major obstacle of tumor-induced tolerance (36). Several mechanisms have been described to explain how tumors induce tolerance in different T cell subtypes, including defective presentation of tumor antigens and inadequate activation of antigen presenting cells, signaling through co-inhibitory receptors, immunosuppression by factors released within the tumor microenvironment and local recruitment of suppressor cells (9, 15-17, 20, 37-39). Treatments that promote immunogenic cell death (ICD) of cancer cells can mitigate and drive reversal of tolerance. The hallmarks of ICD include the release of damage-associated molecular patterns (DAMPs), translocation of certain chaperone complexes to the cell surface, and increased dendritic cell-mediated cross-presentation of tumor-associated antigens (40). In this study it was sought to investigate if novel treatment for melanoma using non-ablative LOFU would result in prevention, reversal or mitigation of tumor-induced tolerance and therefore in enhanced anti-tumor immune responses.

Thermally ablative HIFU, while able to control primary tumors, is typically not effective at preventing micro-metastatic invasions in surrounding or distant tissues, suggesting that cell death caused by this FUS modality fails to adequately prime an adaptive anti-tumor immune response. Indeed, local or distal micro-metastatic invasions may be prevented or ameliorated by an adequately primed immune system that could eliminate the relatively small tumor load of cells that escape initial ablative treatment. In this study, using a B16 murine melanoma model, we show that the use of non-ablative LOFU treatment enhances T cell effector responses by overcoming the tolerizing effects of the tumor microenvironment and prevents local recurrence and distal metastases when administered prior to an ablative treatment.

Development of T cell hyporesponsiveness to tumor antigens has been described in T cells in several mouse tumor models and in human cancers (15, 18, 41). This laboratory has previously reported that tumor-antigen specific CD4+ T cells become anergic in tumor bearing mice and express a series of anergy-associated genes that have been shown to hinder their ability to proliferate and produce effector cytokines (21, 42). Furthermore, prevention of the expression of those genes in mice that lack NFAT1 or Egr2, two transcription factors responsible for the expression of anergy-inducing genes (43-45), leads to inhibition of tumor-antigen specific T cell hyporesponsiveness and improved control of local tumor growth (19, 21). Using two different B16 mouse melanoma models, the data confirm that resident tumor antigen specific CD4+ T cells in the tumor DLN upregulate the expression of anergy associated genes, including Grail, Itch, Cblb, Grg4, and Egr2. The activation of this program of gene expression was well correlated with a reduced ability to produce cytokines following ex-vivo restimulation, supporting that B16 melanoma induces an intrinsic state of hyporesponsiveness in tumor antigen specific CD4+ T cells. Importantly, treatment of the primary tumor with LOFU resulted in an increased ability of those tumor-antigen specific CD4+ T cells to produce cytokine upon re-stimulation. US-induced restoration of the responsiveness to TCR engagement, in otherwise anergic cells, was accompanied by a reduction, to varying extents, of the expression of most anergy-inducing genes. The absence of FUS-induced changes in Foxp3 transcripts in DLN resident CD4+ T cells in tumor bearing mice suggests, however, that FUS did not affect Foxp3+ Treg migration or differentiation and supports that LOFU prevented tumor-induced-tolerance by inhibiting T cell anergy.

Initial studies on tumor induced T cell anergy identified the key role that antigen presenting cells played in this process and defective dendritic cell maturation has been defined as a major determinant of inefficient priming of tumor-antigen specific T cells (20, 46). Recently, it has been shown that unstable immunological synapses formed between T cells and dendritic cells presenting tumor antigens result in delayed nuclear export of NFAT and the likely activation of a tolerogenic NFAT-dependent program of gene expression that includes Egr2 (47). Increased T cell activation that follows LOFU treatment of B16 melanomas could potentially result from several different phenomena. First, treatment of the tumors with LOFU delivers both thermal and mechanical stress to the tumor cells. This stress could help generate novel unique "non-self" tumor antigens that, in turn, could make the tumor more immunogenic and less able to induce tolerance. Alternatively or additionally, the release of stress-induced danger signals by tumor cells could generate a tumor microenvironment that targeting dendritic cells would find less conducive to induction of tolerance in T cells. Stress associated molecular chaperones, including heat shock proteins and calreticulin, have been implicated in dendritic cell maturation and enhanced anti-tumor immunity (32, 48-51). There is evidence that primary tumor lysates are rich in heat shock proteins that can trigger maturation signals in dendritic cells (52). Importantly, heat shock proteins are also capable of associating with and delivering antigenic peptides from tumor cells to dendritic cells, furthermore their presence in the tumor cell plasma membrane has been associated with increased immune responses (53-55). Calreticulin has also been described to play an important role in antitumor response and its translocation to the surface of tumor cells has been associated with increased phagocytosis of the cell by dendritic cells and immune activation (56, 57). Previous studies using HIFU in murine adenocarcinoma models showed that this treatment significantly increased expression of co-stimulatory molecules on dendritic cells, which also produced higher levels of IL-12 and resulted in increased CTL activity (58, 59). The data show that LOFU induces a redistribution of calreticulin in B16 cells and an increase in the expression of the inducible heat shock protein Hsp70, suggesting that cellular stress mediated by LOFU is capable of inducing changes in the expression of those stress-induced proteins. Although no significant differences in the expression of MHC-II or B7 proteins were detected, it cannot be ruled out that LOFU may also induce other changes in dendritic cell function that can contribute to the potentiation of the efficient presentation of tumor antigens. In any case, the data support that the thermal/mechanical stress inflicted by LOFU is likely responsible for the enhanced tumor immunogenicity and for promoting T cell activation over anergy.

T cell tolerance induced by tumor antigens remains a major obstacle in treating cancer. Effective reversal of tolerance in tumor-specific T cells is a key goal in clinical antitumor strategies. Our data find that pre-established anergy in T cells can be reversed by lysates prepared from LOFU treated melanoma tumors. This observation opens up the possibility that LOFU treatment of tumors could release novel immunogenic molecules from tumor cells that would not only prevent but also reverse pre-established tumor tolerance in T cells. Signaling through the IL-2 receptor has long been known to prevent and reverse clonal anergy in T cells (60-62). However, elevated amounts of IL-2 in could not be detected in any of lysates, untreated or treated with LOFU (data not shown), making presence of IL-2 an unlikely candidate to have caused the reversal of anergy in the experiments. However, it is possible that other factors could contribute to this phenotype. In fact, T cell co-stimulation through the TNFR family member OX-40 ligand has also been shown to prevent and overcome T cell anergy in addition to increased effector response in both CD4+ and CD8+ T cells (63-65). Engagement of CD137, CD40 and blockade of PD1 have also been reported to prevent and reverse pre-established CD8+ T cell tolerance in vivo (66-68).

Pretreatment of melanoma tumors with LOFU before performing ablative therapy using hypofractionated IGRT resulted in a significant delay in tumor growth, and in several cases, complete regression of tumors was observed only in immunocompetent mice. Recurrence free survival in these mice were also markedly improved following that protocol. In addition, incidences of lung metastases were minimal in mice that received LOFU prior to tumor ablation compared to mice that received only ablative IGRT. Strikingly, the LOFU failed to confer similar protection when similar experiments were performed on T cell-deficient nude mice. This observation indicates that the protective effect of LOFU is not restricted only to control primary tumor, but can prevent the establishment of metastatic foci either locally or distally. This protection from metastasis could possibly result from the prevention/reversal or both of T cell tolerance to tumor antigens. LOFU pretreatment not only controlled tumor growth more effectively, but, as indicated before, likely resulted in the generation of strongly immunogenic IGRT-induced tumor death that provided protection from metastasis and ensured longer recurrence free survival.

Prevention of T cell tolerance to endogenous tumor antigens is of paramount importance in treating cancer. The work herein shows that treatment of primary tumors with LOFU can accomplish that, making it a candidate therapy for the development of an in situ autologous tumor vaccine. FUS treatment of solid tumors, in combination with an ablative approach could prove to potentiate efficacy of primary tumor eradication, as well as prevention of metastases.

Methods and Materials

Mice: 6-8 week old C57BL/6, B6.Cg-Rag1tm1MomTyrp1B-wTg(TcraTcrb)9Rest/J (Tyrp1) and B6.Cg-Tg(TcraTcrb)425Cbn/J (OT-II) mouse strains were purchased from The Jackson Laboratory. BALBc/Nude mice were obtained from National Cancer Institute, distributed through Charles River. All mice were housed and maintained in pathogen-free facilities.

Culture of B16 cell lines and primary CD4+ T cells: B16-F1 and B16-F10 melanoma cell lines were purchased from the American Type Culture Collection (ATCC). A highly aggressive subclone of B16-F10 (B16-M1) was generated by isolating and expanding a metastatic clone that arose in a C57BL/6 mouse 6 weeks after surgical removal of an established primary tumor. The B16-OVA melanoma cell line was kindly provided by E. M. Lord (University of Rochester Medical Center, Rochester, NY). The expression of OVA by B16-OVA cells was confirmed by real time PCR. All melanoma cells were cultured in DMEM (Thermo Scientific) supplemented with 10% heat inactivated FBS, 2 mM L-Glutamine and 250 IU of penicillin/streptomycin.

CD4+ T cells were isolated using anti-CD4 conjugated magnetic Dynabeads (Life Technologies) according to the manufacturer's protocol. Where indicated, CD4+ T cells were differentiated into TH1 helper cells by activation with plate-bound anti-CD3$\Sigma$ (clone 2C11; 0.25 lg/mL) and anti-CD28 (clone 37.51; 0.25 lg/mL) antibodies (BD Biosciences) and cultured for six days in DMEM supplemented with 10% heat inactivated FBS, 2 mM L-glutamine, 50 lM 2-mercaptoethanol, nonessential amino acids and essential vitamins (Cambrex), in the presence of murine IL-12 (10 ng/mL) (eBioscience), anti-mouse IL-4 antibody (clone 11C.11; 10 µg/ml) and 10 U/mL recombinant human IL-2 (Biological Resources Branch of the National Cancer Institute).

Tumor models: $3\times10^5$ B16-F1 melanoma cells suspended in Hanks' Balanced Salt Solution (Invitrogen) were injected s.c. in the lumbar flanks of mice. Melanoma tumors were induced in the footpads by injecting $2\times10^5$ B16-M1 cells in the dorsum of the right hind limb.

Tumor growth monitoring: Primary B16-M1 melanoma dorsal hind limb tumors were measured three times per week with vernier calipers. Tumor volume was calculated using an ellipsoid formula: $V=(\pi/6\times length\times width\times height)$. Primary dorsal hind limb tumors exhibit Gompertzian growth, with a phase I volume of 30-50 mm$^3$, phase II volume of 90-150 mm$^3$, and phase III volume of 300-500 mm$^3$. Therefore, treatment efficacy was determined by determining the tumor growth delay (TGD) to 90-150 mm$^3$, in which the tumor is in the exponential phase II. Tumors that reach 300-500 mm$^3$ begin to enter phase III due to anatomical and vascular limitations. Consequently, below-the-knee amputations were performed on mice with tumors ≥300-500 mm$^3$, in accordance with IACUC approved protocol.

ELISA: 1.5 to $2.5\times10^4$ T cells were left rested or stimulated with either anti-CD3$\Sigma$+anti-CD28 antibodies, T cell depleted OVA peptide 323-339 (OVA323-339)-loaded splenocytes at a 1:5 T cell:splenocyte ratio, or CD11c+ purified dendritic cells (using CD11c-beads; Miltenyi Biotech) loaded with OVA323-339 or melanoma tumor lysates at a 1:3 dendritic cell:T cell ratio. Culture supernatants were typically harvested 24 hours after stimulation, and IL-2 or IFNlevels were measured by a sandwich ELISA (BD Biosciences).

Tumor lysates: Tumors were resected from tumor bearing mice, cut into 1-2 mm pieces and passed through 40 lm nylon meshes. Cells were washed in PBS and resuspended in serum-free DMEM. Cell suspensions were then snap frozen in liquid nitrogen, and thawed at 37° C. for five cycles with visual confirmation of complete lysis by light microscopy. The lysates were spun at 10,000 g for 15 minutes at 4° C., and the pellets with cellular debris were discarded. The supernatant was used along with purified dendritic cells to stimulate T cells.

Immunofluorescence staining tumor tissue was isolated, washed in PBS and embedded in OCT compound (Electron Microscopy Sciences). Tissue sections (Sum) were prepared and permeabilized with acetone for 5 min and incubated with goat serum for 30 min to block non-specific protein-protein interactions. Tissue sections were incubated overnight with the following antibodies: anti-Calreticulin (Pierce, PAS-25922), anti-Trp1 (Abcam, ab3312; clone TA99) and anti-Hsp70 (Novus Biologicals, NBP1-77455). Appropriate secondary antibodies were used for 30 min at room temperature. DAPI (Invitrogen) was used to detect nuclei. At least 10 fields/sample were blindly analyzed with an Inverted Olympus IX81 fluorescence microscope.

Focused ultrasound therapy system. A therapy and imaging probe system (TIPS, Philips Research North America, Briarcliff Manor, NY, USA) was utilized for all ultrasound exposures. The system is capable of delivering focused and spatiotemporally controlled ultrasound energy and consists of a therapy control workstation, RF generators and control electronics, an 8-element spherical shell annular array ultrasound transducer (80 mm radius of curvature, 80 mm aperture), as well as a motion stage to allow for in-plane transducer movement and accurate positioning perpendicular to ultrasound beam axis. The focused ultrasound beam can also be steered approximately ±15 mm out-of-plane using electronic deflection of the focal point. The ultrasound beam propagates vertically into the target through a thin (25 µm) circular plastic membrane, with acoustic coupling provided by degassed water. During therapy, the system allows adjustments of acoustic output power, ultrasound exposure duration, duty cycle, and ultrasound frequency.

In vivo focused ultrasound (FUS) therapy. Mice were anesthetized with a continuous flow 1.5 liters/minute of 1.5% isoflurane in pure oxygen. To ensure proper acoustic coupling, the tumor-bearing leg or lumbar flank were carefully shaved. Once the animal was positioned for therapy, the tumor was acoustically coupled to the TIPS system using degassed water and ultrasound gel. The center of the tumor was then placed at the focal length of 80 mm from the transducer. Ultrasound exposures were delivered to the tumor using a 1 mm grid pattern extending over the entire tumor volume. Two layers of grid points (spaced 5 mm apart) were performed in each tumor, resulting in approximately 160 discrete foci and 5 min exposure duration per tumor. The ultrasound transducer was operated at 1.0 MHz, resulting in an ellipsoid focal spot approximately 1.5 mm in diameter and 12 mm in length (−6 dB of pressure), as measured along the ellipsoid axes. Ultrasound exposures were delivered to the tumor using a 1 mm grid pattern extending over the entire tumor volume. Prior to therapy, the tumor volume was measured to calculate the grid size for the particular treatment. The duration of ultrasound exposure at each grid point was 1.5 s, after which the transducer was automatically positioned over the next grid point and the procedure repeated until the entire tumor volume was covered. Two layers of grid points were performed in each tumor. The therapeutic ultrasound device was operated in continuous wave mode at a specific acoustic power/pressure regimen: acoustic power 3W, peak negative pressure=2.93 MPa (80 mm focal length)/3.81 MPa (85 mm focal length); to provide non-ablative low-energy FUS (LOFU). The resulting in situ intensity (Ispta) at the focus was estimated to be 550 W/cm$^2$ at a depth of 4 mm in tissue. Total energy deposition to a tumor was approximately 900 J.

In vivo hypofractionated cone beam CT image-guided Radiation Therapy (IGRT): All radiation was delivered using Xstrahl Limited's Small Animal Radiation Research Platform (SARRP) to deliver a 10 Gy dose to a target tumor in 341 seconds. Anesthetized animals were placed on stage attached to a motorized platform and the tumor-bearing right hind limb was extended, elevated, and secured to a 1.5 cm adhesive platform to minimize extraneous tissue exposure. Once secure, a cone beam CT (CBCT) was performed and the data opened in 3D Slicer for tissue segmentation and treatment planning. 10 Gy each was delivered for three successive days for a total hypofractionated dose of 30 Gy. In the combination therapy groups, LOFU was performed 2-4 hours prior to CBCT.

Pulmonary Metastasis Evaluation: Lungs were isolated from animals that died spontaneously, were euthanized or were sacrificed at the end of the 8-week experiment. 1 mL of Fekete's solution (Ethanol, Glacial acetic acid and formaldehyde based bleaching fixative) was injected to insufflate the lungs. The trachea was then clamped, and the entire lungs and heart removed en bloc and washed with PBS. The lungs were then placed in Fekete's solution and allowed to bleach for 48 hours prior to analysis. The left lung and the 4 lobes of the right lung were isolated and nodules counted with the aid of a dissecting microscope. Indistinct or fused nodules cannot be reliably enumerated; therefore, the lung was labeled as too numerous to account and assigned an arbitrary metastasis count of 250. Statistical analysis was performed using the non-parametric Kruskal-Wallis test, followed by the Dunn's posttest for multiple comparisons.

Recurrence Free Survival: The following events were scored as positive events in our recurrence free survival analysis: spontaneous death with necropsy validation of tumor involvement, euthanasia due to extensive local metastasis to the draining popliteal or inguinal lymph nodes, or euthanasia due to moribund appearance indicating extensive systemic tumor burden. The following non-tumor-dependent deaths were processed as censored data: death within 24-48 hours of amputation or sacrifice of any animals at the end of the 8-week experiment. In order to prevent selective sacrifice of control or treated animals, cages were labeled using an alphanumeric code such that animal institute veterinarians were blinded from treatment and control groups. Recurrence free survival was analyzed using a Mantel-Cox test, with statistical significance defined as $P<0.05$.

Real time PCR: Total RNA was extracted from cells using RNeasy Micro kit (Qiagen), and cDNA was synthesized using qScript cDNA supermix (Quanta Biosciences). The cDNA samples were subjected to real time PCR using PowerSYBR (Applied Biosystems) as the reporter dye on a StepOnePlus real time PCR system (Applied Biosystems). Expression of the transcripts studied was normalized to beta actin. The primer sets used are the following:

```
actinb:
                                         (SEQ ID NO: 1)
F-GTGACGTTGACATCCGTAAAGA, (SEQ ID NO: 2)
R-GCCGGACTCATCGTACTCC;

Cblb:
                                         (SEQ ID NO: 3)
F-GCAGCATCATTGACCCTTTCA, (SEQ ID NO: 4)
R-ATGTGACTGGTGAGTTCTGCC;

Grail:
                                         (SEQ ID NO: 5)
F-ATGCAAGAGCTCAAAGCAGGAAGC, (SEQ ID NO: 6)
R-GTGCGCAGCTGAAGCTTTCCAATA;

Ikaros:
                                         (SEQ ID NO: 7)
F-GCTGGCTCTCGGAGGAG, (SEQ ID NO: 8)
R-CGCACTTGTACACCTTCAGC;

Caspase 3:
                                         (SEQ ID NO: 9)
F-ACGCGCACAAGCTAGAATTT, (SEQ ID NO: 10)
R-CTTTGCGTGGAAAGTGGAGT;

Egr2:
                                         (SEQ ID NO: 11)
F-TCAGTGGTTTTATGCACCAGC, (SEQ ID NO: 12)
R-GAAGCTACTCGGATACGGGAG;

Grg4:
                                         (SEQ ID NO: 13)
F-TCACTCAAGTTTGCCCACTG, (SEQ ID NO: 14)
R-CACAGCTAAGCACCGATGAG;

Itch:
                                         (SEQ ID NO: 15)
F-GTGTGGAGTCACCAGACCCT, (SEQ ID NO: 16)
R-GCTTCTACTTGCAGCCCATC;

Foxp3:
                                         (SEQ ID NO: 17)
F-GGCCCTTCTCCAGGACAGA;

(SEQ ID NO: 18)
R-GCTGATCATGGCTGGGTTGT.
```

Flow cytometry: Cells were pre-blocked with Fc block (CD16/CD32) antibody prior to immunostaining. The following fluorochrome conjugated antibodies were used: anti-B7.1, B7.2, CD11c, MHC-II, CD45, as well as their respective isotype control antibodies (eBiosciences); anti-Hsp70 (Novus Biologicals) and anti-TRP1 (Abcam). Dead cells were detected by using a UV LIVE/DEAD® Fixable Dead Cell Stain Kit (Invitrogen). The immunostained cells were analyzed on an LSR-II Flow Cytometer (Becton Dickinson), and post-acquisition analyses were carried out using the FlowJo software.

Example 2

The hypoxic tumor microenvironment generates oxidative Endoplasmic Reticulum (ER) stress, resulting in protein misfolding and unfolded protein response (UPR). UPR induces several molecular chaperones including heat-shock protein 90 (HSP90), which corrects protein misfolding and improves survival of cancer cells and resistance to tumoricidal therapy although prolonged activation of UPR induces cell death. The HSP90 inhibitor, 17AAG, has shown promise against various solid tumors, including prostate cancer (PC). However, therapeutic doses of 17AAG elicit systemic toxicity. Herein a new paradigm is disclosed where the combination therapy of a non-ablative and non-invasive low energy focused ultrasound (LOFU) and a non-toxic, low dose 17AAG causes synthetic lethality and significant tumoricidal effects in mouse and human PC xenografts. LOFU induces ER stress and UPR in tumor cells without inducing cell death. Treatment with a non-toxic dose of 17AAG further increased ER stress in LOFU treated PC and switched UPR from a cytoprotective to an apoptotic response in tumors resulting in significant induction of apoptosis and tumor growth retardation. LOFU-induced ER stress makes the ultrasound-treated tumors more susceptible to chemotherapeutic agents, such as 17AAG. LOFU-induced chemosensitization is a novel therapy that can be used on tumors, for example, locally advanced and recurrent tumors.

Treatment schema and toxicity of LOFU and 17AAG therapy: For each grid location, LOFU was administered for 1.5 seconds at 100% duty cycle, acoustic power of 3 W, and using ultrasound frequency of 1 MHz. This protocol yielded an approximate in situ spatial-peak temporal-average acoustic intensity of 270 W/cm$^2$, resulting in estimated average intra-tumoral temperature elevation of 3.2° C. Post-treatment, there were no signs of normal tissue toxicity such as alopecia, thermal damage, or skin wounds. Preclinical pharmacokinetic studies in mice have shown 17AAG to be widely distributed and to undergo extensive hepatic metabolism. Systemic administration of 17AAG is known to be associated with significant hepatotoxicity, characterized by increases in transaminases and bile acids, and drug-related histopathologic lesions in the gallbladder, common bile duct, and gastrointestinal tract. Therefore, we determined the dose of 17AAG that was nontoxic for our therapy. C57Bl/6 mice were treated with intraperitoneal injections of 17AAG (25-75 mg/kg body weight) three times a week. Control mice were injected with equal volume of the vehicle DMSO, which was used to solubilize 17AAG. Although higher doses of 17AAG (50-75 mg/kg of body weight) treatment achieved significant tumor growth retardation compared to untreated control (untreated tumor. 1879±98.65 mm$^3$ versus 17AAG 75 mg/kg b.w., 485±24.25 mm$^3$, $p<0.003$ and 50 mg/kg b.w., 964 mm$^3$, $p<0.007$, respectively), Kaplan Meier survival analysis showed death in 50% of mice after 21 days of treatment with a dose of 75 mg/kg of body weight.

Figures 7A, 7B, 7C, 7D, 7E, 7F, 7G:
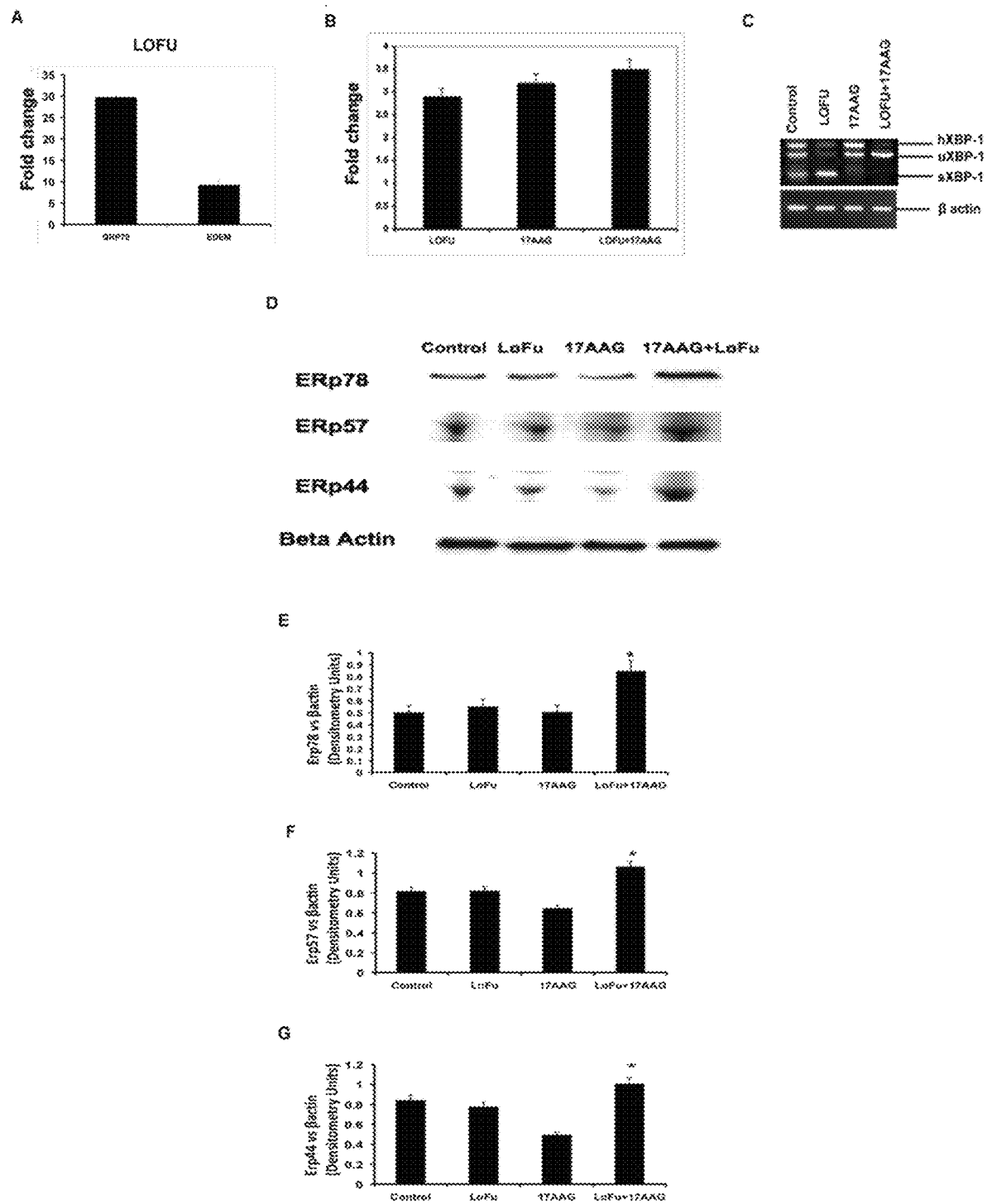
FIG. 7A-7G: LOFU induces UPR. 7A. LOFU increases the expression of Bip/Grp78 and MEM mRNAs. Real Time-PCR analysis of RNA isolated from LOFU-treated RM1 tumors showed 29.73±0.56 fold increase in Bip/Grp78 and 9.27±1.18 fold increase in EDEM mRNA level compared to untreated control. 7B. LOFU increases the expression of IRE1α mRNA by 2.8±0.4 folds. Real Time-PCR analysis demonstrates that LOFU induced increase in the IRE1α expression did not alter with the 17AAG treatment. 7C. LOFU induced the splicing of XBP1 mRNA 17AAG treatment inhibits the splicing of XBP1. XBP1s, XBP1h, and XBP1u denote the spliced, hybrid, and un-spliced forms of XBP1, respectively. 7D-G. LOFU+17AAG combination therapy prolongs ER stress in RM1 tumor cells. Western blot and bar chart showing that the expression of ERP78 (7D & 7E), ERP57 (7D & 7F), and ERp44 (7D &. 7G) proteins was induced in combination treatment group.

A low dose of 17AAG that was found to be nontoxic was 25 mg/kg in C57Bl/6 mice and 14 mg/kg in Balb/c nude mice. Thus, these dose levels were selected for the current study. The goal was to combine two therapies that are nontoxic, albeit subtherapeutic, and examine whether the combination can be therapeutic. Combination treatment of LOFU+17AAG amplifies ER stress: Accumulation of misfolded proteins in the ER induces a stress response with induction of chaperone proteins that help in correction of protein misfolding. To detect the level of ER stress, the expression levels of ER chaperones, ERp44, ERp57, and ERp72 were quantitated among different treatment groups. ERp44 is responsible for oxidative protein folding [69]. ERp57 is an ER resident thiol disulfide oxidoreductase while Erp72 is a disulfide isomerase. All these proteins participate in the protein folding machinery of the ER. Compared to tumor tissues from animals that received no treatment or LOFU or 17AAG alone, immunoblot analysis demonstrated a significant increase in the expression of ERp78 ($p<0.03$, FIGS. 7D & 7E), ERp44 ($p<0.05$, FIGS. 7D & 7G), and ERp57 ($p<0.04$, FIGS. 7D & 7F) protein levels in tumor tissues following combination treatment with LOFU+17AAG. This suggests that 17AAG mediated inhibition of HSP90 may increase the unfolded protein burden in the ER, thereby prolonging ER stress.

Figures 8A, 8B, 8C, 8D, 8E:
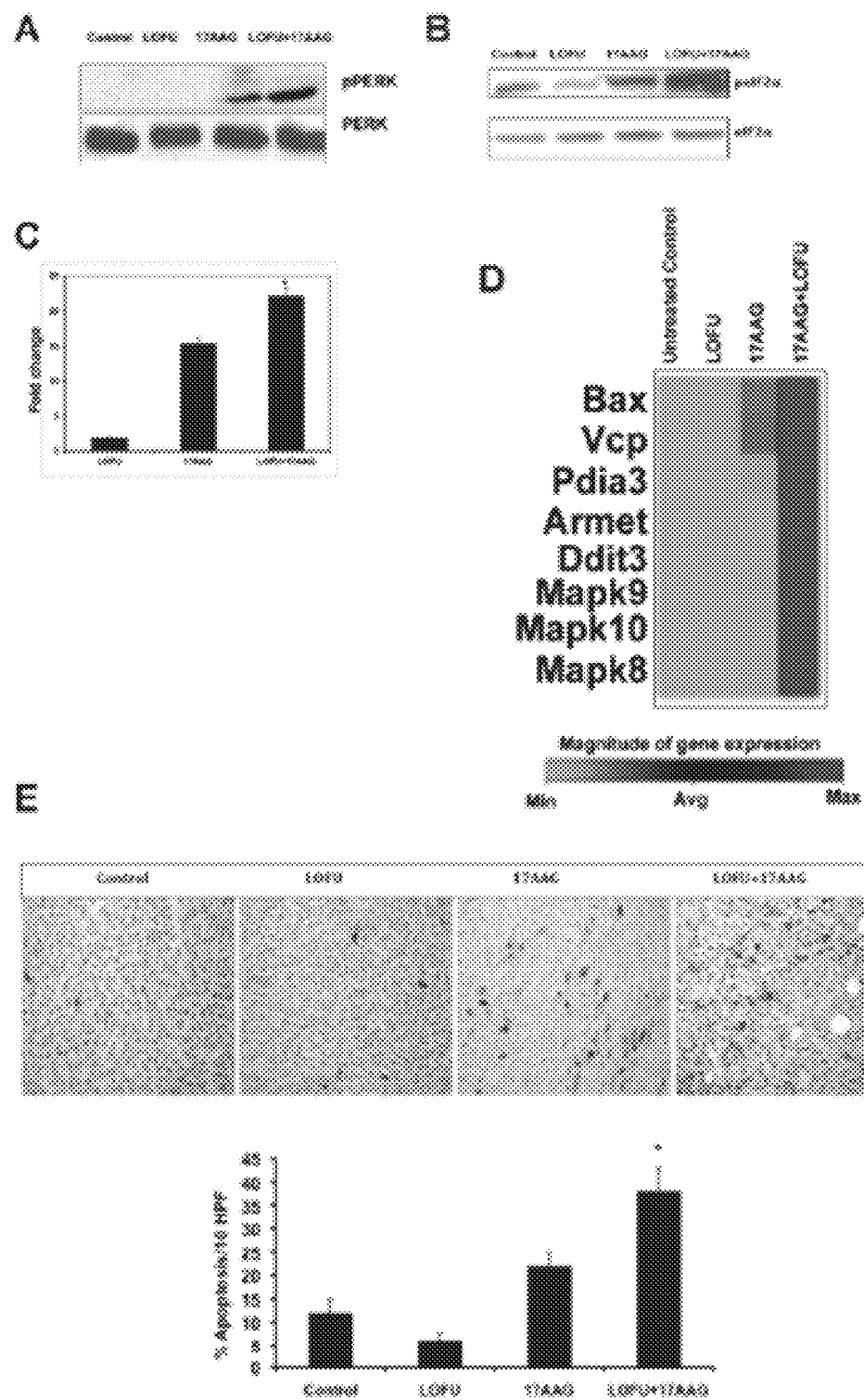
FIG. 8A-8E: LOFU+17AAG activates pro-apoptotic pathways of UPR and induces apoptosis in tumor cells. 8A & 8B. Western blot of pPERK (8A) and peIF2a (8B). LOFU+17AAG activates PERK by phosphorylation of PERK (pPERK), which further induces the phosphorylation of eIF2a phosphorylation (peIF2a). 8C. Real Time-PCR analysis of CHOP mRNA. There was a 25±1.3-fold increase in CHOP transcript in LOFU+17AAG treated group, compared to control. 8D. Real Time-PCR array of RNA isolated from LOFU+17AAG treated tumors. Heat map analysis showed that LOFU+17AAG treatment group increased the transcript level of apoptotic genes several folds compared to untreated control or LOFU groups. 8E. TUNEL staining. Immunohistochemical staining showed predominantly tunel positive cells in LOFU+17AAG treatment group, compared to control or LOFU group. Note that 17AAG alone also induced apoptosis in tumor tissue that was augmented by LOFU.

LOFU+17AAG activates pro-apoptotic pathways of UPR and induces apoptosis in mouse and human prostate cancer tissues: ER stress activates the three arms of UPR at the same time, thereby producing antagonistic cytoprotective and apoptotic signals at the same time. The fate of the cell depends upon the ability of its protein correction machinery to lower the ER stress, thereby attenuating the UPR. If ER stress persists, the cytoprotective pathways are eventually overwhelmed with the chronic activation of PERK-mediated apoptotic pathways causing cellular demise. Since phosphorylation of PERK at Thr980 serves as a marker for its activation status, we performed immunoblot analysis that showed a significant increase in pPERK levels in tumor tissue following treatment with 17AAG (FIG. 8A). Phosphorylated PERK levels were absent in untreated and LOFU-treated tumors. However, combination treatment of LOFU+17AAG exhibited the highest levels of PERK phosphorylation (FIG. 8A).

Since prolonged PERK activation attenuates protein synthesis in response to ER stress through the phosphorylation of translation initiation factor eIF2a at serine 51, the levels of phosphorylated eIF2α were determined. Treatment of RM1 tumors with 17AAG induced phosphorylation of eIF2α over the basal levels in untreated controls. LOFU treatment resulted in marginal reduction of phosphorylated eIF2α levels. However, the highest levels of phosphorylated eIF2α, were seen in tumors that received combination treatment with LOFU+17AAG (FIG. 8B), corroborating with highest activation of PERK phosphorylation in these tumors compared to other groups.

Although phosphorylated eIF2α decreases the translation of most cellular proteins, including pro-survival and anti-apoptotic proteins, it increases the translation of a transcription factor, ATF4 that is responsible for inducing the transcription of pro-apoptotic genes, such as, CCAAT/enhancer-binding protein homologous protein (CHOP), thereby preparing the cell for programmed cell death in case the misfolded proteins are not repaired and ER stress persists [71]. As expected, LOFU treatment failed to induce CHOP levels (1.6±0.7 fold) over untreated controls. In contrast, treatment with 17AAG alone induced CHOP transcript levels to 14.8±2 fold, which was further increased to 25±1.3 fold ($p<0.006$) in the combination treatment group of LOFU+17AAG, compared to untreated controls (FIG. 8C).

In order to examine whether downstream apoptotic genes are expressed following CHOP induction by the combination therapy of LOFU+17AAG, a mouse UPR gRT-PCR Array was used on total RNA isolated from tumor tissues of various treatment groups. Heatmap analysis demonstrated that pro-apoptotic target genes, such as Bax, Vcp, Pdia3, Armet, edit 3, Mapk8, Mapk9, and Mapk10 were induced several folds following combination therapy with LOFU+ 17AAG compared to untreated controls (FIG. 8D). There was minimal induction of pro-apoptotic genes upon treatment with LOFU alone or 17AAG alone. This result indicates that the combination therapy of LOFU+17AAG activates PERK, induces CHOP, and switches on the pro-apoptotic pathway of the UPR. Indeed, TUNEL staining demonstrated that LOFU induced minimal apoptosis over untreated controls. Treatment with 17AAG induced significant apoptosis in prostate tumors, which was further increased by LOFU ($p<0.004$) (FIG. 8E). Thus, 17AAG-mediated inhibition of HSP90 and activation of CHOP by the combination of LOFU+17AAG switched on apoptotic cell death of prostate tumors, LOFU-17AAG inhibits Chaperone Mediated Autophagy (CMA) in tumor cells.

Figures 9A, 9B, 9C:
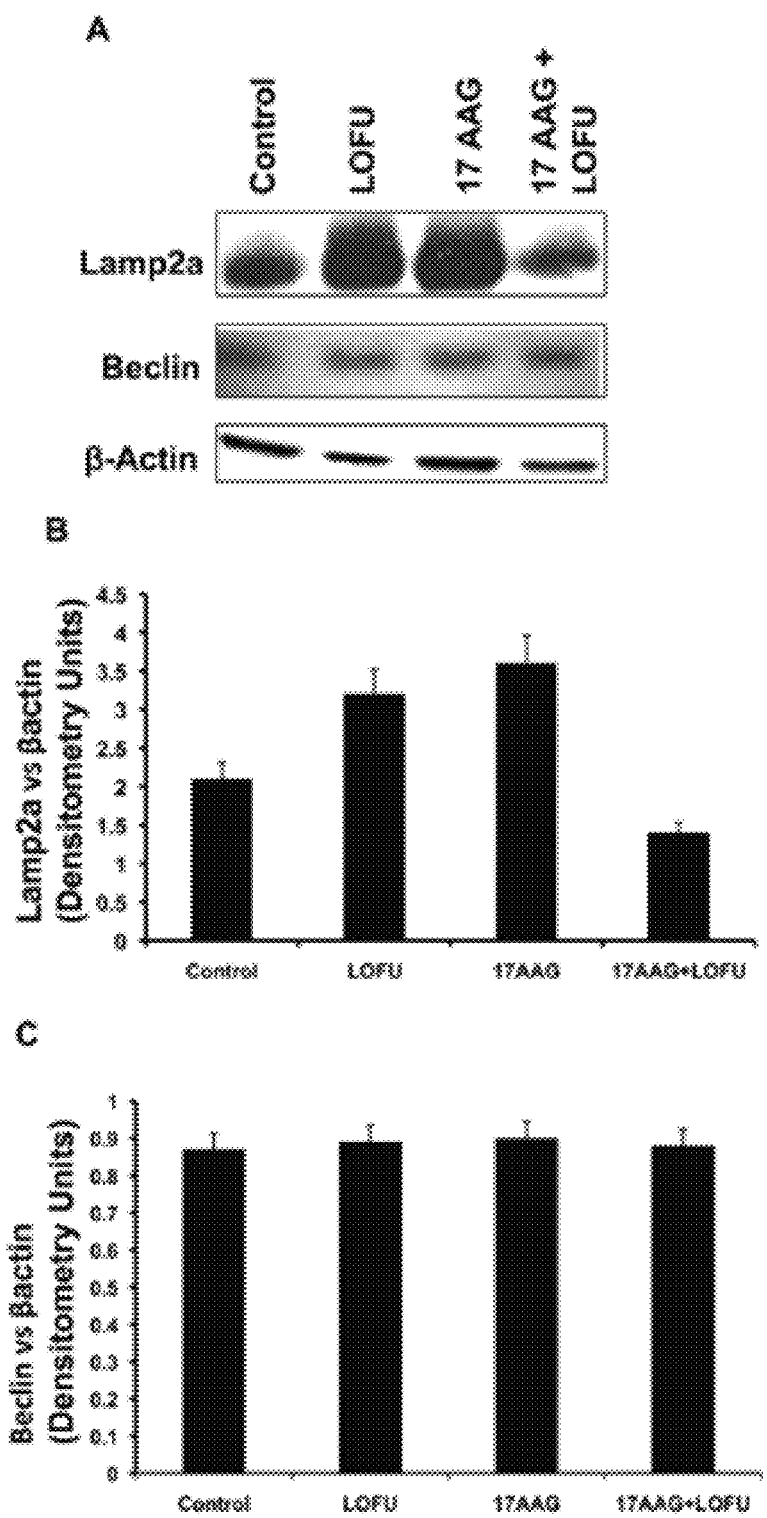
FIG. 9A-9C: LOFU+17AAG treatment inhibits Chaperone Mediated Autophagy (CMA) in RM1 tumor cells. (9A & 9B) Immunoblot analysis showed several fold downregulation of SMA marker LAMP2a expression level in combination treatment group. Treatment with either LOFU or 17AAG upregulates the LAMP2a expression level. (9A & 9C) Combination treatment of LOFU and 17AAG did not alter the expression level of Beclin, a macroautophagy marker.
Figure 10A:
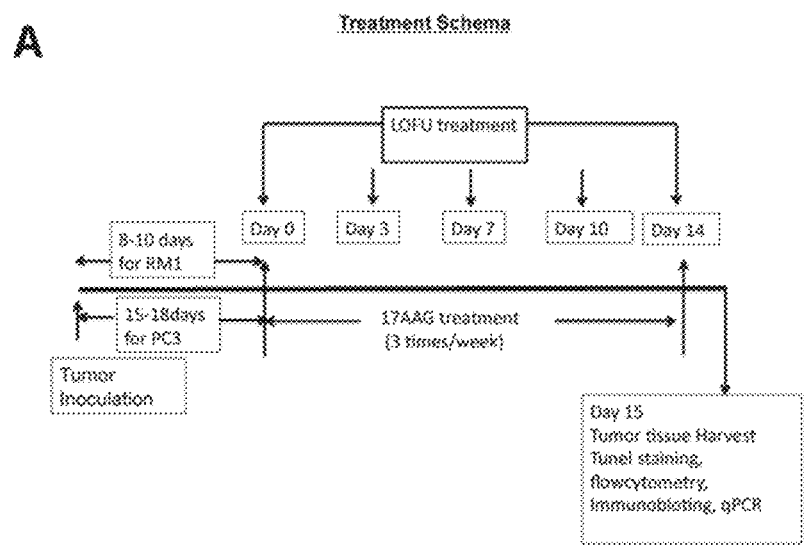
FIG. 10A-10C: Tumor growth retardation of murine and human prostate tumors after LOFU+17AAG treatment. 10A. Treatment schema. Palpable tumors were treated with LOFU every 3-4 days for five fractions administered over two weeks. Animals received 17AAG three times a week during this time. Tumors were harvested 24 hours after the last fraction of LOFU. 10B. RM1 tumor. In C57B16 mice, LOFU+17AAG combination treatment reduced RM1 tumor growth significantly ($p<0.004$), compared to controls. Note that either LOFU or 17AAG alone failed to control tumors significantly. LOFU sensitized the effects of a low dose (25 mg/kg of body weight) 17AAG. 10C. PC3 tumor. In BalbC nu/nu mice LOFU+17AAG combination treatment showed significant reduction in PC3 tumor growth ($p<0.007$).
Figure 10B:
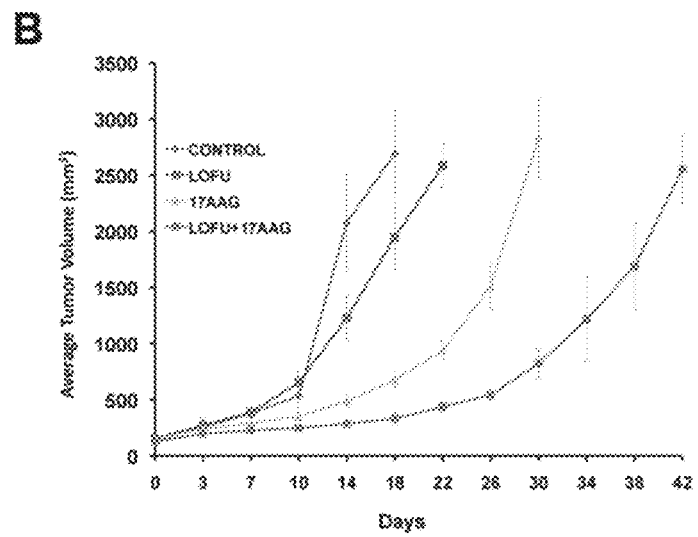
Figure 10C:
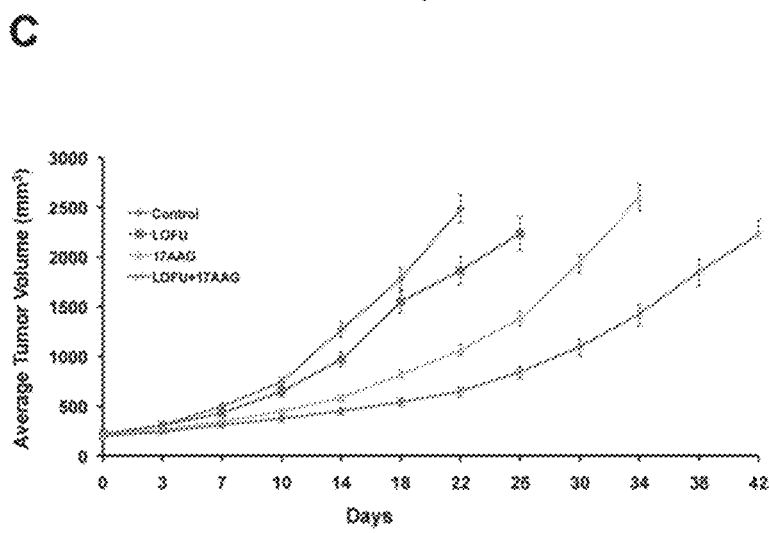

Degradation of misfolded proteins is mediated by the proteosomal pathway and autophagy. Autophagy has been implicated in the tumorigenesis process in a context-dependent role, where it might provide amino acids and other essential nutrients to the metabolic pathways of hypoxic tumors that are nutrient deprived [72]. Indeed, an increase in CMA activity has been described in a wide variety of human tumors and CMA has been implicated in survival, proliferation, and metastases of tumor cells [73]. Therefore, the levels of two key proteins participating in autophagy were quantitated, Beclin, a marker of macroautophagy, and LAMP-2A lysosomal receptor, a marker of CMA in the tumor tissues of various treatment cohorts. As shown in FIG. 10, Beclin levels remain unchanged with LOFU or 17AAG or the combination therapy (FIG. 9A 9C), indicating that macroautophagy was not altered with ultrasound therapy. However, LOFU alone or 17AAG alone induced the expression of LAMP-2A (FIGS. 9A & 9B), indicating a compensatory increase in CMA after therapies that increase the burden of misfolded proteins in the ER. Interestingly, the combination of LOFU+17AAG inhibited the levels of LAMP-2A below the basal levels seen in these tumors. This suggests that the combination therapy reduces the growth of tumor cells and induces apoptosis by increasing ER stress while suppressing CMA.

LOFU sensitizes human and murine prostate cancer grafts to non-toxic low doses of 17AAG: Treatment with LOFU alone or low dose of 17AAG (25 mg/kg body weight) alone did not show any normal tissue toxic effect but failed to inhibit tumor growth. However, combination therapy of LOFU+17AAG reduced the growth of murine RM1 tumors (FIG. 10B). The average estimated tumor growth is 5% ($p<0.0001$), 9% ($p<0.0001$) and 11% ($p<0.0001$) slower in LOFU, 17AAG and LOFU+17AAG cohort compared to control group. The median time to achieve tumor size 2000 mm$^3$ in control, LOFU, and LOFU+17AAG were 18, 22, and 42 days, respectively. All the animals in 17AAG group achieved the size within the interval of 26-30 days.

A similar degree of chemosensitization was observed in human PC3 tumors in BalbC nu/nu mice upon application of LORI together with low non-toxic dose of 17AAG (14 mg/kg of body weight), achieving significant tumor growth retardation ($p<0.007$) (FIG. 5C) without any immediate adverse side effects.

Figures 11A, 11B, 11C, 11D, 11E, 11F:
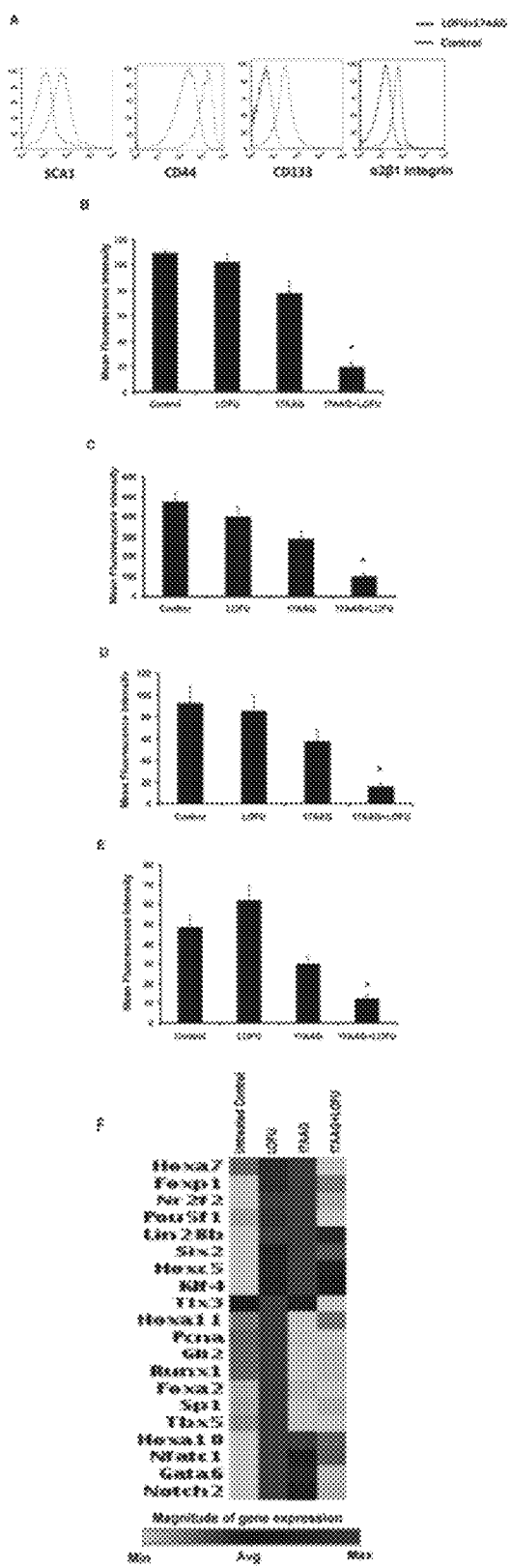
FIG. 11A-11F: LOFU+17AAG treatment reduces the expression of prostate cancer stem cell markers in RM1 cells. Flow cytometry of isolated RM1 tumor cells showed significant decrease in SCAT (11A & 11B), CD44 (11A & 11C), CD133 (11A & 11D), and α2β1 integrin (11A & 11E) cell surface expression on RM1 tumor cells after LOFU+17AAG treatment. (11F) qRT-PCR array followed by heat map analysis showed that LOFU+17AAG combination treatment group down-regulates the mRNA levels of stem cell transcription factors.

LOFU+17AAG treatment reduces the prostate cancer stem cell population in tumor tissue: The effect of LOFU+17AAG-induced ER stress on PC stem/progenitor population was evaluated by flow cytometric analysis of PC stem/progenitor cell surface markers [24, 25]. The percentage of cells expressing cell surface SCA1 (FIGS. 11A & 11B) ($p<0.004$), CD44 (FIGS. 11A & 11C) ($p<0.003$), CD133 (FIGS. 11A & 11D) ($p<0.007$), and α2β1 integrin ($p<0.005$) (FIG. 11A &. 11E) was significantly decreased in the combination treatment group, compared to control or single treatment cohort Mean fluorescence intensity (MFI) of all these markers remained unaltered in all the three groups. qRT-PCR array of stem cell transcription factors demonstrated increase (>2 folds) in mRNA levels of Tlx3, Hoxa11, Pcna, Gli2, Runx1, Foxa2, Sp1, Tbx5, Hoxa10, Nfatc1, Gata6, and Notch2 (FIG. 11F), indicating that LOFU induces a PC stem cell transcription signaling. Treatment with 17AAG also increased the expression of some transcription factor mRNAs, such as FoxP1, Nrf2f, and Pou5f1 that were present in LOFU-treated tumors. However, tumor treated with LOFU+17AAG down-regulated the expression of these genes, suggesting that maximization of ER stress by the combination treatment might reduce the PC stem/progenitor cell population in tumors.

Discussion

The results demonstrate that the LOFU and chemotherapy combination therapy reprograms the expression of pro-apoptotic genes in tumors and induces massive apoptosis in tumor xenografts, resulting in significant tumor growth retardation of mouse and human PC tumors. The effect of LOFU can ameliorate resistance to a chemotherapy, and chemosensitization can be effected.

Methods and Materials

Animals

Five- to six weeks-old male C57Bl/6 (NCI-Fort Dietrich, MD, USA) mice and athymic nude (BalbC nu/nu mice, Jackson Laboratory, Bay Harbor, ME, USA) mice were maintained ad libitum and all studies were performed under the guidelines and protocols of the Institutional Animal Care and Use Committee of the Albert Einstein College of Medicine.

Tumor Model and Treatment

C57Bl/6 and BalbC nu/nu mice were injected subcutaneously with $1\times10^5$ RM-1 (murine prostate cancer cell line) and $1\times10^6$ PC3 (human prostate cancer cell line) cells on the flank, respectively. Approximately 10 days later, the tumor became palpable (3-5 mm in diameter), whereupon LOFU treatment was initiated. Mice were divided into 4 groups (n=5/group) receiving no treatment, LOFU, 17AAG (InvivoGen, San Diego, CA, USA), and 17AAG+LOFU. Palpable tumors were treated with LOFU every 3-4 days for five fractions administered over two weeks. Animals received 17AAG three times a week during this time. Tumor volume measurements were performed twice weekly using Vernier calipers along with simultaneous physical assessment of signs of systemic toxicity (malaise and diarrhea).

LOFU System

A therapy and imaging probe system (TIPS, Philips Research North America, Briarcliff Manor, NY, USA) was utilized for all ultrasound exposures. The system includes an 8-element spherical shell annular array transducer (80 mm radius of curvature, 80 mm aperture), as well as a motion stage to allow for transducer movement and accurate positioning. The transducer was operated at 1.0 MHz, resulting in a focal spot approximately 1.5 mm in diameter and 12 mm in length (−6 dB of pressure). [12,13])

LOFU Treatment Protocol.

On treatment day, the animals were anesthetized with ketamine and xylazine (7:1 mg/ml for 100 1/mouse, i.p.). Once positioned for therapy, the tumor was acoustically coupled to the TIPS system using degassed water and ultrasound gel.

Ultrasound exposure parameters were as follows: acoustic power of 3 W and a duty cycle of 100%, yielding an approximate in situ spatial-peak temporal-average intensity (Ispta) of 270 W/cm$^2$ at a sonication depth of 3 mm in tissue, assuming an attenuation coefficient of 0.5 dB cm-1 MHz-1 [75]. Ultrasound exposures were delivered to the tumor using a 2 mm grid pattern extending over the entire tumor volume. Prior to LOFU, the tumor volume was measured to calculate the grid size for the particular treatment. The duration of LOFU exposure at each grid point was 1.5 s, after which the transducer was automatically positioned over the next grid point and the procedure repeated until the entire tumor volume was covered. This yielded a non-uniform energy delivery to the tumor.

In Vitro Temperature Rise Estimation.

Estimation of intra-tumoral temperature by invasive means could undesirably modulate the therapeutic response of the combination treatment. Therefore, to estimate intra-tumoral temperature elevation using the above described setup and therapy protocol, the ultrasound exposures were performed in a 6 mm×6 mm area within a tissue-mimicking phantom, into which a T-type thermocouple (diameter 200 µm) was embedded at a depth of 3 mm. These in vitro exposures were repeated 5 times and the results averaged.

Detection of Apoptosis In Situ

Apoptotic cells were detected in situ by performing TUNEL (TdT—mediated digoxigenin labeled dUTP nick end labeling) staining. Briefly, paraffin embedded sections were de-paraffinized, rehydrated through graded alcohols, and stained using an ApopTag kit (Intregen Co, Norcross, GA, USA). The apoptotic rate in tumor cells was quantified by counting the percent of apoptotic cells in each high power field.

Immunoblot Analysis 24 hr post-LOFU the tumor cells were harvested, washed with phosphate-buffered saline, and lysed using TPER (Thermo Fisher Scientific, Rockford, IL, USA). Cell lysates were subjected to SDS-PAGE, transferred to polyvinylidene difluoride membrane, and immunoblotted with primary antibodies against PERK, pPERK, eIF2,peIF2, ERp72, ERp44, ERp57, Beclin (Cell signaling, Danvers, MA, USA), Lamp2a (Abcam, Cambridge, MA, USA), and horseradish per-oxidase-conjugated secondary antibody. The blots were developed using the ECL kit (GE Healthcare, Piscataway, NJ, USA). Densitometric analysis of immunoreactive bands of each blot was photographed and then images were digitized and analyzed by using Gel Doc XR system (Bio-Rad, Hercules, CA, USA).

Real Time PCR analysis of UPR target genes 24 hr after LOFU treatment the RM1 tumor cells were lysed using RLT buffer mixed with 1% betamercaptoethanol from RNeasy Mini Kit (Qiagen, Valencia, CA, USA).

Qiagen's protocol for the RNeasy Mini Kit with on-column DNA digestion was used to isolate RNA from the tumor lysates. The RNA samples were stored at −80° C., prior to further use. Isolated RNA was subjected to cDNA synthesis using the SuperScript™ First-Strand Synthesis System (Invitrogen, Grand Island, NY, USA). The splicing of XBP1 RNA was detected using the following primer pair 5'-ACTCGGTCTGGAAATCTG-3' (SEQ ID NO:19) and 5'-TAGCCAGGAAACGTCTAC-3' (SEQ ID NO:20) (Fisher Scientific, Pittsburgh, PA, USA) [77]. Real time PCR was performed in Light Cycler real time PCR machine (Bio Rad Laboratories, Hercules, CA, USA) using the Absolute QPCR SYBER Green Mix (ABgene, Rochester, NY, USA) according to the standard ABgene protocol. To check for primer amplification specificity, a melting curve was generated at the end of the PCR and different samples containing the same primer pair showed matching amplicon melting temperatures.

Primers used for real time PCR included GRP78 5'TTGCTTATGGCC TGGATAAGAGGG3' (SEQ ID NO:21) and 5'TGTACCCTTGTCTTCAGCTGTCAC3' (SEQ ID NO:22); EDEM 5' TCATCCGAGTTCCAGAAAGCAGTC 3' (SEQ ID NO:23) and 5' TTGACATAGAGTGGAGGGTCTCCT 3' (SEQ ID NO:24) (Fisher Scientific). All the qRT-PCR and Real time PCR experiments were repeated three times. The qRT-PCR and PCR array for apoptosis genes and stem cell transcription factor were performed by SA Biosciences PCR array system (Frederick, MD, USA) according to manufacturer protocol. In brief, cDNA were prepared from purified total RNA using $RT^2$ First Strand Kit (Qiagen) followed by PCR array using SA Bioscience PCR array kit. Data was analyzed by web based PCR array data analysis software from SA Biosciences.

Flowcytometric Analysis

Flank tumors were treated with LOFU, 17AAG, and LOFU+17AAG in various cohorts. 24 hours after treatment, tumor cells were isolated by collagenase digestion and analyzed by flowcytometry for the expression of prostate cancer stem cell markers, SCA1, CD44, and CD133. Isolated tumor cells were stained with anti-SCA1 conjugated with FITC (BD Biosciences, La Jolla, CA, USA), anti-CD133 conjugated with pacific blue (eBioscience, San Diego, CA, USA) and anti-CD44 conjugated with PE (BD Biosciences, La Jolla, CA, USA). Data acquisition was performed using LSRII (BD Biosciences) and analyzed by FlowJo v.7.1 (Treestar Inc, Ashland, OR, USA) software.

Kaplan-Meier Survival Analysis

Mice survival/mortality in different treatment groups was analyzed by Kaplan-Meier as a function of radiation dose using Sigma-Plot and GraphPad Prism (version 4.0 for OS X, San Diego, CA, USA) software.

Statistical Analysis

For digital images, sampling regions were chosen at random for digital acquisition for data quantitation. Digital image data was evaluated in a blinded fashion as to any treatment. A two-tailed Student's t-test was used to determine significant differences ($p<0.05$) between experimental cohorts with representative standard errors of the mean (SEM).

Figure 12:
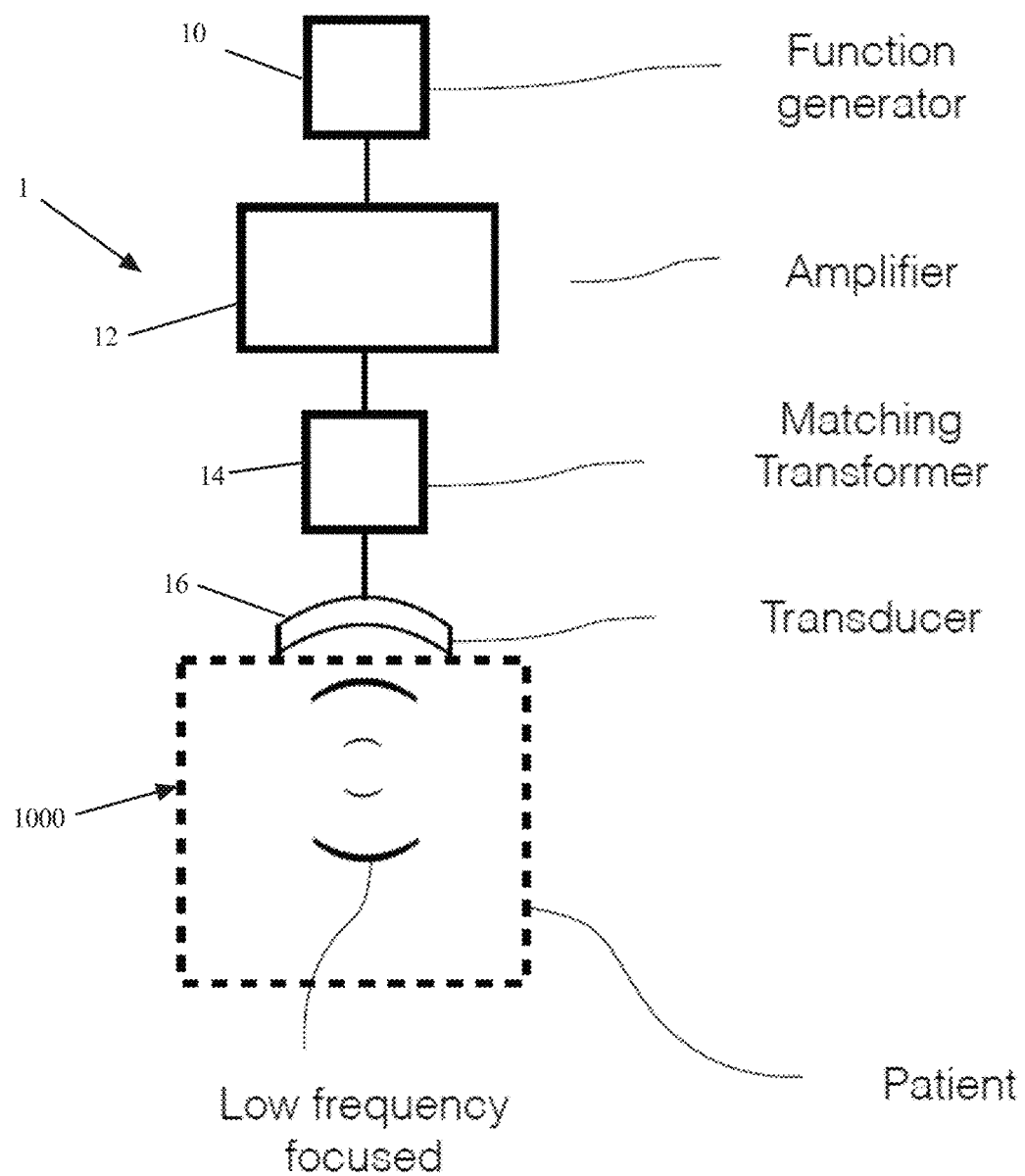
FIG. 12 is a block diagram of an APT device according to an exemplary embodiment of the present invention.

FIG. 12 shows an acoustic priming therapy (APT) device, generally designated by reference number 1, according to an exemplary embodiment of the present invention. The APT device 1 is powered by an electrical power source (not shown) and includes a control system 10, amplifier 12, matching transformer 14 and transducer 16. To provide treatment, the ultrasound transducer 16 may be positioned near or within a region of the patient's body 1000. A clinician may make appropriate adjustments to the frequency and duration of the ultrasound pulses to be delivered by the transducer 16 using a function generator at the control system 10. When the ultrasound transducer 16 is excited, a transmitting surface of the transducer element creates pressure waves in the bodily fluids surrounding the ultrasound transducer 16. The pressure waves then propagate through the fluids and tissues within the patent's body 1000 and ultimately reach the target region, thereby causing a non-ablative, sonic stress to the target tissue. As explained in further detail herein, the sonic stress delivered to the tissue may have many therapeutic uses, and in the case of cancer treatment, for example, such stress of cancer cells in a tumor may result in immunogenic modulation, radio-sensitization and chemo-sensitization. The ultrasound transducer 16 may be repositioned to an adjacent area of the patient's body for further treatment.

The matching transformer 14 provides an impedance transformation between the power supply and ultrasound transducer.

The amplifier 12 generates a transducer driver signal for driving the transducer 16 based on the output signal of the control system 10. In an exemplary embodiment, the amplifier 12 may be a switched resonant power amplifier, an example of which is disclosed in U.S. Pat. No. 7,396,336, the contents of which are incorporated herein by reference in their entirety. In another embodiment, low impedance ultrasound driver-transducer systems can be employed [78].

The transducer 16 generates acoustic power between 10 and 1000 W/cm$^2$ spatial peak temporal average intensity ($I_{spta}$) in a treatment zone. The ultrasound is applied continuously for a time in the range of from 0.5 to 5 seconds, wherein the frequency is in the range of 0.01 to 10 MHz. In some embodiments the minimum diameter of any ultrasound beam in the treatment zone is about 1 cm.

Figure 13:
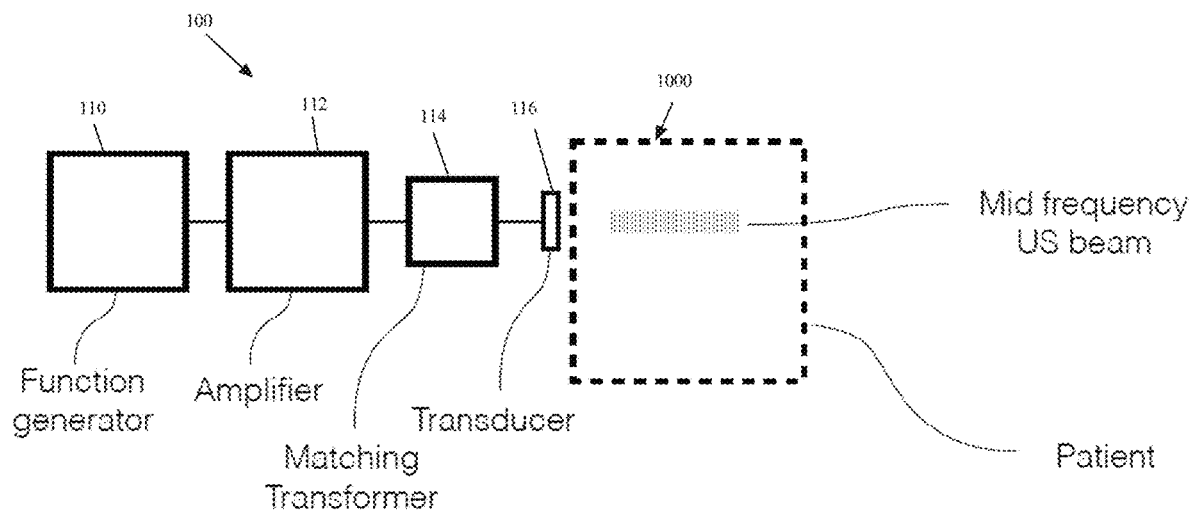
FIG. 13 is a block diagram of an APT device according to another exemplary embodiment of the present invention.

In the embodiment shown in FIG. 12, the frequency of ultrasound generated by the APT device 1 is in the range of about 10 KHz to about 300 KHz. However, the APT device according to the present invention may generate higher frequencies such as, for example, frequencies in the range of about 300 KHz to about 3 MHz. As shown in FIG. 13, an embodiment of such an APT device, generally designated by reference number 100, may include a control system 110, amplifier 112, matching transformer 114 and transducer 116, such components having the same function and structure as previously described with reference to FIG. 12. In embodiments, the transducer 116 may be a flat or concave piston-type transducer comprised of single or multiple elements that convert another type of energy to acoustic energy.

Figure 14:
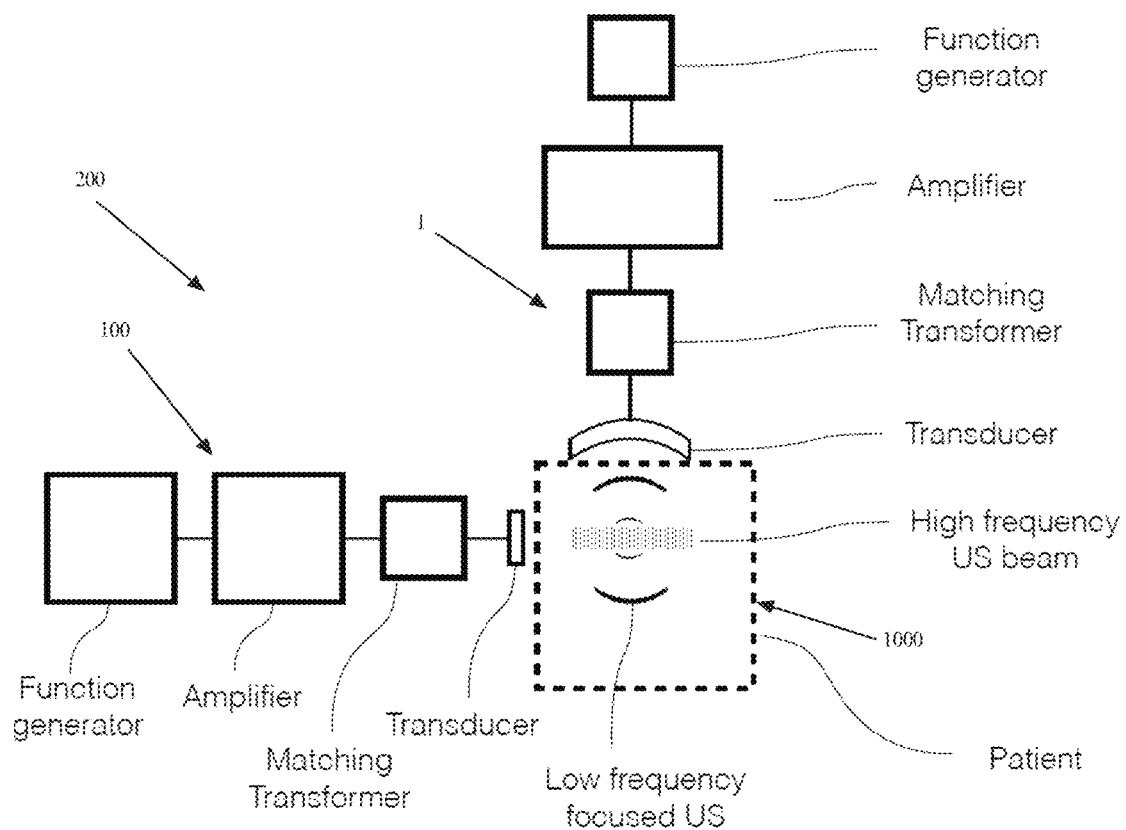
FIG. 14 is a block diagram of an APT device according to another exemplary embodiment of the present invention.

As shown in FIG. 14, the APT device 1 and APT device 100 may be integrated into a single system, generally designated by reference number 200, to provide improved efficacy and/or lower overall energy input. The integrated system 200 provides focused low frequency and collimated high frequency beams for APT treatment. In some embodiments the low frequency ultrasound is substantially focused according to what is achievable for a given frequency or range of frequencies and the mid frequency is collimated. In some embodiments the transducer used to produce the low frequency is concave and the transducer used to produce the mid frequency is planar.

Figure 15:
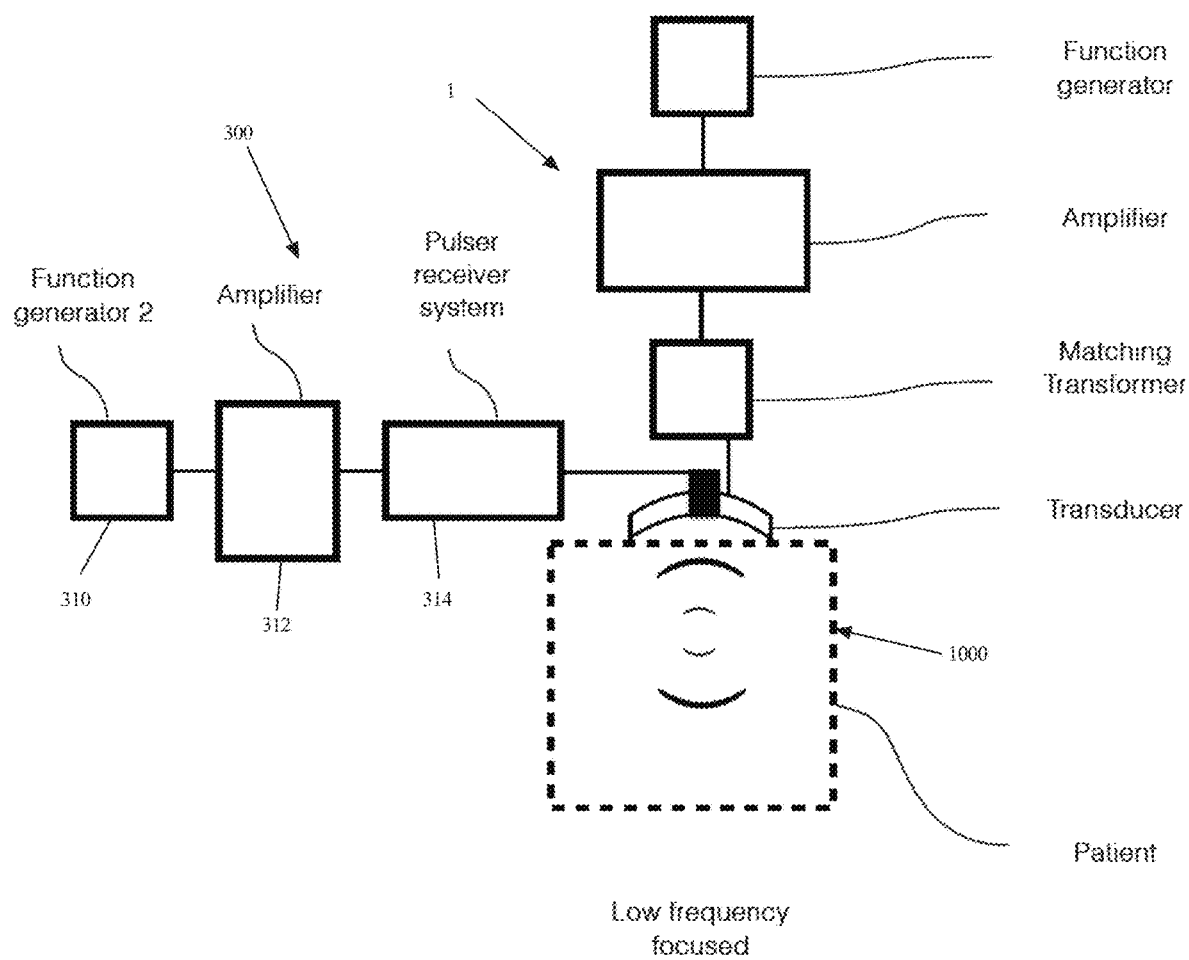
FIGS. 15-17 are block diagrams of APT devices according to exemplary embodiments of the present invention including an integrated ultrasound imaging device.
Figure 16:
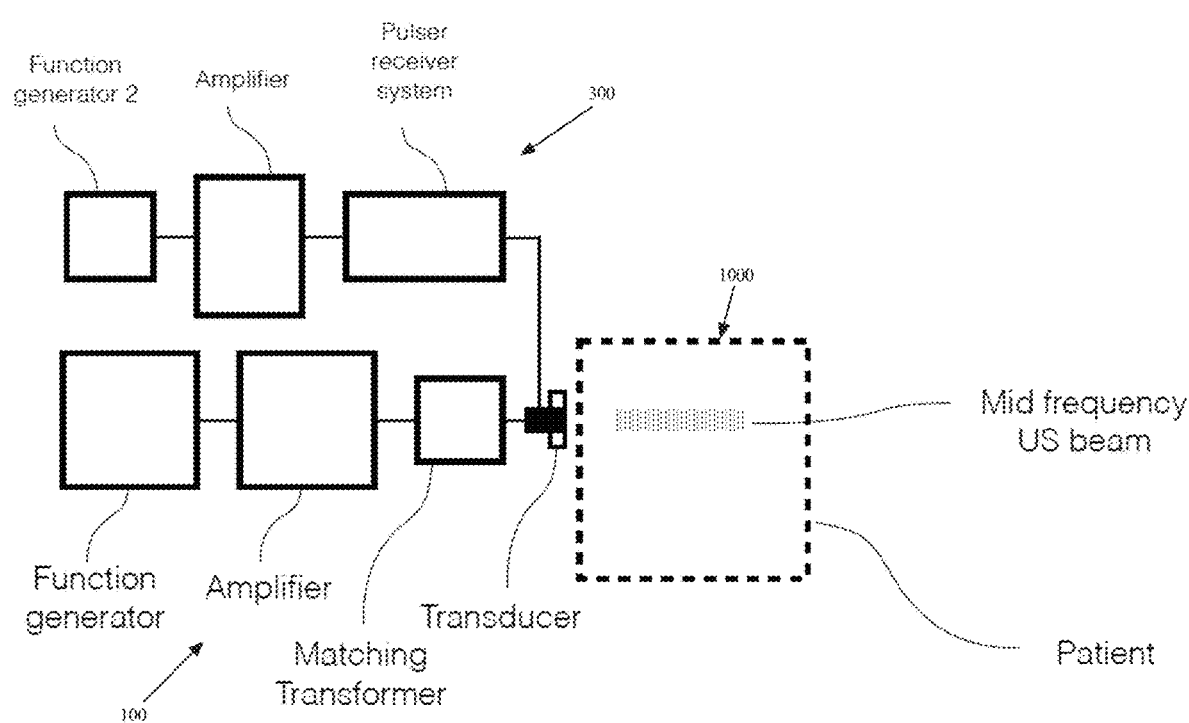
Figure 17:
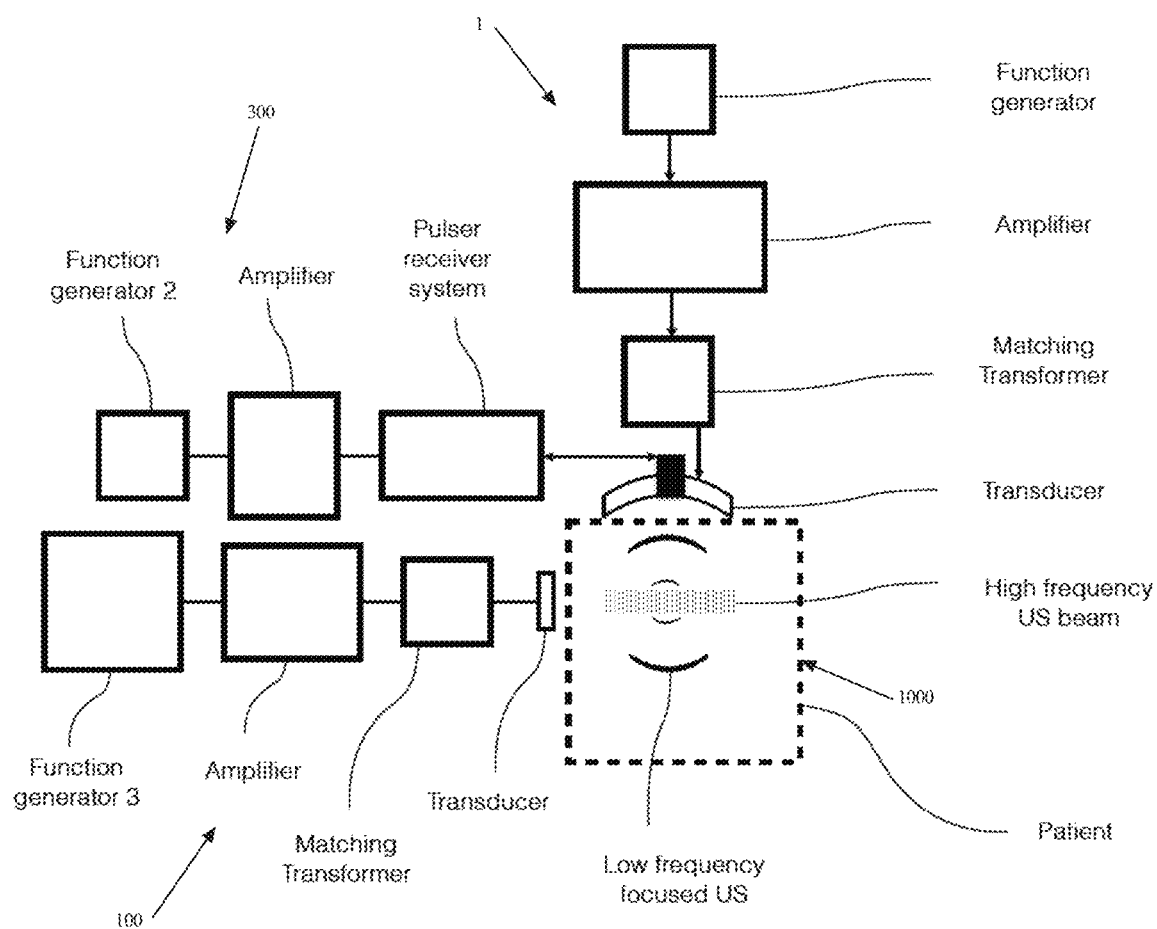

As shown in FIGS. 15-17, the APT device 1, 100, 200 may operate in conjunction with an ultrasound monitoring system, generally designated by reference 300. The ultrasound monitoring system 300 may be powered by an electrical power source (not shown) and includes a control system 310, amplifier 312 and pulse receiver system 314. The ultrasound monitoring system 300 may be used to monitor and/or provide imaging of the target tissue prior to, during and/or after APT treatment, and in particular the pulse receiver system 314 may include a transducer that receives pressure waves reflected from or generated by or from within the target tissue and the amplifier 312 generates electrical signals corresponding to the received pressure waves. The control system 310 generates output based on the electrical signals that can be used by a clinician to determine treatment status and/or other parameters. Although the ultrasound monitoring system 300 is shown as a separate component from the APT device 1, 100, 200, it should be appreciated that the monitoring and APT delivery may be performed by a unitary system.

In some embodiments, the ultrasound monitoring system 300 is used to provide information on the location of tissue to be treated. One or more, non-therapeutic ultrasound transmit and receive sub-systems may be used to monitor APT treatment and the effects of treatment on tissues.

In some embodiments, the data collected and used for planning radiation treatment are also used at least in part for planning ultrasound treatment.

In some embodiments, the data collected for APT treatment planning or APT treatment is used in radiation treatment planning. In some embodiments the data collected for radiation treatment planning is used for APT treatment planning. In some embodiments the data collected during APT treatment is used in radiation treatment planning.

In some embodiments, ultrasound is applied at a lower frequency to treat a particular location or locations identified in part by ultrasound imaging performed at a higher frequency.

Various ultrasound-based imaging and monitoring modalities may be used to monitor power deposition in tissues during APT treatment. In some embodiments, tissue temperature may be monitored via acoustic means [79].

In some embodiments, ultrasound elastography is used to monitor treatment. In some embodiments, harmonic imaging is used to monitor treatment. In some embodiments, thermal strain is measured. In some embodiments, the system is comprised of one or more ultrasound transmit and receive transducer sub-systems used to measure tissue strain. Tissue strain information may be used to aim the treatment ultrasound beams to a desired tissue and, in some embodiments, prior to applying full treatment power to treatment transducers. For example, in one embodiment, power is applied at 10 to 50% of the intended treatment power to one or more of the treatment transducers and strain of the target tissue is measured using ultrasound feedback. APT transducers may be physically or electronically repositioned or more effectively directed to the target tissue based on strain imaging. In some embodiments, full power is applied from one or more transducers, but the time is shorter than that used for therapeutic effect during the strain measurement period until a desired targeting is confirmed.

In some embodiments, thermometry is used to monitor treatment.

Figure 18:
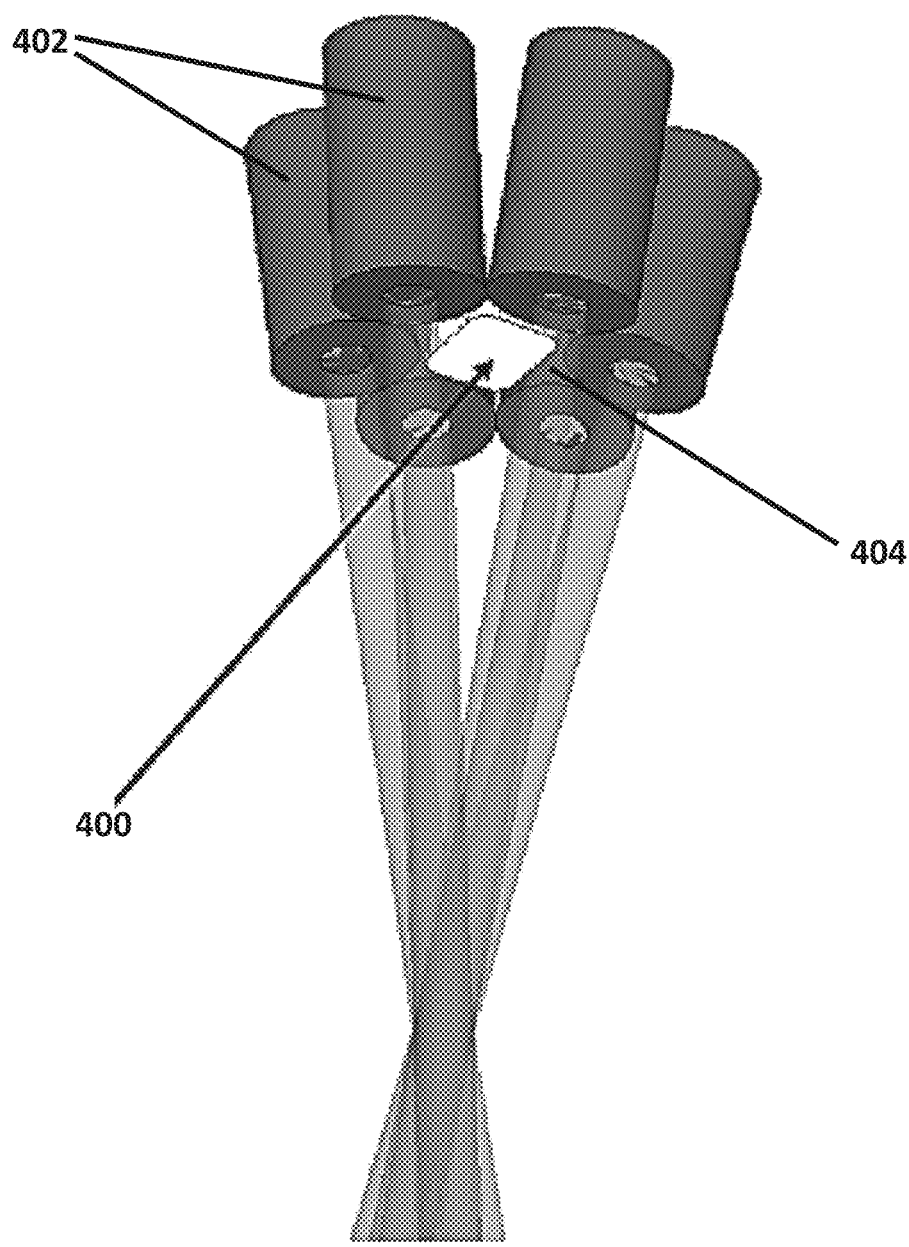
FIG. 18 is a perspective view of a transducer according to an exemplary embodiment of the present invention.

Each transducer of the APT system 1, 100, 200 may be a single transducer or may be an array of a plurality of transducers. FIG. 18 is a perspective view of a transducer, generally designated by reference number 400, according to an exemplary embodiment of the present invention. The transducer 400 includes an array of transducer elements 402. Any number of transducer elements 402 may be sequentially arranged along the azimuth axis. The transducer elements 402 are supported on a backing block 404. Signal leads couple the electrode of each transducer element 402 to transmit and receive circuitry as is well known. The transducer elements 402 convert electrical signals provided by the transmit circuitry to pressure waves.

In some mid frequency embodiments (about 300 KHz to about 3 MHz), two or more ultrasound transducers generate ultrasound beams that intersect within a treatment zone, herein denoted an intersection zone, with each beam having an $I_{spta}$ in the intersection zone in the range of 10 to 500 W/cm$^2$. In embodiments, two transducers generate ultrasound beams that intersect within a treatment zone, with each beam having an $I_{spta}$ in the intersection zone in the range of 50 to 500 W/cm$^2$. In embodiments, three transducers generate ultrasound beams that intersect within a treatment zone, with each beam having an $I_{spta}$ in the intersection zone in the range of 50 to 500 W/cm$^2$.

In some embodiments, the plurality of beams are substantially in phase with one another. In some embodiments, two ultrasound beams emanating from separate ultrasound transducers are substantially in phase and intersect within a treatment zone, and each beam has an acoustic power spatial peak intensity in the intersection zone in the range of 70 to 100 W/cm$^2$ and the ultrasound is applied continuously from 1 to 5 seconds. In some embodiments, three ultrasound beams emanating from separate ultrasound transducers are substantially of the same frequency and in phase and intersect within a treatment zone, and each beam has an acoustic power spatial peak intensity in the intersection zone in the range of 50 to 70 W/cm² and the ultrasound is applied continuously for 1 to 5 seconds.

In some embodiments, beams originating from separate transducers or transducer elements each produce an $I_{spta}$ of approximately 300 W/cm² in the treatment zone.

In some embodiments, at least one transducer diameter and the ultrasound beam emanating from this transducer is substantially larger than the treatment zone. The use of one or more of such large transducer in combination with smaller transducers advantageously allows for less precise aiming of a high power, high volume beam while achieving effective and faster treatments.

In some embodiments, an intense treatment zone is formed where two or more beams cross paths, the intense treatment zone being equal to or greater than about 1 cm perpendicular to the transmitted energy direction and also equal to or greater than about 1 cm parallel to the transmitted direction.

In some embodiments, acoustic pressure applied to a treatment zone from each transducer is 0.1 to 10 MPa.

In some embodiments, the number of transducers that provide the intense ultrasound treatment zone is between 1 and 1000.

In some embodiments, one or more central frequencies are employed during treatment with central frequencies ranging from about 100 kHz to 20 MHz.

In some embodiments, the ultrasound from a given transducer is applied continuously. In some embodiments the ultrasound emanating from a given transducer is applied in pulses with repeating on time units and off time units known as a duty cycle. The duty cycle may be in the range of 1 on time units to 9 off time units.

In some embodiments, the transducers transmit single frequency tones or multi-frequency chirps.

In some embodiments, the transducers are operated sequentially such that the total energy delivered to the target tissue for the entire course of the application is greater than that to surrounding tissues.

In some embodiments, the frequency is swept during application, in part to reduce undesirably high intensity zones in the zones near the transducers.

In some embodiments, the transducer comprising treatment head is mechanically vibrated.

In some embodiments, the transducers are comprised of 2 dimensional phased arrays, annular arrays and/or three-dimensional phased arrays.

In some embodiments, one or more ultrasound transducers are incorporated into one or more endoscopic devices.

The APT treatment systems disclosed herein have a low thermal dose compared to thermal dosing schemes common in hyperthermic and ablative thermal therapies. In some embodiments, the maximum temperature reached in the treatment zone is 45° C. during a treatment that lasts about 2 seconds or less.

In consideration of thermal dose it is expected that therapeutic effect is obtained through a thermal mechanism. While not wishing to be bound by theory, mechanical effects coupled with thermal effects may explain in part observed efficacy of treatments using disclosed devices, systems and methods.

In some embodiments, coupling media is used between the transducers and the patient's body to efficiently transmit ultrasound waves and in some embodiments to provide a desired distance between a transducer and a treatment zone. In some embodiments, the coupling media is circulated to cool the transducer or the patient's body during treatment or both. Separate fluids may be used for purposes of transmitting ultrasound, providing spacing and providing cooling to the patient and system components.

While not bound by theory, APT treatment using the systems described herein can promote the interactions between cells, and between cells and matrix proteins. Interactions between cancer cells and immune cells and interactions between immune cells, for example T Cells and DCs.

In some embodiments, APT treatment may disrupt protein complexes, for example protein folding complexes.

For patients with diseases that benefit from treatment with multiple modalities, permeation of entire targeted treatment zone and lesions within these zones, ease of application and short duration treatments of each modality is desirable.

Various other aspects of the APT treatment device and APT treatment modalities according to exemplary embodiments of the present invention will now be described:

Positioning Apparatus

Figure 19:
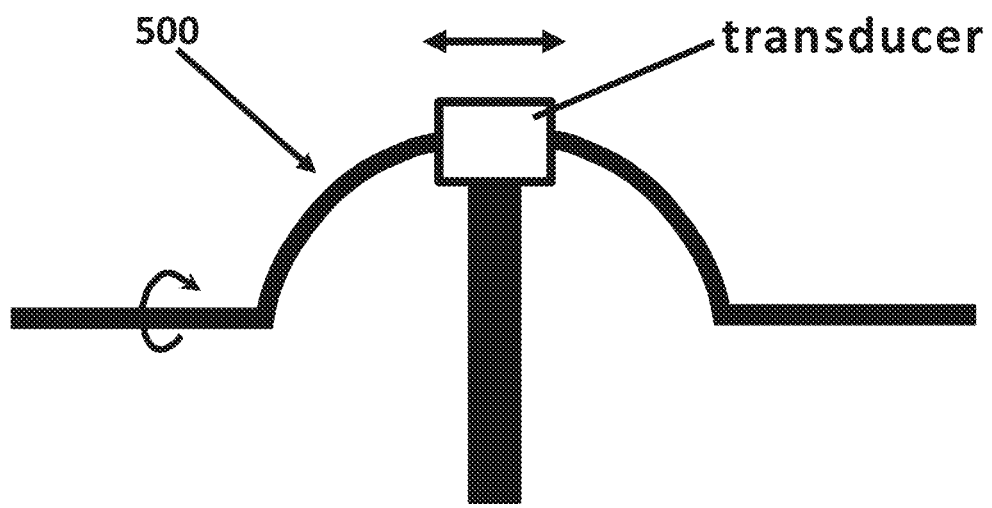
FIG. 19 illustrates a positioning apparatus according to an exemplary embodiment of the present invention.

In some embodiments, transducer applicators are designed so that they may be hand-held by the clinician or care giver. In some embodiments, applicators are mounted to a mechanical positioning device, such as the positioning device 500 illustrated in FIG. 19. The positioning device 500 may be manually manipulated or robotic controlled. In the present embodiment, the positioning device 500 is an arc-shaped rail on which the transducer travels, and in particular the transducer may be attached to a cable-driven carriage that is in turn mounted on the rail. The rail itself may be rotatable so that the transducer can be positioned in three dimensions. The positioning device 500 may be large enough that a patient can fit underneath and within the target range of the transducer. Although FIG. 19 shows only one transducer positioned on the rail, it should be appreciated that more than one transducer may be disposed on the rail and/or other rails may be provided that support one or more other transducers. In some embodiments, a stewart platform, sometimes referred to as a hexapod, may be used in the positioning apparatus. Computer programming may be used to set treatment parameters and operate positioning apparatuses.

Equipment and Patient Cooling

In some embodiments, the treatment system comprises patient cooling mechanisms to cool the skin exposed to ultrasound energy or other energy.

REFERENCES

1. Rabinovich, G. A., Gabrilovich, D., and Sotomayor, E. M. 2007. Immunosuppressive strategies that are mediated by tumor cells. Annu Rev Immunol 25:267-296.
2. Dougan, M., and Dranoff, G. 2009. Immune therapy for cancer. Annu Rev Immunol 27:83-117.
3. Uyttenhove, C., Pilotte, L., Theate, I., Stroobant, V., Colau, D., Parmentier, N., Boon, T., and Van den Eynde, B. J. 2003. Evidence for a tumoral immune resistance mechanism based on tryptophan degradation by indoleamine 2,3-dioxygenase. Nat Med 9:1269-1274.
4. Thomas, D. A., and Massague, J. 2005. TGF-beta directly targets cytotoxic T cell functions during tumor evasion of immune surveillance. Cancer Cell 8:369-380.
5. Gerlini, G., Tun-Kyi, A., Dudli, C., Burg, G., Pimpinelli, N., and Nestle, F. O. 2004. Metastatic melanoma secreted IL-10 down-regulates CD1 molecules on dendritic cells in metastatic tumor lesions. Am J Pathol 165:1853-1863.
6. Turk, M. J., Guevara-Patino, J. A., Rizzuto, G. A., Engelhorn, M. E., Sakaguchi, S., and Houghton, A. N.

2004. Concomitant tumor immunity to a poorly immunogenic melanoma is prevented by regulatory T cells. J Exp Med 200:771-782.

7. Huang, B., Pan, P. Y., Li, Q., Sato, A. I., Levy, D. E., Bromberg, J., Divino, C. M., and Chen, S. H. 2006. Gr-1+CD115+ immature myeloid suppressor cells mediate the development of tumor-induced T regulatory cells and T-cell anergy in tumor-bearing host. Cancer Res 66:1123-1131.

8. Sica, A., and Bronte, V. 2007. Altered macrophage differentiation and immune dysfunction in tumor development. J Clin Invest 117:1155-1166.

9. Curiel, T. J., Coukos, G., Zou, L., Alvarez, X., Cheng, P., Mottram, P., Evdemon-Hogan, M., Conejo-Garcia, J. R., Zhang, L., Burow, M., et al. 2004. Specific recruitment of regulatory T cells in ovarian carcinoma fosters immune privilege and predicts reduced survival. Nat Med 10:942-949.

10. van Elsas, A., Hurwitz, A. A., and Allison, J. P. 1999. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med 190:355-366.

11. Phan, G. Q., Yang, J. C., Sherry, R. M., Hwu, P., Topalian, S. L., Schwartzentruber, D. J., Restifo, N. P., Haworth, L. R., Seipp, C. A., Freezer, L. J., et al. 2003. Cancer regression and autoimmunity induced by cytotoxic T lymphocyte-associated antigen 4 blockade in patients with metastatic melanoma. Proc Natl Acad Sci USA 100:8372-8377.

12. Dong, H., Strome, S. E., Salomao, D. R., Tamura, H., Hirano, F., Flies, D. B., Roche, P. C., Lu, J., Zhu, G., Tamada, K., et al. 2002. Tumor-associated B7-H1 promotes T-cell apoptosis: a potential mechanism of immune evasion. Nat Med 8:793-800.

13. Rubinstein, N., Alvarez, M., Zwirner, N. W., Toscano, M. A., Ilarregui, J. M., Bravo, A., Mordoh, J., Fainboim, L., Podhajcer, O. L., and Rabinovich, G. A. 2004. Targeted inhibition of galectin-1 gene expression in tumor cells results in heightened T cell-mediated rejection; A potential mechanism of tumor-immune privilege. Cancer Cell 5:241-251.

14. Troy, A. J., Summers, K. L., Davidson, P. J., Atkinson, C. H., and Hart, D. N. 1998. Minimal recruitment and activation of dendritic cells within renal cell carcinoma. Clin Cancer Res 4:585-593.

15. Staveley-O'Carroll, K., Sotomayor, E., Montgomery, J., Borrello, I., Hwang, L., Fein, S., Pardoll, D., and Levitsky, H. 1998. Induction of antigen-specific T cell anergy: An early event in the course of tumor progression. Proc Natl Acad Sci USA 95:1178-1183.

16. Willimsky, G., and Blankenstein, T. 2005. Sporadic immunogenic tumours avoid destruction by inducing T-cell tolerance. Nature 437:141-146.

17. Overwijk, W. W., Theoret, M. R., Finkelstein, S. E., Surman, D. R., de Jong, L. A., Vyth-Dreese, F. A., Dellemijn, T. A., Antony, P. A., Spiess, P. J., Palmer, D. C., et al. 2003. Tumor regression and autoimmunity after reversal of a functionally tolerant state of self-reactive CD8+ T cells. J Exp Med 198:569-580.

18. Cuenca, A., Cheng, F., Wang, H., Brayer, J., Horna, P., Gu, L., Bien, H., Borrello, I. M., Levitsky, H. I., and Sotomayor, E. M. 2003. Extra-lymphatic solid tumor growth is not immunologically ignored and results in early induction of antigen-specific T-cell anergy: dominant role of cross-tolerance to tumor antigens. Cancer Res 63:9007-9015.

19. Zheng, Y., Zha, Y., Driessens, G., Locke, F., and Gajewski, T. F. 2012. Transcriptional regulator early growth response gene 2 (Egr2) is required for T cell anergy in vitro and in vivo. J Exp Med 209:2157-2163.

31. Zhang, H. G., Mehta, K., Cohen, P., and Guha, C. 2008. Hyperthermia on immune regulation: a temperature's story. Cancer Lett 271:191-204.

32. Basu, S., and Srivastava, P. K. 1999. Calreticulin, a peptide-binding chaperone of the endoplasmic reticulum, elicits tumor- and peptide-specific immunity. J Exp Med 189:797-802.

33. Castelli, C., Ciupitu, A. M., Rini, F., Rivoltini, L., Mazzocchi, A., Kiessling, R., and Parmiani, G. 2001. Human heat shock protein 70 peptide complexes specifically activate antimelanoma T cells. Cancer Res 61:222-227.

34. Haug, M., Dannecker, L., Schepp, C. P., Kwok, W. W., Wernet, D., Buckner, J. H., Kalbacher, H., Dannecker, G. E., and Holzer, U. 2005. The heat shock protein Hsp70 enhances antigen-specific proliferation of human CD4+ memory T cells. Eur J Immunol 35:3163-3172.

35. Pawaria, S., and Binder, R. J. 2011. CD91-dependent programming of T-helper cell responses following heat shock protein immunization. Nat Commun 2:521.

36. Gajewski, T. F., Woo, S. R., Zha, Y., Spaapen, R., Zheng, Y., Corrales, L., and Spranger, S. 2013. Cancer immunotherapy strategies based on overcoming barriers within the tumor microenvironment. Curr Opin Immunol 25:268-276.

37. Driessens, G., Kline, J., and Gajewski, T. F. 2009. Costimulatory and coinhibitory receptors in anti-tumor immunity. Immunol Rev 229:126-144.

38. Leach, D. R., Krummel, M. F., and Allison, J. P. 1996. Enhancement of antitumor immunity by CTLA-4 blockade. Science 271:1734-1736.

39. Munn, D. H., and Mellor, A. L. 2007. Indoleamine 2,3-dioxygenase and tumor-induced tolerance. J Clin Invest 117:1147-1154.

40. Green, D. R., Ferguson, T., Zitvogel, L., and Kroemer, G. 2009. Immunogenic and tolerogenic cell death. Nat Rev Immunol 9:353-363.

41. Lee, P. P., Yee, C., Savage, P. A., Fong, L., Brockstedt, D., Weber, J. S., Johnson, D., Swetter, S., Thompson, J., Greenberg, P. D., et al. 1999. Characterization of circulating T cells specific for tumor-associated antigens in melanoma patients. Nat Med 5:677-685.

42. Valdor, R., and Macian, F. 2013. Induction and stability of the anergic phenotype in T cells. Semin Immunol 25:313-320.

43. Macian, F., Garcia-Cozar, F., Im, S. H., Horton, H. F., Byrne, M. C., and Rao, A. 2002. Transcriptional mechanisms underlying lymphocyte tolerance. Cell 109:719-731.

44. Safford, M., Collins, S., Lutz, M. A., Allen, A., Huang, C. T., Kowalski, J., Blackford, A., Horton, M. R., Drake, C., Schwartz, R. H., et al. 2005. Egr-2 and Egr-3 are negative regulators of T cell activation. Nat Immunol 6:472-480.

45. Soto-Nieves, N., Puga, I., Abe, B. T., Bandyopadhyay, S., Baine, I., Rao, A., and Macian, F. 2009. Transcriptional complexes formed by NFAT dimers regulate the induction of T cell tolerance. J Exp Med 206:867-876.

46. Enk, A. H., Jonuleit, H., Saloga, J., and Knop, J. 1997. Dendritic cells as mediators of tumor-induced tolerance in metastatic melanoma. Int J Cancer 73:309-316.
47. Marangoni, F., Murooka, T. T., Manzo, T., Kim, E. Y., Carrizosa, E., Elpek, N. M., and Mempel, T. R. 2013. The transcription factor NFAT exhibits signal memory during serial T cell interactions with antigen-presenting cells. Immunity 38:237-249.
48. Srivastava, P. 2002. Interaction of heat shock proteins with peptides and antigen presenting cells: chaperoning of the innate and adaptive immune responses. Annu Rev Immunol 20:395-425.
49. Udono, H., and Srivastava, P. K. 1993. Heat shock protein 70-associated peptides elicit specific cancer immunity. J Exp Med 178:1391-1396.
50. Udono, H., and Srivastava, P. K. 1994. Comparison of tumor-specific immunogenicities of stress-induced proteins gp96, hsp90, and hsp70. J Imunol 152:5398-5403.
51. Ullrich, S. J., Robinson, E. A., Law, L. W., Willingham, M., and Appella, E. 1986. A mouse tumor-specific transplantation antigen is a heat shock-related protein. Proc Natl Acad Sci USA 83:3121-3125.
52. Somersan, S., Larsson, M., Fonteneau, J. F., Basu, S., Srivastava, P., and Bhardwaj, N. 2001. Primary tumor tissue lysates are enriched in heat shock proteins and induce the maturation of human dendritic cells. J Immunol 167:4844-4852.
53. Liu, B., DeFilippo, A. M., and Li, Z. 2002. Overcoming Immune Tolerance to Cancer by Heat Shock Protein Vaccines. Mol Cancer Ther 1:1147-1151.
54. Chen, X., Tao, Q., Yu, H., Zhang, L., and Cao, X. 2002. Tumor cell membrane-bound heat shock protein 70 elicits antitumor immunity. Immunol Lett 84:81-87.
55. Vega, V. L., Rodriguez-Silva, M., Frey, T., Gehrmann, M., Diaz, J. C., Steinem, C., Multhoff, G., Arispe, N., and De Maio, A. 2008. Hsp70 translocates into the plasma membrane after stress and is released into the extracellular environment in a membrane-associated form that activates macrophages. J Immunol 180:4299-4307.
56. Basu, S., Binder, R. J., Suto, R., Anderson, K. M., and Srivastava, P. K. 2000. Necrotic but not apoptotic cell death releases heat shock proteins, which deliver a partial maturation signal to dendritic cells and activate the NF-kappa B pathway. Int immunol 12:1539-1546.
57. Obeid, M., Panaretakis, T., Tesniere, A., Joza, N., Tufi, R., Apetoh, L., Ghiringhelli, F., Zitvogel, L., and Kroemer, G. 2007. Leveraging the immune system during chemotherapy: moving calreticulin to the cell surface converts apoptotic death from "silent" to immunogenic. Cancer Res 67:7941-7944.
58. Hu, Z., Yang, X. Y., Liu, Y., Morse, M. A., Lyerly, H. K., Clay, T. M., and Zhong, P. 2005. Release of endogenous danger signals from HIFU-treated tumor cells and their stimulatory effects on APCs. Biochem Biophys Res Comm 335:124-131.
59. Hu, Z., Yang, X. Y., Liu, Y., Sankin, G. N., Pua, E. C., Morse, M. A., Lyerly, H. K., Clay, T. M., and Zhong, P. 2007. Investigation of HIFU-induced anti-tumor immunity in a murine tumor model. J Transl Med 5:34-34.
60. Boussiotis, V. A., Barber, D. L., Nakarai, T., Freeman, G. J., Gribben, J. G., Bernstein, G. M., D'Andrea, A. D., Ritz, J., and Nadler, L. M. 1994. Prevention of T cell anergy by signaling through the gamma c chain of the IL-2 receptor. Science 266:1039-1042.
61. Dure, M., and Macian, F. 2009. IL-2 signaling prevents T cell anergy by inhibiting the expression of anergy-inducing genes. Mol Immunol 46:999-1006.
62. Gao, B., Kong, Q., Kemp, K., Zhao, Y. S., and Fang, D. 2012. Analysis of sirtuin 1 expression reveals a molecular explanation of IL-2-mediated reversal of T-cell tolerance. Proc Natl Acad Sci USA 109:899-904.
63. Gramaglia, I., Weinberg, A. D., Lemon, M., and Croft, M. 1998. Ox-40 ligand: a potent costimulatory molecule for sustaining primary CD4 T cell responses. J Immunol 161:6510-6517.
64. Lathrop, S. K., Huddleston, C. A., Dullforce, P. A., Montfort, M. J., Weinberg, A. D., and Parker, D. C. 2004. A signal through OX40 (CD134) allows anergic, autoreactive T cells to acquire effector cell functions. J Immunol 172:6735-6743.
65. Murata, S., Ladle, B. H., Kim, P. S., Lutz, E. R., Wolpoe, M. E., Ivie, S. E., Smith, H. M., Armstrong, T. D., Emens, L. A., Jaffee, E. M., et al. 2006. OX40 costimulation synergizes with GM-CSF whole-cell vaccination to overcome established CD8+ T cell tolerance to an endogenous tumor antigen. J Immunol 176:974-983.
66. Tsushima, F., Yao, S., Shin, T., Flies, A., Flies, S., Xu, H., Tamada, K., Pardoll, D. M., and Chen, L. 2007. Interaction between B7-H1 and PD-1 determines initiation and reversal of T-cell anergy. Blood 110:180-185.
67. Wilcox, R. A., Tamada, K., Flies, D. B., Zhu, G., Chapoval, A. I., Blazar, B. R., Kast, W. M., and Chen, L. 2004. Ligation of CD137 receptor prevents and reverses established anergy of CD8+ cytolytic T lymphocytes in vivo. Blood 103:177-184.
68. Zhang, L., Chen, X., Liu, X., Kline, D. E., Teague, R. M., Gajewski, T. F., and Kline, J. 2013. CD40 ligation reverses T cell tolerance in acute myeloid leukemia. J Clin Invest 123:1999-2010.
69. Anelli T, Alessio M, Mezghrani A, Simmen T, Talamo F, Bachi A and Sitia R. ERp44, a novel endoplasmic reticulum folding assistant of the thioredoxin family. EMBO J. 2002; 21(4):835-844.
70. Jessop C E, Chakravarthi S, Garbi N, Hammerling G J, Lovell S and Bulleid N J. ERp57 is essential or efficient folding of glycoproteins sharing common structural domains. EMBO J. 2007; 26(1):28-40.
71. Ron D and Walter P. Signal integration in the endoplasmic reticulum unfolded protein response. Nat Rev Mol Cell Biol. 2007; 8(7):519-529.
72. White E. Deconvoluting the context-dependent role for autophagy in cancer. Nat Rev Cancer. 2012; 12(6):401-410.
73. Kon M, Kiffin R, Koga H, Chapochnick J, Macian F, Varticovski L and Cuervo A M. Chaperone-mediated autophagy is required for tumor growth. Sci Trans' Med. 2011; 3(109):109ra.117.
74. Haar G, Shaw A, Pye S, Ward B, Bottomley F, Nolan R and Coady A M. Guidance on reporting ultrasound exposure conditions for bio-effects studies. Ultrasound Med Biol. 2011; 37(2): 177-183.
75. Duck F A. (1990). Physical properties of tissue: a comprehensive reference book: Academic Press).
76. Partanen A, Tillander M, Yarmolenko P S, Wood B J, Dreher M R and Kohler M O. Reduction of peak acoustic pressure and shaping of heated region by use of multifoci sonications in MR-guided high-intensity focused ultrasound mediated mild hyperthermia. Med Phys. 2013; 40(1):013301.
77. Back S H, Schroder M, Lee K, Zhang K and Kaufman R J. ER stress signaling by regulated splicing: IRE1/HAC1/XBP1. Methods. 2005; 35(4):395-416.
78. Lewis and Olbricht, Review of Scientific Instruments 80, 114704 (2009).
79, Pouch et al. Ultrasound Med 2010; 29:1595-1606.
80. Sahu et al. Scientic Reports 2014 Dec. 3; 4:7303. doi: 10.1038/srep07303.

What is claimed is:

1. A method for priming a subject having a tumor, the method comprising:
   a. applying a priming therapy comprising non-ablative ultrasound comprising at least two ultrasound beams to a treatment zone in the subject having the tumor, wherein the at least two ultrasound beams have different frequencies, and wherein the at least two ultrasound beams have a beam profile waist at −3 dB that is not less than 5 mm in the treatment zone; and
   b. administering a chemotherapeutic agent to the subject, wherein the chemotherapeutic agent comprises a heat shock protein 90 (HSP90) inhibitor, wherein applying the priming therapy induces a stress in cells of the tumor in the treatment zone without ablating the cells.

2. The method of claim 1, wherein the HSP90 inhibitor comprises 17AAG (tanespimycin).

3. The method of claim 1, wherein one of the at least two ultrasound beams has a frequency in the range of 0.01 to 10 MHz and a spatial peak temporal average acoustic output intensity ($I_{spta}$) of between 1 and 1000 W/cm² in the treatment zone.

4. The method of claim 3, wherein the frequency of the one of the at least two ultrasound beams is in the range of 30 to 300 kHz.

5. The method of claim 3, wherein another of the at least two ultrasound beams has a frequency in the range of 300 kHz to 3 MHz.

6. The method of claim 3, wherein the spatial peak temporal average acoustic output intensity ($I_{spta}$) of the one of the at least two ultrasound beams is between 10 and 300 W/cm² in the treatment zone.

7. The method of claim 1, wherein the at least two ultrasound beams are applied for 0.5 to 5 seconds.

8. The method of claim 1, wherein the priming therapy is applied to the cells of the tumor in the treatment zone to increase a non-ablative stress in the cells.

9. The method of claim 8, wherein the priming therapy is applied to the cells of the tumor in the treatment zone to increase endoplasmic reticulum (ER) stress in the cells.

10. The method of claim 9, wherein the increased ER stress increases intensity and effectiveness of a T-cell mediated response to the anti-tumor therapy.

11. The method of claim 1, wherein the priming therapy is applied to the cells of the tumor in the treatment zone are to induce a release of an immunomodulatory factor.

12. The method of claim 11, wherein the immunomodulatory factor comprises a heat shock protein.

13. The method of claim 1, wherein the ultrasound is applied to the treatment zone in the subject before the chemotherapeutic agent.

14. The method of claim 1, wherein the ultrasound is applied to the treatment zone in the subject concurrent with the chemotherapeutic agent.

15. The method of claim 1, wherein the at least two ultrasound beams are applied sequentially.

16. The method of claim 1, wherein the at least two ultrasound beams are applied simultaneously.

17. The method of claim 1, wherein the tumor comprises a tumor of the prostate, breast, nasopharynx, pharynx, lung, bone, brain, sialaden, stomach, esophagus, testes, ovary, uterus, endometrium, liver, small intestine, appendix, colon, rectum, bladder, gall bladder, pancreas, kidney, urinary bladder, cervix, vagina, vulva, prostate, thyroid or skin, head or neck, glioma or soft tissue sarcoma.

18. The method of claim 1, wherein the tumor has become resistant to the chemotherapeutic agent when the chemotherapeutic agent was previously administered to the subject.

19. The method of claim 1, wherein the ultrasound delivers an energy in the range of 300 to 3000 $J/cm^3$ in the treatment zone of the subject.

20. The method of claim 1, wherein the treatment zone is configured to reach a maximum temperature of less than 55° C.

* * * * *

UNITED STATES PATENT AND TRADEMARK OFFICE
CERTIFICATE OF CORRECTION

| | | |
|---|---|---|
| PATENT NO. | : 12,011,619 B2 | Page 1 of 1 |
| APPLICATION NO. | : 17/191497 | |
| DATED | : June 18, 2024 | |
| INVENTOR(S) | : Chandan Guha et al. | |

It is certified that error appears in the above-identified patent and that said Letters Patent is hereby corrected as shown below:

In the Specification

In Column 1, Lines 20-23, under the "STATEMENT OF GOVERNMENT SUPPORT" delete the paragraph and replace it with the following paragraph:
-- This invention was made with government support under grant numbers EB009040, CA226861, and AI059738 awarded by the National Institutes of Health. The government has certain rights in the invention. --

Signed and Sealed this
Eleventh Day of March, 2025

Coke Morgan Stewart
*Acting Director of the United States Patent and Trademark Office*

SEQUENCE LISTING

<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: forward primer for actinb

<400> SEQUENCE: 1
gtgacgttga catccgtaaa ga                                          22

<210> SEQ ID NO 2
<211> LENGTH: 19
<212> TYPE: DNA
<213> ORGANISM: Artificial Sequence
<220> FEATURE:
<223> OTHER INFORMATION: reverse primer for actinb

<400> SEQUENCE: 2
gccggactca tcgtactcc                                              19

<210> SEQ ID NO 3
<211> LENGTH: 21
<212> TYPE: DNA
<213> ORGANISM: Artificial Sequence
<220> FEATURE:
<223> OTHER INFORMATION: forward primer for Cblb

<400> SEQUENCE: 3
gcagcatcat tgaccctttc a                                           21

<210> SEQ ID NO 4
<211> LENGTH: 21
<212> TYPE: DNA
<213> ORGANISM: Artificial Sequence
<220> FEATURE:
<223> OTHER INFORMATION: reverse primer for Cblb

<400> SEQUENCE: 4
atgtgactgg tgagttctgc c                                           21

<210> SEQ ID NO 5
<211> LENGTH: 24
<212> TYPE: DNA
<213> ORGANISM: Artificial Sequence
<220> FEATURE:
<223> OTHER INFORMATION: forward primer for Grail

<400> SEQUENCE: 5
atgcaagagc tcaaagcagg aagc                                        24

<210> SEQ ID NO 6
<211> LENGTH: 24
<212> TYPE: DNA
<213> ORGANISM: Artificial Sequence
<220> FEATURE:
<223> OTHER INFORMATION: reverse primer for Grail

<400> SEQUENCE: 6
gtgcgcagct gaagctttcc aata                                        24

```
<210> SEQ ID NO 7
<211> LENGTH: 17
<212> TYPE: DNA
<213> ORGANISM: Artificial Sequence
<220> FEATURE:
<223> OTHER INFORMATION: forward primer for Ikaros

<400> SEQUENCE: 7
gctggctctc ggaggag                                                    17

<210> SEQ ID NO 8
<211> LENGTH: 20
<212> TYPE: DNA
<213> ORGANISM: Artificial Sequence
<220> FEATURE:
<223> OTHER INFORMATION: reverse primer for Ikaros

<400> SEQUENCE: 8
cgcacttgta caccttcagc                                                 20

<210> SEQ ID NO 9
<211> LENGTH: 20
<212> TYPE: DNA
<213> ORGANISM: Artificial Sequence
<220> FEATURE:
<223> OTHER INFORMATION: forward primer for Caspase3

<400> SEQUENCE: 9
acgcgcacaa gctagaattt                                                 20

<210> SEQ ID NO 10
<211> LENGTH: 20
<212> TYPE: DNA
<213> ORGANISM: Artificial Sequence
<220> FEATURE:
<223> OTHER INFORMATION: reverse primer for Caspase3

<400> SEQUENCE: 10
ctttgcgtgg aaagtggagt                                                 20

<210> SEQ ID NO 11
<211> LENGTH: 21
<212> TYPE: DNA
<213> ORGANISM: Artificial Sequence
<220> FEATURE:
<223> OTHER INFORMATION: forward primer Egr2

<400> SEQUENCE: 11
tcagtggttt tatgcaccag c                                               21

<210> SEQ ID NO 12
<211> LENGTH: 21
<212> TYPE: DNA
<213> ORGANISM: Artificial Sequence
<220> FEATURE:
<223> OTHER INFORMATION: reverse primer for Egr2

<400> SEQUENCE: 12
gaagctactc ggatacggga g                                               21

<210> SEQ ID NO 13
<211> LENGTH: 20
<212> TYPE: DNA
<213> ORGANISM: Artificial Sequence
<220> FEATURE:
<223> OTHER INFORMATION: forward primer Grg4
```

<400> SEQUENCE: 13
tcactcaagt ttgcccactg          20

<210> SEQ ID NO 14
<211> LENGTH: 20
<212> TYPE: DNA
<213> ORGANISM: Artificial Sequence
<220> FEATURE:
<223> OTHER INFORMATION: reverse primer for Grg4

<400> SEQUENCE: 14
cacagctaag caccgatgag          20

<210> SEQ ID NO 15
<211> LENGTH: 20
<212> TYPE: DNA
<213> ORGANISM: Artificial Sequence
<220> FEATURE:
<223> OTHER INFORMATION: forward primer for Itch

<400> SEQUENCE: 15
gtgtggagtc accagaccct          20

<210> SEQ ID NO 16
<211> LENGTH: 20
<212> TYPE: DNA
<213> ORGANISM: Artificial Sequence
<220> FEATURE:
<223> OTHER INFORMATION: reverse primer for Itch

<400> SEQUENCE: 16
gcttctactt gcagcccatc          20

<210> SEQ ID NO 17
<211> LENGTH: 19
<212> TYPE: DNA
<213> ORGANISM: Artificial Sequence
<220> FEATURE:
<223> OTHER INFORMATION: Foxp3

<400> SEQUENCE: 17
ggcccttctc caggacaga          19

<210> SEQ ID NO 18
<211> LENGTH: 20
<212> TYPE: DNA
<213> ORGANISM: Artificial Sequence
<220> FEATURE:
<223> OTHER INFORMATION: Foxp3

<400> SEQUENCE: 18
gctgatcatg gctgggttgt          20

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
actcggtctg gaaatctg          18

```
<210> SEQ ID NO 20
<211> LENGTH: 18
<212> TYPE: DNA
<213> ORGANISM: Artificial Sequence
<220> FEATURE:
<223> OTHER INFORMATION: primer based on human sequence

<400> SEQUENCE: 20
tagccaggaa acgtctac                                                       18

<210> SEQ ID NO 21
<211> LENGTH: 24
<212> TYPE: DNA
<213> ORGANISM: Artificial Sequence
<220> FEATURE:
<223> OTHER INFORMATION: primer based on human sequence

<400> SEQUENCE: 21
ttgcttatgg cctggataag aggg                                                24

<210> SEQ ID NO 22
<211> LENGTH: 24
<212> TYPE: DNA
<213> ORGANISM: Artificial Sequence
<220> FEATURE:
<223> OTHER INFORMATION: primer based on human sequence

<400> SEQUENCE: 22
tgtacccttg tcttcagctg tcac                                                24

<210> SEQ ID NO 23
<211> LENGTH: 24
<212> TYPE: DNA
<213> ORGANISM: Artificial Sequence
<220> FEATURE:
<223> OTHER INFORMATION: primer based on human sequence

<400> SEQUENCE: 23
tcatccgagt tccagaaagc agtc                                                24

<210> SEQ ID NO 24
<211> LENGTH: 24
<212> TYPE: DNA
<213> ORGANISM: Artificial Sequence
<220> FEATURE:
<223> OTHER INFORMATION: primer based on human sequence

<400> SEQUENCE: 24
ttgacataga gtggagggtc tcct                                                24
```